United States Patent
Bentzien et al.

(10) Patent No.: US 10,138,229 B2
(45) Date of Patent: Nov. 27, 2018

(54) HETEROAROMATIC COMPOUNDS AS BTK INHIBITORS

(71) Applicant: Boehringer Ingelheim International GmbH, Ingelheim am Rhein (DE)

(72) Inventors: Joerg Bentzien, White Plains, NY (US); Angela Kay Berry, Gaylordsville, CT (US); Todd Bosanac, New Milford, CT (US); Michael Jason Burke, Newtown, CT (US); Darren Todd Disalvo, New Milford, CT (US); Joshua Courtney Horan, Somerville, MA (US); Shuang Liang, Roseville, MN (US); Can Mao, Philadelphia, PA (US); Wang Mao, Milford, CT (US); Yue Shen, Ridgefield, CT (US); Fariba Soleymanzadeh, Danbury, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/814,927

(22) Filed: Nov. 16, 2017

(65) Prior Publication Data

US 2018/0086748 A1    Mar. 29, 2018

Related U.S. Application Data

(63) Continuation of application No. 15/661,644, filed on Jul. 27, 2017, now abandoned, which is a continuation of application No. 14/884,826, filed on Oct. 16, 2015, now abandoned, which is a continuation of application No. 13/962,260, filed on Aug. 8, 2013, now abandoned.

(60) Provisional application No. 61/681,684, filed on Aug. 10, 2012.

(51) Int. Cl.
| | | |
|---|---|---|
| C07D 403/04 | (2006.01) | |
| C07D 403/06 | (2006.01) | |
| C07D 403/08 | (2006.01) | |
| C07D 231/14 | (2006.01) | |
| C07D 413/14 | (2006.01) | |
| C07D 401/04 | (2006.01) | |
| C07D 401/14 | (2006.01) | |
| C07D 401/02 | (2006.01) | |
| C07D 277/56 | (2006.01) | |
| C07D 231/40 | (2006.01) | |
| C07D 231/38 | (2006.01) | |
| C07D 417/04 | (2006.01) | |
| C07D 417/06 | (2006.01) | |
| C07D 417/08 | (2006.01) | |
| C07D 405/14 | (2006.01) | |
| C07D 401/06 | (2006.01) | |
| C07D 417/02 | (2006.01) | |

(52) U.S. Cl.
CPC ......... *C07D 417/08* (2013.01); *C07D 231/14* (2013.01); *C07D 231/38* (2013.01); *C07D 231/40* (2013.01); *C07D 277/56* (2013.01); *C07D 401/02* (2013.01); *C07D 401/04* (2013.01); *C07D 401/06* (2013.01); *C07D 401/14* (2013.01); *C07D 403/04* (2013.01); *C07D 403/06* (2013.01); *C07D 403/08* (2013.01); *C07D 405/14* (2013.01); *C07D 413/14* (2013.01); *C07D 417/02* (2013.01); *C07D 417/04* (2013.01); *C07D 417/06* (2013.01)

(58) Field of Classification Search
None
See application file for complete search history.

(56) References Cited

U.S. PATENT DOCUMENTS

| | | | |
|---|---|---|---|
| 7,560,571 B2 | 7/2009 | Ronan et al. | |
| 8,377,946 B1 | 2/2013 | Chen et al. | |
| 8,557,803 B2 | 10/2013 | Yamamoto et al. | |
| 9,926,299 B2 * | 3/2018 | Han ..................... | C07D 231/38 |

(Continued)

FOREIGN PATENT DOCUMENTS

| | | |
|---|---|---|
| CA | 2784647 A1 | 7/2011 |
| EP | 2543375 A1 | 1/2013 |

(Continued)

OTHER PUBLICATIONS

Abstract in English for WO 2011/082732, publication date Jul. 14, 2011.

(Continued)

*Primary Examiner* — Kamal Saeed
(74) *Attorney, Agent, or Firm* — Atabak R. Royaee

(57) ABSTRACT

The present invention encompasses compounds of the formula (I)

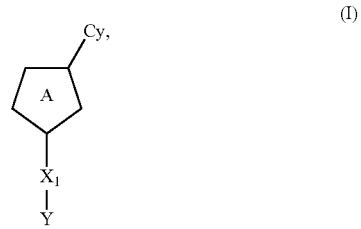

wherein the groups A, Cy, X1 and Y are defined herein, which are suitable for the treatment of diseases related to BTK, process of making, pharmaceutical preparations which contain compounds and their methods of use.

20 Claims, No Drawings

(56) References Cited

U.S. PATENT DOCUMENTS

| | | |
|---|---|---|
| 2004/0198986 A1 | 10/2004 | Adams et al. |
| 2008/0045542 A1 | 2/2008 | Ronan et al. |
| 2008/0076921 A1 | 3/2008 | Honigberg et al. |
| 2009/0012309 A1 | 1/2009 | Adams et al. |
| 2011/0003806 A1 | 1/2011 | Hirose et al. |
| 2014/0045813 A1 | 2/2014 | Bentzien et al. |
| 2016/0340339 A1 | 11/2016 | Bentzien et al. |

FOREIGN PATENT DOCUMENTS

| | | |
|---|---|---|
| WO | 199740019 A1 | 10/1997 |
| WO | 2003015776 A1 | 2/2003 |
| WO | 2007117692 A2 | 10/2007 |
| WO | 2008039218 A2 | 4/2008 |
| WO | 2008121742 A2 | 10/2008 |
| WO | 2010012690 A1 | 2/2010 |
| WO | 2010055304 A2 | 5/2010 |
| WO | 2010090716 A1 | 8/2010 |
| WO | 2011082732 A1 | 7/2011 |
| WO | 2011152351 A1 | 12/2011 |
| WO | 2012021615 A1 | 2/2012 |
| WO | 2013113097 A1 | 8/2013 |
| WO | 2014025976 A1 | 2/2014 |
| WO | 2014068527 A1 | 5/2014 |
| WO | 2014082598 A1 | 6/2014 |

OTHER PUBLICATIONS

Akinleye, A. et al., "Ibrutinib and novel BTK inhibitors in clinical develoopment." Journal of Hematology & Oncology, 2013, 6:59, pp. 1-9.

Chakravarty, S. et al., "Kinase inhibitors: A new tool for the treatment of rheumatoid arthritis." Clinical Immunology, 2013, vol. 148, pp. 66-78.

International Search Report and Written Opinion for PCT/US2013/054096 dated Sep. 30, 2013.

International Search Report and Written Opinion for PCT/US2014/026113, dated Jun. 2, 2014.

International Search Report and Written Opinion for PCT/US2014/026966, dated Jul. 22, 2014.

Summary of Pfizer Oral Presentation, "Targeted covalent reversible inhibitors for Bruton's Tyrosine Kinase." Presented Suvit Thaisrivongs on Apr. 16, 2013.

Whang, J. et al., "Bruton's tyrosine kinase inhibitors for the treatment of rheumatoid arthritis." Drug Discovery Today, 2014, pp. 1-5.

International Search Report and Written Opinion for PCT/US2015/012590 dated Mar. 25, 2015.

International Search Report for PCT/US2015/012590 dated Mar. 25, 2015.

International Search Report PCT/US2016/066799 dated Jul. 12, 2017. 4 pgs.

* cited by examiner

HETEROAROMATIC COMPOUNDS AS BTK INHIBITORS

BACKGROUND OF THE INVENTION

1. Technical Field

The present invention relates to novel compounds which inhibit BTK and their use as medicaments.

2. Background Information

Members of the protein kinase family of human enzymes play important regulatory roles in a multitude of distinct signal transduction processes due to their post-translational modification of specific proteins via the addition of a phosphate group (Hunter, *Cell*, 1987 50, 823-829). Bruton's tyrosine kinase (BTK) is a member of the Tec family of tyrosine kinases and plays a critical role in B cell development, activation and antibody production.

The contribution of BTK to B cell biology is exemplified in the X-linked agammaglobulinemia (XLA) immunodeficiency in humans (reviewed in Lindvall, Immunol Rev 2005, 203, 200-215 that display attenuated calcium signaling upon BCR engagement, lack mature B cells in periphery due to block between pro- and pre-B cells stage and have lower levels of circulating antibodies than normal healthy subjects. The outcome of recent clinical trials with B cell depleting anti-CD20 molecules in diseases such as rheumatoid arthritis (RA) and multiple sclerosis (MS) support the hypothesis that B cells offer an important intervention node for controlling autoimmune disorders (Townsend et al. 2010). As such, attenuation of B cell activation and proliferation via inhibition of BTK may offer similar therapeutic benefit and is consistent with the demonstrated resistance of BTK-deficient mice to collagen induced arthritis (Jansson, 1993, Clin Exp Immunol 94, 459-xxx) and experimental autoimmune encephalitis (Svensson et al. 2002 and Mangla et al 2004). Similarly, the clinical efficacy observed with a neutralizing antibody to the B cell stimulating factor BlyS supports a role for B cells in the pathophysiology of systemic lupus erythematosus (SLE) (La Cava 2010). Given the necessity for BTK for the production of autoantibodies, including anti-DNA antibodies, in murine models of SLE (Steinberg et al., 1982; Golding et al., 1983; Scribner et al., 1987; Seldin et al., 1987; Satterthwaite et al., 1998; Takeshita et al., 1998; Whyburn et. al., 2003), BTK inhibitors may offer therapeutic benefit to SLE patients.

Within myeloid cells, BTK signal transduction is necessary for the stimulated release of inflammatory cytokines such as TNF from stimulated monocytes (Horwood, J Exp Med, 2003, 1603-xxx) and for optimal actin cytoskeletal organization and lacunar bone resorption in isolated osteoclasts (Danks, 2011, J Bone and Mineral Research, 26, 182-192). Bone marrow derived mast cells lacking BTK exhibit impaired activation-induced degranulation and cytokine release (ref). Given the role of BTK in signal transduction processes across multiple cell types implicated in the pathogenesis of autoimmune and allergic disorders, inhibition of BTK activity may provide clinical benefit in diseases such as RA, MS, SLE, asthma and allergic disorders.

SUMMARY OF THE INVENTION

The invention comprises a novel class of heteroaromatic compounds and methods for making and using the same. These compounds are useful for the treatment of autoimmune and allergic disorders in that they exhibit good inhibitory effect upon BTK.

DETAILED DESCRIPTION OF THE INVENTION

In a first generic embodiment, there is provided a compound of the formula (I)

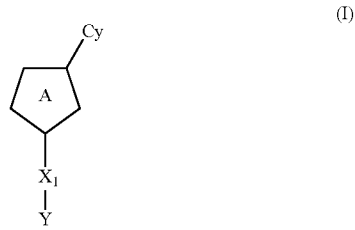

A ring is:

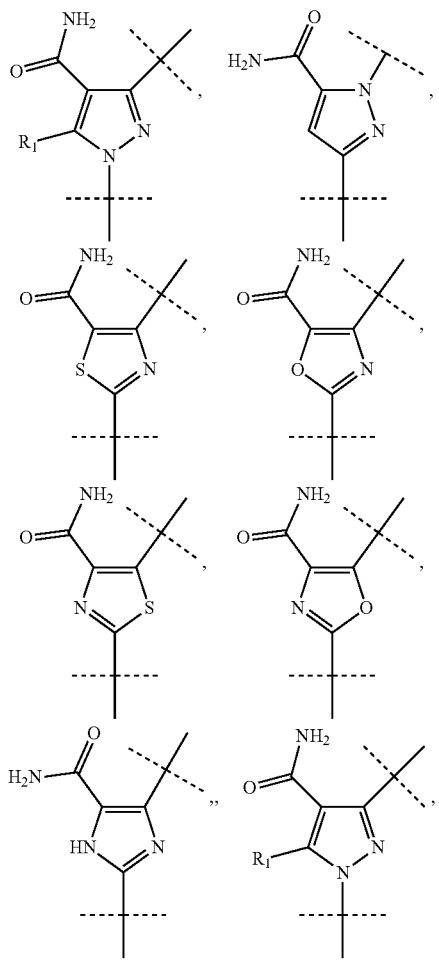

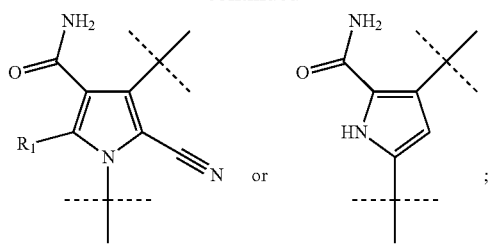

$R_1$ is $N(R_3)_2$ or hydrogen;

Cy is aryl or heteroaryl each is substituted by $R_2$ and optionally substituted by halogen, halo $C_{1-4}$ alkyl, $C_{1-4}$ alkyl and $C_{1-4}$ alkoxy;

$R_2$ is chosen from:

L-Ar, $C_{1-6}$ alkyl and $C_{1-6}$ alkoxy, each Ar, $C_{1-6}$ alkyl and $C_{1-6}$ alkoxy are optionally substituted by halogen, halo $C_{1-4}$ alkyl, $C_{1-4}$ alkyl, $R_3$—$S(O)_m$—, —CN, —C(O)—$N(R_3)_2$ or $C_{1-4}$ alkoxy;

L is a linker chosen from a bond, O, >C(O), —$(CH_2)_n$—, —O—$(CH_2)_n$—, —$N(R_3)$—, —$N(R_3)$—$(CH_2)_n$—, —$(CH_2)_n$—$N(R_3)$—, —C(O)—$N(R_3)$—, —C(O)—N$(R_3)$—$(CH_2)_n$—, —$N(R_3)$—C(O)—$N(R_3)$—, —$N(R_3)$—C(O)—, —$S(O)_m$—$N(R_3)$— and —$N(R_3)$—$S(O)_m$—, wherein the —$CH_2$— in each L can have 1-2 hydrogens replaced by $C_{1-3}$ alkyl, said $C_{1-3}$ alkyl groups can optionally cyclize to form a $C_{3-6}$ cycloalkyl ring;

Ar is carbocycle, heterocycyl or heteroaryl;

$X_1$ is a linker chosen from a bond, —$(CH_2)_n$—;

Y is chosen from $C_7$-$C_{10}$ spirocycle optionally containing 0-1 ring nitrogen atoms, a nitrogen containing mono- or bi-cyclic heterocycle, carbocycle, aryl, each substituted by one $R_4$;

$R_4$ is

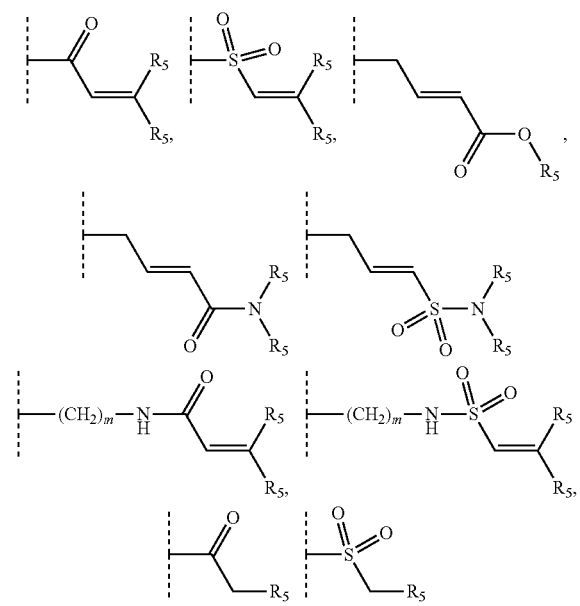

wherein $R_5$ cannot be hydrogen,

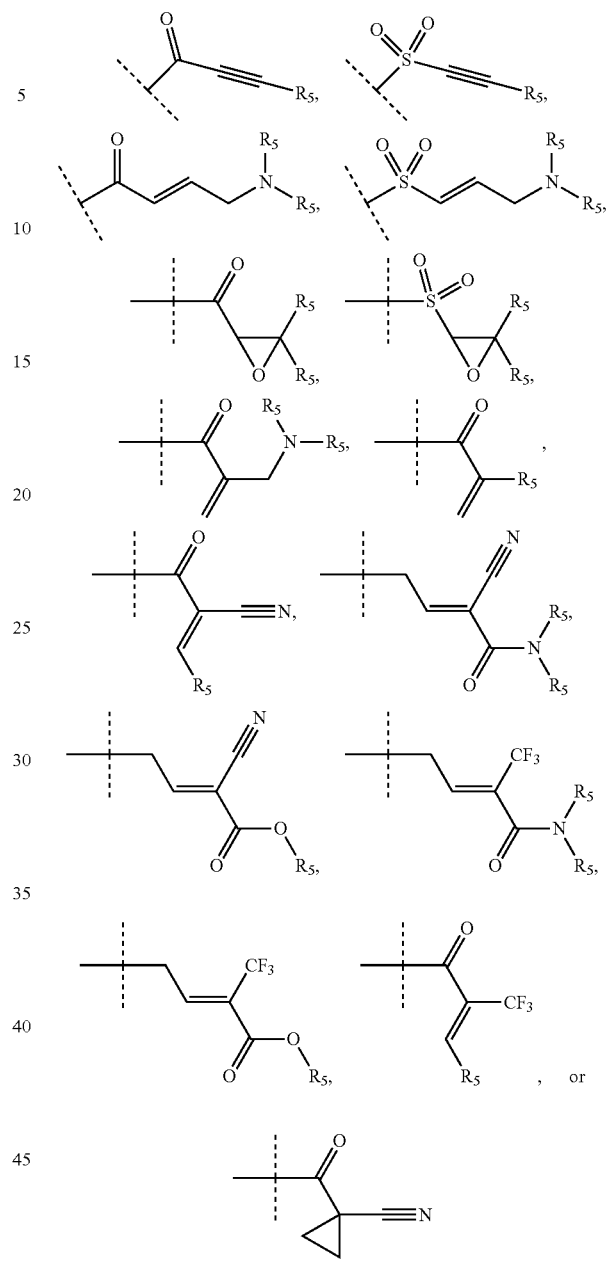

each n is independently 1-4;

each m is independently 0-2;

each $R_3$ is independently chosen from hydrogen or $C_{1-4}$ alkyl;

each $R_5$ is independently chosen from hydrogen, $C_{1-4}$ alkyl, $C_{1-4}$ alkoxy, $C_{1-4}$ alkyl$C_{1-4}$ alkoxy, —$(CH_2)_n$-heterocycle and heterocycle each heterocycle optionally substituted by halogen, OH and $R_3$—$S(O)_m$—;

each group defined above for Cy, $R_1$-$R_5$, $X_1$ and Y can be where possible partially or fully halogenated;

or a pharmaceutically acceptable salt thereof.

In a further embodiment, there is provided a compound of the formula (I) according to the embodiment herein-above and wherein A ring is:

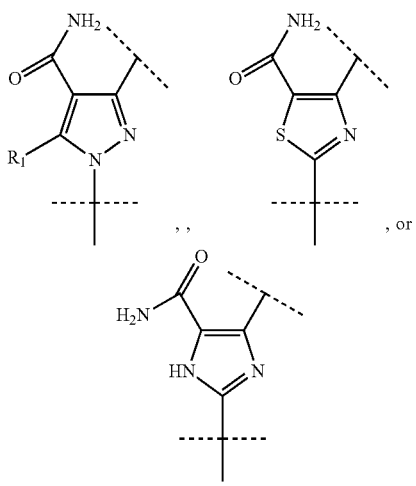

, , or or a pharmaceutically acceptable salt thereof.

In a further embodiment, there is provided a compound of the formula (I) according to any of the embodiments hereinabove and wherein Cy is phenyl, pyridinyl, pyridazinyl, pyrimidinyl or pyrazinyl each is substituted by $R_2$ and optionally substituted by F, Cl or $C_{1-4}$ alkoxy;

$R_2$ is chosen from:

L-Ar and $C_{1-3}$ alkoxy, each Ar and $C_{1-3}$ alkoxy are optionally substituted by F, Cl, $C_{1-4}$ alkyl, $R_3$—$S(O)_2$—, —CN, —C(O)—NH($R_3$) and $C_{1-3}$ alkoxy;

L is a linker chosen from a bond, O, >C(O), —$CH_2$—, —O—$CH_2$—, —NH—, —NH—$CH_2$—, —$CH_2$—NH—, —C(O)—NH—$CH_2$—, —NH—C(O)—NH— and —N($R_3$)—$S(O)_m$—;

Ar is phenyl, pyridinyl, pyridazinyl, pyrimidinyl, pyrazinyl, benzoxazolyl, indolyl, isoindolyl, benzofuranyl, benzimidazolyl, benzothiazolyl, piperidinyl, piperazinyl or pyrrolidinyl or a pharmaceutically acceptable salt thereof.

In a further embodiment, there is provided a compound of the formula (I) according to any of the embodiments hereinabove and wherein Cy is phenyl or pyridinyl, each is substituted by $R_2$ and optionally substituted by F, Cl or $C_{1-2}$ alkoxy;

$R_2$ is chosen from:

L-Ar and $C_{1-3}$ alkoxy, each Ar and $C_{1-3}$ alkoxy are optionally substituted by F, Cl, $C_{1-4}$ alkyl, $CH_3$—$S(O)_2$—, —CN, —C(O)—NH($R_3$) and $C_{1-2}$ alkoxy;

L is a linker chosen from a bond, O, >C(O), —$CH_2$—, —O—$CH_2$—, —NH—, —NH—$CH_2$—, —$CH_2$—NH—, —C(O)—NH—$CH_2$—, —NH—C(O)—NH— and —N($R_3$)—$S(O)_m$—;

Ar is phenyl, pyridinyl, pyridazinyl, pyrimidinyl, pyrazinyl, benzoxazolyl, indolyl, isoindolyl, benzofuranyl, benzimidazolyl, benzothiazolyl or piperidinyl or a pharmaceutically acceptable salt thereof.

In a further embodiment, there is provided a compound of the formula (I) according to any of the embodiments hereinabove and wherein Cy is phenyl or pyridinyl, each is substituted by $R_2$ and optionally substituted by F, Cl or $C_{1-2}$ alkoxy;

$R_2$ is chosen from:

L-Ar and $C_{1-3}$ alkoxy, each Ar and $C_{1-3}$ alkoxy are optionally substituted by F, Cl, $C_{1-4}$ alkyl, $CH_3$—$S(O)_2$—, —CN, —C(O)—NH($CH_3$) and $C_{1-2}$ alkoxy;

L is a linker chosen from a bond, O, >C(O), —$CH_2$—, —O—$CH_2$—, —NH—, —NH—$CH_2$—, —$CH_2$—NH—, —C(O)—NH—$CH_2$—, —NH—C(O)—NH— and —N(H)—$S(O)_2$—;

Ar is phenyl, pyridinyl, benzoxazolyl or piperidinyl or a pharmaceutically acceptable salt thereof.

In a further embodiment, there is provided a compound of the formula (I) according to any of the embodiments hereinabove and wherein $X_1$ is a linker chosen from a bond and —$(CH_2)_n$—;

Y is chosen from:

a spirocycle chosen from

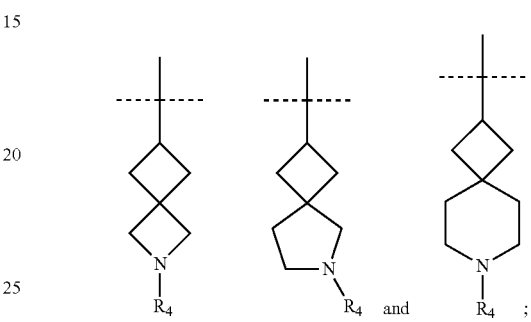

$R_4$          $R_4$ and    $R_4$    ;

a heterocycle chosen from piperidinyl and pyrrolidinyl; and phenyl each heterocycle or phenyl substituted by one $R_4$;

$R_4$ is

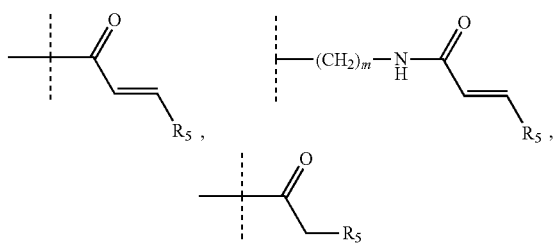

$R_5$ ,                        $R_5$ , $R_5$ wherein $R_5$ cannot be hydrogen,

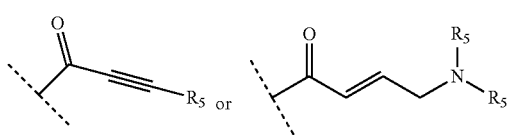

$R_5$ or                $R_5$ each $R_4$ is optionally halogenated;

each $R_5$ is independently chosen from hydrogen, $C_{1-3}$ alkyl, halo $C_{1-3}$ alkyl, $C_{1-3}$ alkyl$C_{1-3}$ alkoxy, —$CH_2$-heterocycle and heterocycle each heterocycle optionally substituted by F, Cl, OH and $CH_3$—$S(O)_2$— and each heterocycle chosen from pyrrolidinyl, piperidinyl, morpholinyl and 1,4-oxazepane, or a pharmaceutically acceptable salt thereof.

In a further embodiment, there is provided a compound of the formula (I) according to any of the embodiments hereinabove and wherein $X_1$ is a linker chosen from a bond and —$(CH_2)_n$—;

Y is chosen from:
a spirocycle chosen from

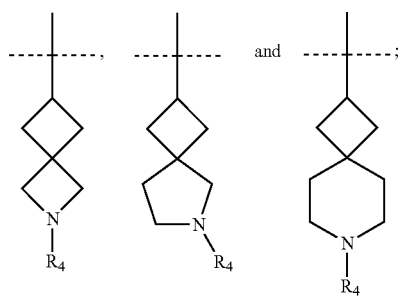

a heterocycle chosen from piperidinyl and pyrrolidinyl; and phenyl each heterocycle or phenyl substituted by one $R_4$;

$R_4$ is

$X_3$=halogen or hydrogen,

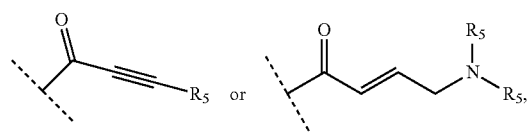

each $R_5$ is independently chosen from hydrogen, $C_{1-3}$ alkyl, —$CF_3$, $C_{1-3}$ alkyl$C_{1-3}$ alkoxy, —$CH_2$-heterocycle and heterocycle each heterocycle optionally substituted by F, Cl, OH and $CH_3$—$S(O)_2$— and each heterocycle chosen from pyrrolidinyl, piperidinyl and 1,4-oxazepane, or a pharmaceutically acceptable salt thereof.

In a further embodiment, there is provided a compound of the formula (I) according to any of the embodiments hereinabove and wherein
Cy is

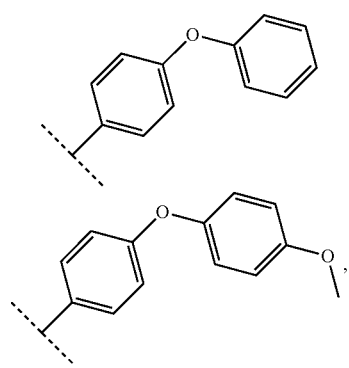

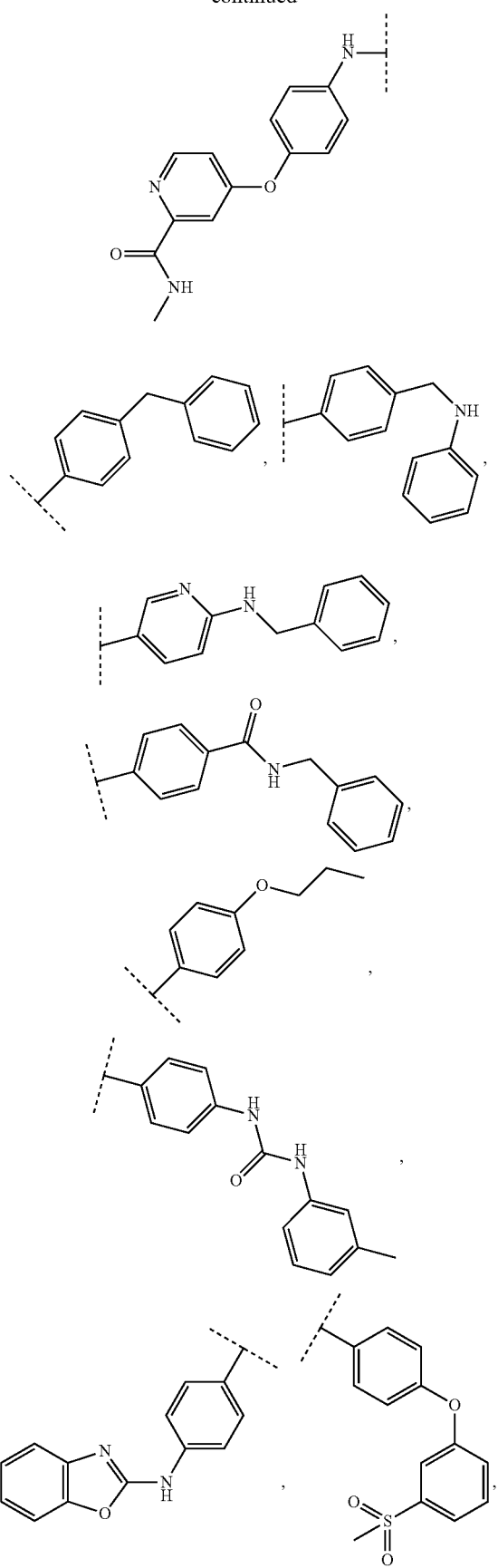
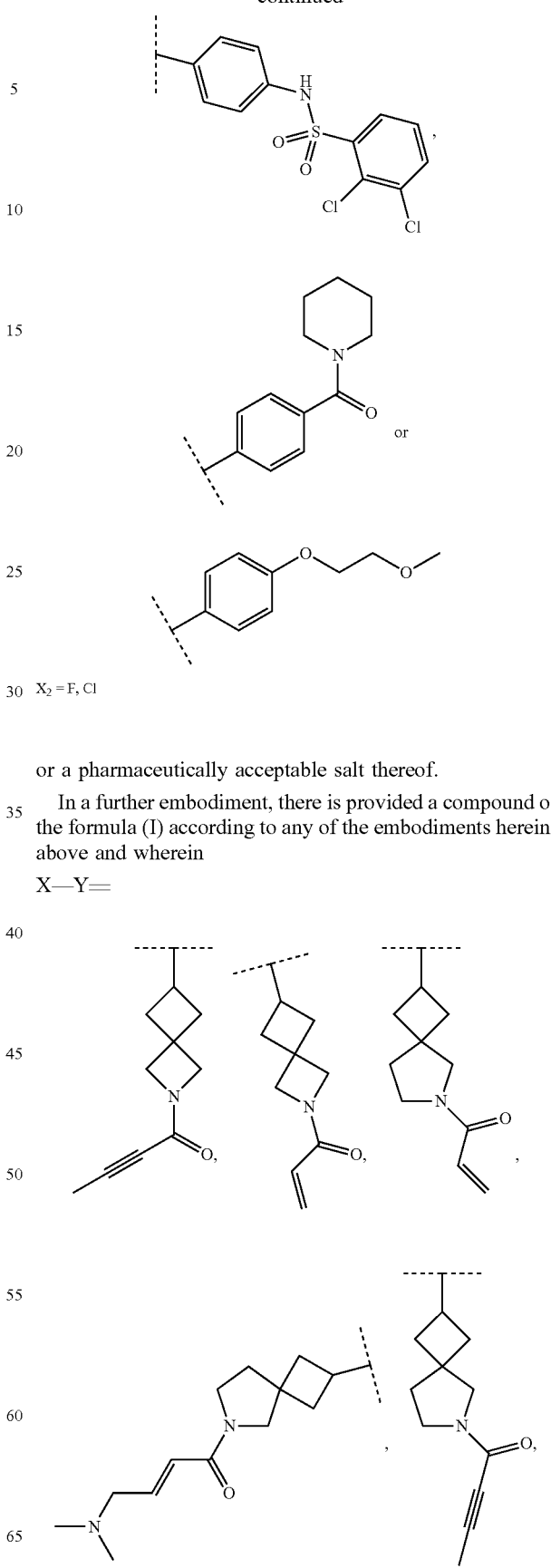
$X_2 = F, Cl$
or a pharmaceutically acceptable salt thereof.
In a further embodiment, there is provided a compound of the formula (I) according to any of the embodiments hereinabove and wherein
X—Y=

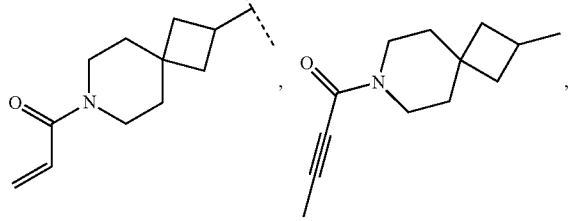
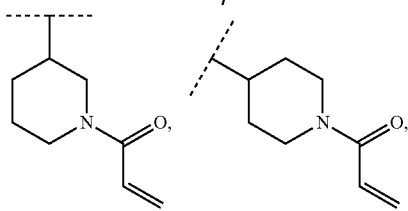
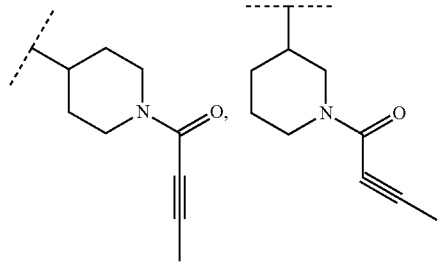
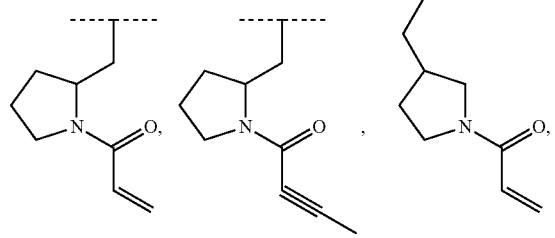
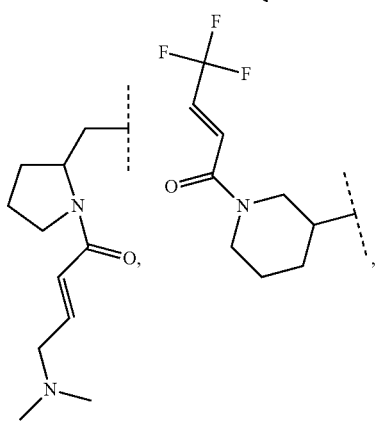
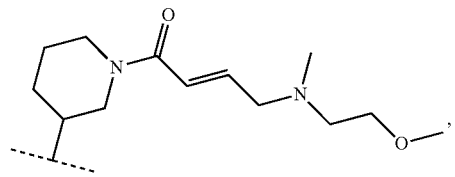
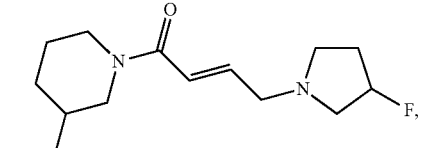
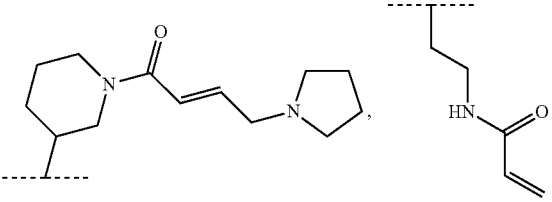
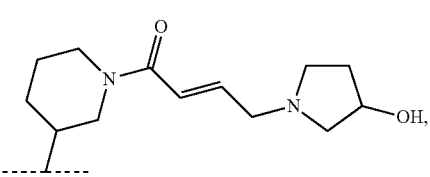
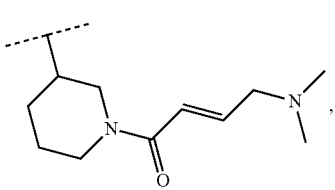
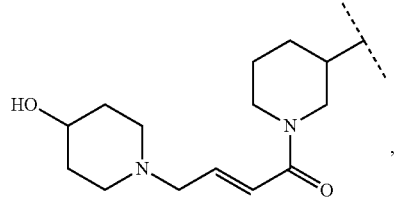
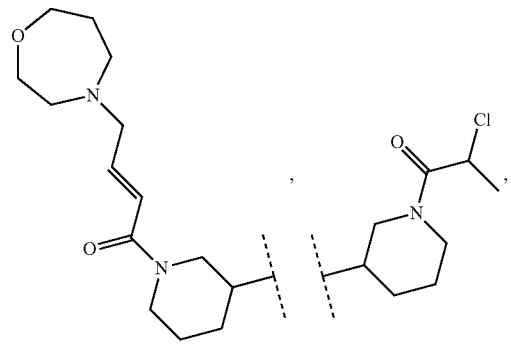
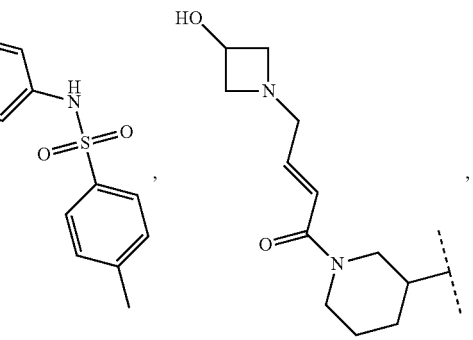

-continued

[structure: methylsulfonyl-piperidine-butenoyl-piperidine]

or a pharmaceutically acceptable salt thereof.

In a further embodiment, there is provided a compound of the formula (I) according to any of the embodiments hereinabove and wherein
A ring is:

[structures: pyrazole-carboxamide with $R_1$; thiazole-carboxamide; imidazole-carboxamide] or or a pharmaceutically acceptable salt thereof.

In a further embodiment, there is provided a compound of the formula (I) according to any of the embodiments hereinabove and wherein
A ring is:

[structure: pyrazole-carboxamide with $R_1$]

or a pharmaceutically acceptable salt thereof.

In a further embodiment, there is provided a compound of the formula (I) according to any of the embodiments hereinabove and wherein
A ring is:

[structure: thiazole-carboxamide]

or a pharmaceutically acceptable salt thereof.

In a further embodiment, there is provided a compound of the formula (I) according to any of the embodiments hereinabove and wherein
A ring is:

[structure: imidazole-carboxamide]

or a pharmaceutically acceptable salt thereof.

In a further embodiment, there is provided a compound of the formula (I) according to any of the embodiments hereinabove and wherein
$R_2$ is
L-Ar;
L is a linker chosen from a bond, O, and —O—$(CH_2)_n$—;
n is 1-3;
Ar is carbocycle or heterocycle;
or a pharmaceutically acceptable salt thereof.

In a further embodiment, there is provided a compound of the formula (I) according to any of the embodiments hereinabove and wherein
Ar is $C_{3-5}$ cycloalkyl or tetrahydrofuranyl;
n=1;
or a pharmaceutically acceptable salt thereof.

In a further embodiment, there is provided a compound of the formula (I) according to any of the embodiments hereinabove and wherein
L-Ar is

[structures: tetrahydrofuranyloxy, cyclopropylmethoxy, cyclopropyloxy, cyclopentyloxy] or or a pharmaceutically acceptable salt thereof.

In a further embodiment, there is provided a compound of the formula (I) according to any of the embodiments hereinabove and wherein R₂ is:
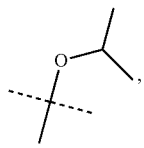
—OCH₂CH₃, —OCH₂CH₂CH₃, —OCH₃, —OCF₃ or —OCH₂CF₃;
or a pharmaceutically acceptable salt thereof.
In another embodiment, the invention provides made compounds in Table I which can be made in view of the general schemes, examples and methods known in the art.
TABLE of compounds and Biological activity
| Example | Structure | BTK IC50 (nM) | HPLC Method | RT (min) | m/z [M + H]⁺ |
|---|---|---|---|---|---|
| 1 | 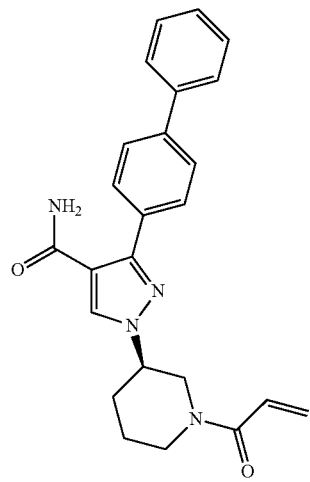 [SMILES: C=CC(=O)N1CCC[C@@H](n2cc(C(N)=O)c(-c3ccc(-c4ccccc4)cc3)n2)C1] | 2600 | A | 4.13 | 401.2 |
| 2 | 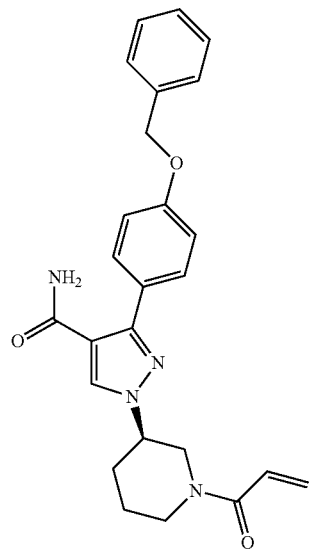 [SMILES: C=CC(=O)N1CCC[C@@H](n2cc(C(N)=O)c(-c3ccc(OCc4ccccc4)cc3)n2)C1] | 33 | A | 4.08 | 431.3 |

-continued

TABLE of compounds and Biological activity

| Example | Structure | BTK IC50 (nM) | HPLC Method | RT (min) | m/z [M + H]+ |
|---|---|---|---|---|---|
| 3 | 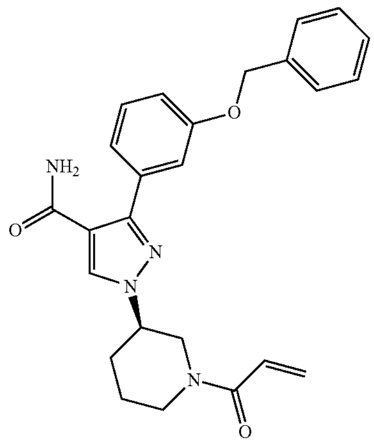 [SMILES: C=CC(=O)N1CCC[C@@H](n2cc(C(N)=O)c(-c3cccc(OCc4ccccc4)c3)n2)C1] | 810 | A | 4.06 | 431.3 |
| 4 | 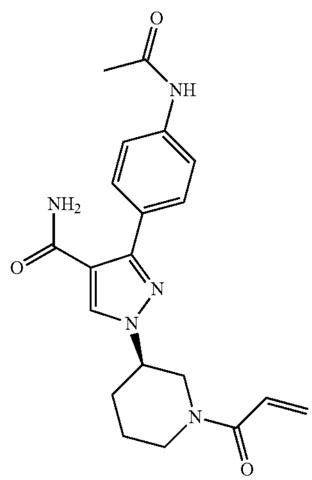 [SMILES: C=CC(=O)N1CCC[C@@H](n2cc(C(N)=O)c(-c3ccc(NC(C)=O)cc3)n2)C1] | — | A | 2.56 | 382.4 |
| 5 | 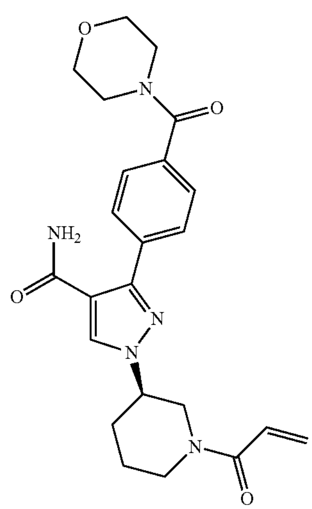 [SMILES: C=CC(=O)N1CCC[C@@H](n2cc(C(N)=O)c(-c3ccc(C(=O)N4CCOCC4)cc3)n2)C1] | — | A | 2.59 | 438.4 |

TABLE of compounds and Biological activity
| Example | Structure | BTK IC50 (nM) | HPLC Method | RT (min) | m/z [M + H]+ |
|---|---|---|---|---|---|
| 6 | 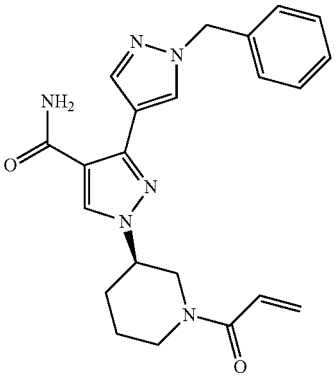 [SMILES: C=CC(=O)N1CCC[C@@H](n2cc(C(N)=O)c(-c3cnn(Cc4ccccc4)c3)n2)C1] | — | A | 2.75 | 405.4 |
| 7 | 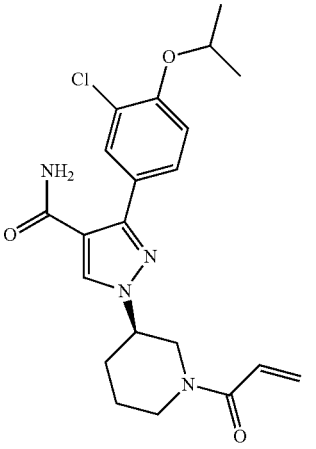 [SMILES: C=CC(=O)N1CCC[C@@H](n2cc(C(N)=O)c(-c3ccc(OC(C)C)c(Cl)c3)n2)C1] | — | A | 2.83 | 417.3 |
| 8 | 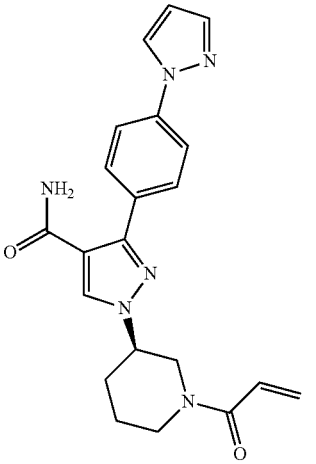 [SMILES: C=CC(=O)N1CCC[C@@H](n2cc(C(N)=O)c(-c3ccc(-n4cccn4)cc3)n2)C1] | — | A | 2.61 | 391.2 |

-continued

TABLE of compounds and Biological activity

| Example | Structure | BTK IC50 (nM) | HPLC Method | RT (min) | m/z [M + H]+ |
|---|---|---|---|---|---|
| 9 | 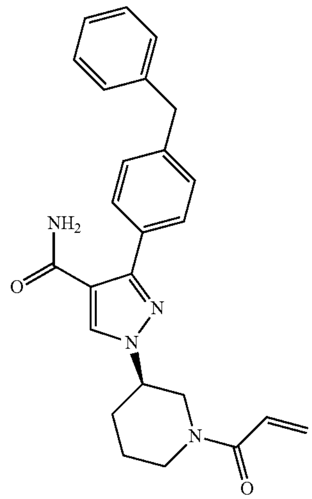 [SMILES: C=CC(=O)N1CCC[C@@H](n2cc(C(N)=O)c(-c3ccc(Cc4ccccc4)cc3)n2)C1] | 14 | A | 4.11 | 415.3 |
| 10 | 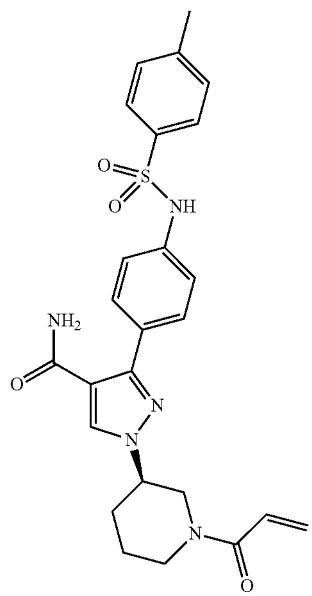 [SMILES: C=CC(=O)N1CCC[C@@H](n2cc(C(N)=O)c(-c3ccc(NS(=O)(=O)c4ccc(C)cc4)cc3)n2)C1] | — | A | 4.14 | 494.3 |
| 11 | 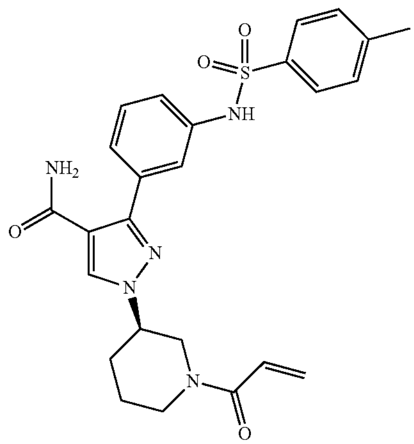 [SMILES: C=CC(=O)N1CCC[C@@H](n2cc(C(N)=O)c(-c3cccc(NS(=O)(=O)c4ccc(C)cc4)c3)n2)C1] | 5500 | A | 2.80 | 494.2 |

-continued

TABLE of compounds and Biological activity

| Example | Structure | BTK IC50 (nM) | HPLC Method | RT (min) | m/z [M + H]+ |
|---|---|---|---|---|---|
| 12 | 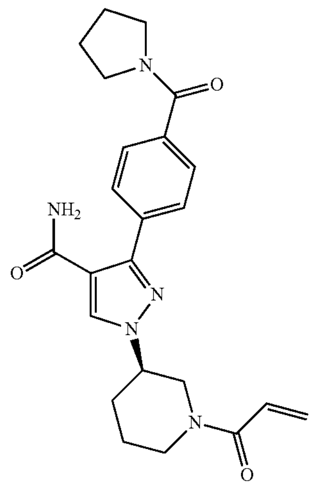 [SMILES: C=CC(=O)N1CCC[C@@H](n2cc(C(N)=O)c(-c3ccc(C(=O)N4CCCC4)cc3)n2)C1] | — | A | 2.67 | 422.3 |
| 13 | 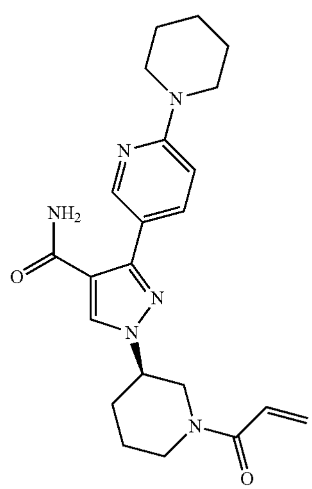 [SMILES: C=CC(=O)N1CCC[C@@H](n2cc(C(N)=O)c(-c3ccc(N4CCCCC4)nc3)n2)C1] | — | A | 2.56 | 409.3 |
| 14 | 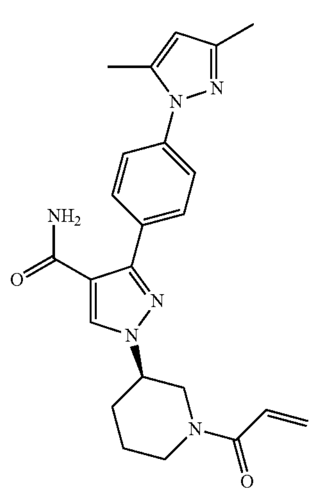 [SMILES: C=CC(=O)N1CCC[C@@H](n2cc(C(N)=O)c(-c3ccc(-n4nc(C)cc4C)cc3)n2)C1] | 7800 | A | 2.81 | 419.4 |

-continued

TABLE of compounds and Biological activity

| Example | Structure | BTK IC50 (nM) | HPLC Method | RT (min) | m/z [M + H]+ |
|---|---|---|---|---|---|
| 15 | 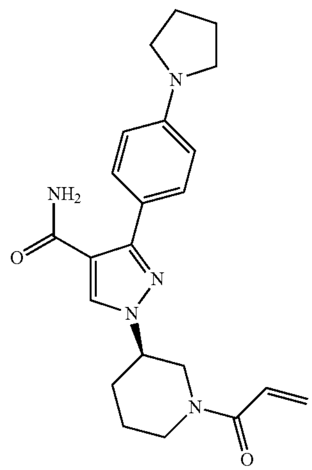 [SMILES: C=CC(=O)N1CCC[C@@H](n2cc(C(N)=O)c(-c3ccc(N4CCCC4)cc3)n2)C1] | — | A | 2.89 | 394.4 |
| 16 | 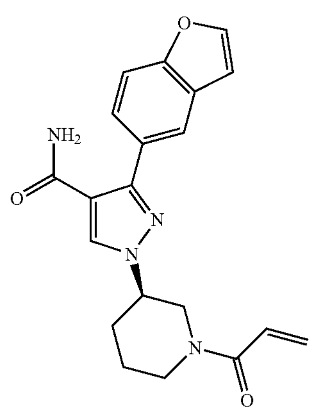 [SMILES: C=CC(=O)N1CCC[C@@H](n2cc(C(N)=O)c(-c3ccc4occc4c3)n2)C1] | 580 | A | 2.77 | 365.3 |
| 17 | 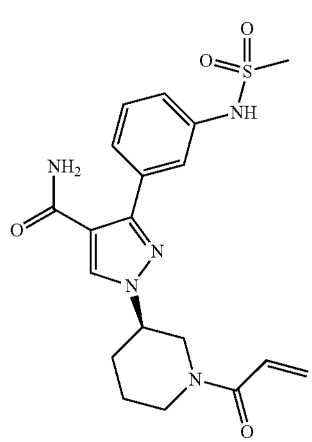 [SMILES: C=CC(=O)N1CCC[C@@H](n2cc(C(N)=O)c(-c3cccc(NS(C)(=O)=O)c3)n2)C1] | 4800 | A | 2.60 | 418.4 |

TABLE of compounds and Biological activity
| Example | Structure | BTK IC50 (nM) | HPLC Method | RT (min) | m/z [M + H]+ |
|---|---|---|---|---|---|
| 18 | 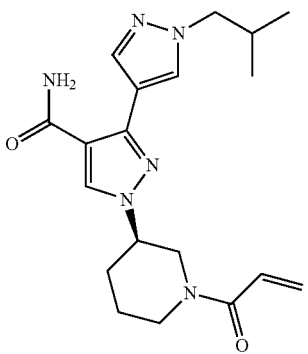 [SMILES: C=CC(=O)N1CCC[C@@H](n2cc(C(N)=O)c(-c3cnn(CC(C)C)c3)n2)C1] | — | A | 2.72 | 371.4 |
| 19 | 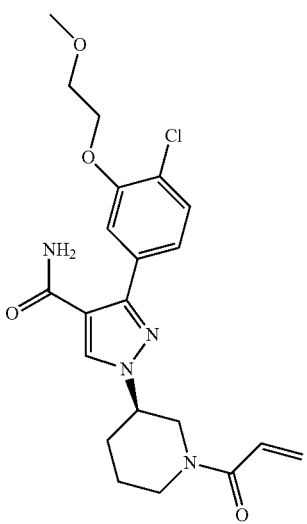 [SMILES: C=CC(=O)N1CCC[C@@H](n2cc(C(N)=O)c(-c3ccc(Cl)c(OCCOC)c3)n2)C1] | — | A | 2.84 | 433.3 |
| 20 | 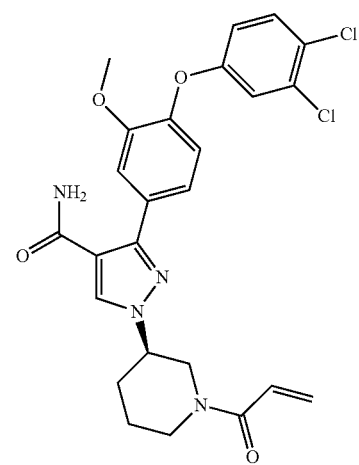 [SMILES: C=CC(=O)N1CCC[C@@H](n2cc(C(N)=O)c(-c3ccc(Oc4ccc(Cl)c(Cl)c4)c(OC)c3)n2)C1] | 30 | A | 3.03 | 515.2 |

-continued
TABLE of compounds and Biological activity
| Example | Structure | BTK IC50 (nM) | HPLC Method | RT (min) | m/z [M + H]+ |
|---|---|---|---|---|---|
| 21 | 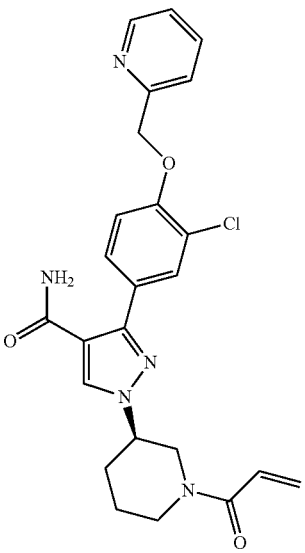 [SMILES: C=CC(=O)N1CCC[C@@H](n2cc(C(N)=O)c(-c3ccc(OCc4ccccn4)c(Cl)c3)n2)C1] | 98 | A | 2.85 | 466.3 |
| 22 | 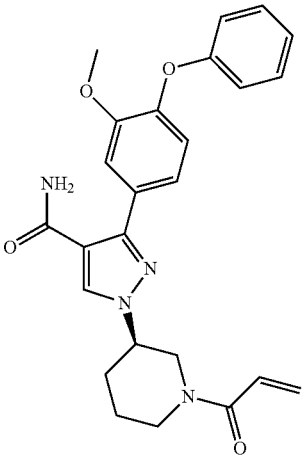 [SMILES: C=CC(=O)N1CCC[C@@H](n2cc(C(N)=O)c(-c3ccc(Oc4ccccc4)c(OC)c3)n2)C1] | 7.6 | A | 2.91 | 447.3 |
| 23 | 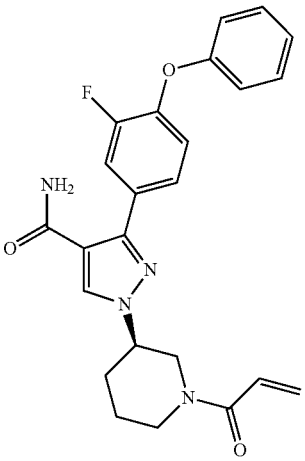 [SMILES: C=CC(=O)N1CCC[C@@H](n2cc(C(N)=O)c(-c3ccc(Oc4ccccc4)c(F)c3)n2)C1] | 10 | A | 2.97 | 435.3 |

TABLE of compounds and Biological activity
| Example | Structure | BTK IC50 (nM) | HPLC Method | RT (min) | m/z [M + H]+ |
|---------|-----------|---------------|-------------|----------|--------------|
| 24 | 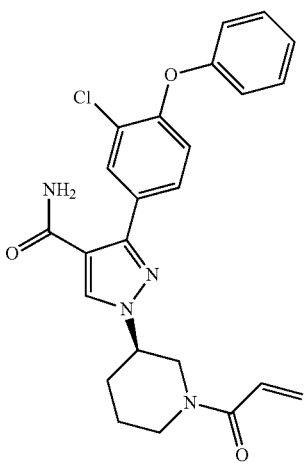 [SMILES: C=CC(=O)N1CCC[C@@H](n2cc(C(N)=O)c(-c3ccc(Oc4ccccc4)c(Cl)c3)n2)C1] | 9.4 | A | 3.02 | 451.3 |
| 25 | 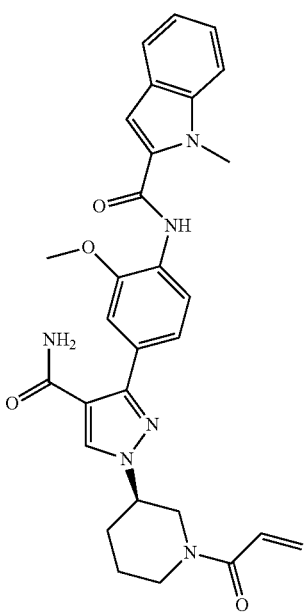 [SMILES: C=CC(=O)N1CCC[C@@H](n2cc(C(N)=O)c(-c3ccc(NC(=O)c4cc5ccccc5n4C)c(OC)c3)n2)C1] | 5.1 | A | 3.03 | 527.3 |

TABLE of compounds and Biological activity
| Example | Structure | BTK IC50 (nM) | HPLC Method | RT (min) | m/z [M + H]+ |
|---|---|---|---|---|---|
| 26 | 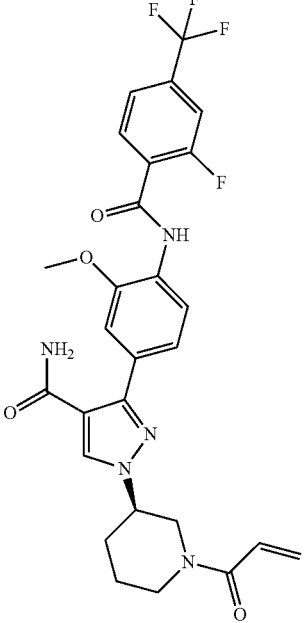 | 22 | A | 3.03 | 560.3 |
| 27 | 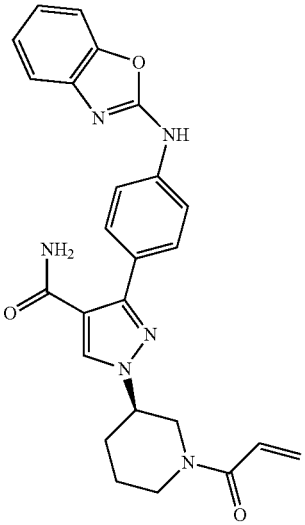 [SMILES: C=CC(=O)N1CCC[C@@H](n2cc(C(N)=O)c(-c3ccc(Nc4nc5ccccc5o4)cc3)n2)C1] | 300 | A | 2.84 | 457.3 |

-continued

TABLE of compounds and Biological activity

| Example | Structure | BTK IC50 (nM) | HPLC Method | RT (min) | m/z [M + H]+ |
|---|---|---|---|---|---|
| 28 | 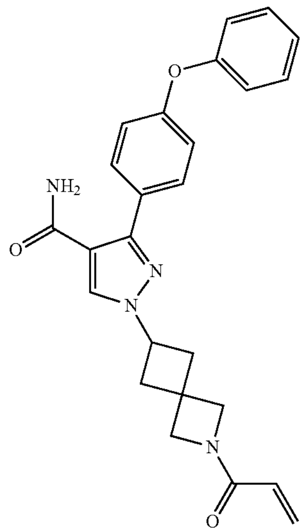 [SMILES: C=CC(=O)N1CC2(CC(n3cc(C(N)=O)c(-c4ccc(Oc5ccccc5)cc4)n3)C2)C1] | 3.5 | A | 2.85 | 429.3 |
| 29 | 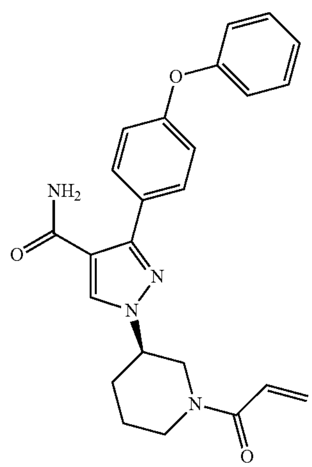 [SMILES: C=CC(=O)N1CCC[C@@H](n2cc(C(N)=O)c(-c3ccc(Oc4ccccc4)cc3)n2)C1] | 3.2 | A | 2.83 | 417.3 |
| 30 | 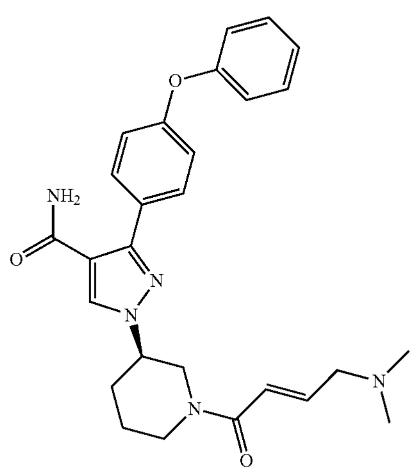 [SMILES: CN(C)C/C=C/C(=O)N1CCC[C@@H](n2cc(C(N)=O)c(-c3ccc(Oc4ccccc4)cc3)n2)C1] | 57 | A | 2.54 | 474.35 |

-continued

TABLE of compounds and Biological activity

| Example | Structure | BTK IC50 (nM) | HPLC Method | RT (min) | m/z [M + H]+ |
|---|---|---|---|---|---|
| 31 | 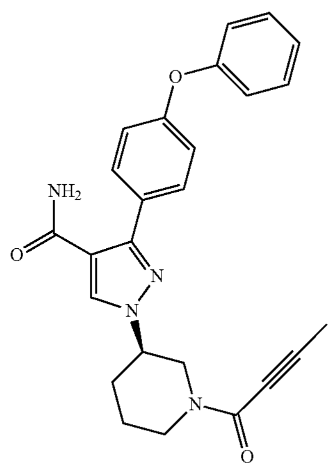 [SMILES: CC#CC(=O)N1CCC[C@@H](n2cc(C(N)=O)c(-c3ccc(Oc4ccccc4)cc3)n2)C1] | 80 | A | 2.86 | 429.35 |
| 32 | 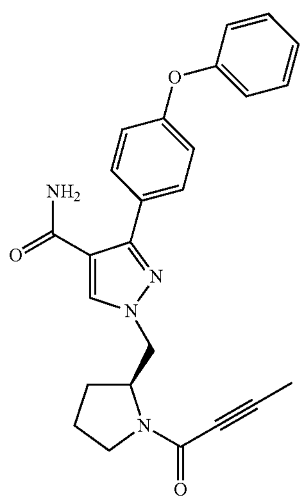 [SMILES: CC#CC(=O)N1CCC[C@H]1Cn1cc(C(N)=O)c(-c2ccc(Oc3ccccc3)cc2)n1] | 150 | A | 2.81 | 429.35 |
| 33 | 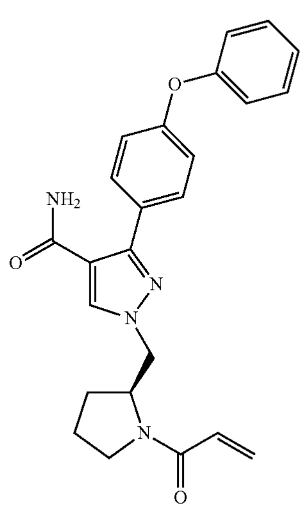 [SMILES: C=CC(=O)N1CCC[C@H]1Cn1cc(C(N)=O)c(-c2ccc(Oc3ccccc3)cc2)n1] | 9.7 | A | 2.83 | 417.35 |

-continued

TABLE of compounds and Biological activity

| Example | Structure | BTK IC50 (nM) | HPLC Method | RT (min) | m/z [M + H]+ |
|---|---|---|---|---|---|
| 34 | 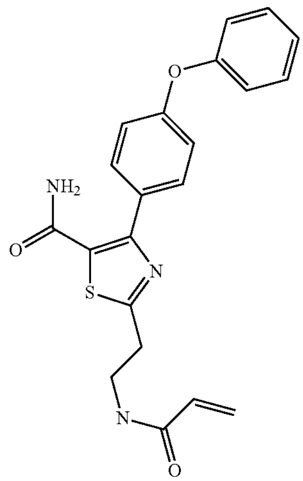 [SMILES: C=CC(=O)NCCc1nc(-c2ccc(Oc3ccccc3)cc2)c(C(N)=O)s1] | 21 | A | 2.78 | 394.35 |
| 35 | 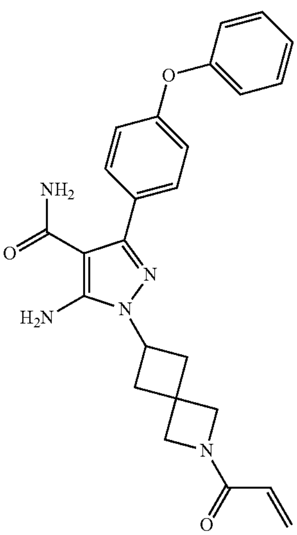 [SMILES: C=CC(=O)N1CC2(CC(n3nc(-c4ccc(Oc5ccccc5)cc4)c(C(N)=O)c3N)C2)C1] | 0.77 | A | 2.96 | 444.3 |
| 36 | 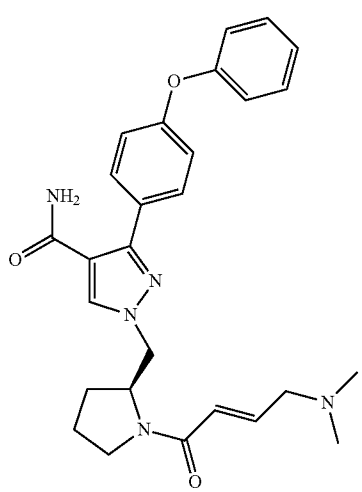 [SMILES: CN(C)C/C=C/C(=O)N1CCC[C@H]1Cn1cc(C(N)=O)c(-c2ccc(Oc3ccccc3)cc2)n1] | 230 | A | 2.67 | 474.3 |

TABLE of compounds and Biological activity

| Example | Structure | BTK IC50 (nM) | HPLC Method | RT (min) | m/z [M + H]+ |
|---------|-----------|---------------|-------------|----------|--------------|
| 37 | 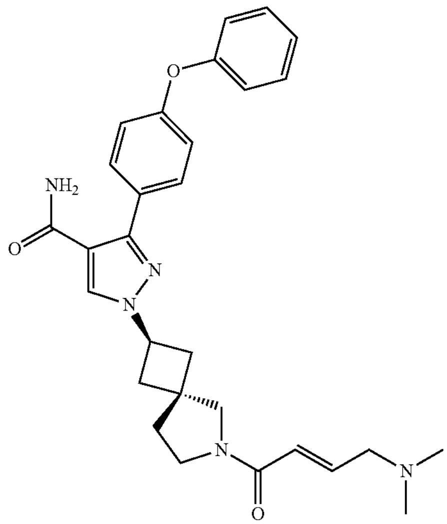 [SMILES: CN(C)C/C=C/C(=O)N1CC[C@]2(C1)C[C@H](n1cc(C(N)=O)c(-c3ccc(Oc4ccccc4)cc3)n1)C2] | 38 | A | 2.51 | 500.3 |
| 38 | 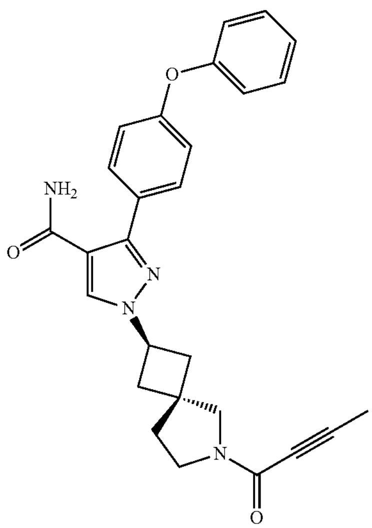 [SMILES: CC#CC(=O)N1CC[C@]2(C1)C[C@H](n1cc(C(N)=O)c(-c3ccc(Oc4ccccc4)cc3)n1)C2] | 13 | A | 2.84 | 455.3 |
| 39 | 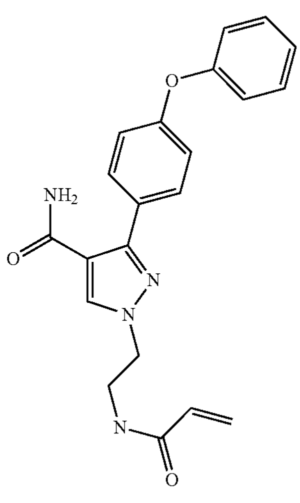 [SMILES: C=CC(=O)NCCn1cc(C(N)=O)c(-c2ccc(Oc3ccccc3)cc2)n1] | 290 | A | 2.65 | 377.2 |

-continued
TABLE of compounds and Biological activity
| Example | Structure | BTK IC50 (nM) | HPLC Method | RT (min) | m/z [M + H]+ |
|---|---|---|---|---|---|
| 40 | 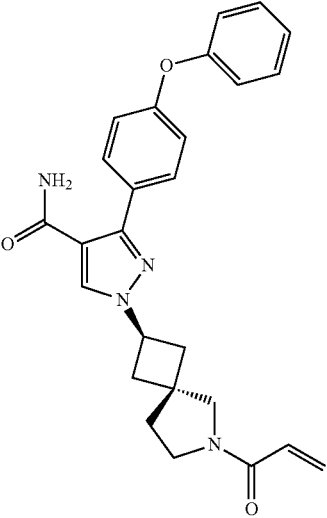 [SMILES: C=CC(=O)N1CC[C@]2(C1)C[C@H](n1cc(C(N)=O)c(-c3ccc(Oc4ccccc4)cc3)n1)C2] | 4.9 | A | 2.89 | 443.2 |
| 41 | 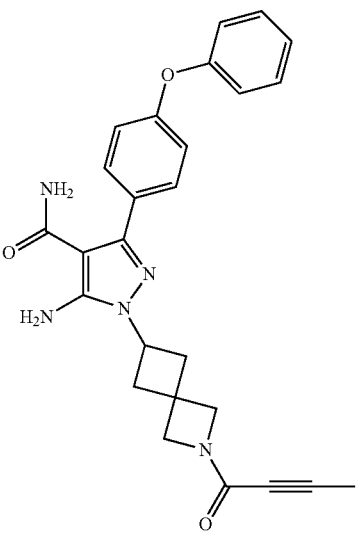 [SMILES: CC#CC(=O)N1CC2(CC(n3nc(-c4ccc(Oc5ccccc5)cc4)c(C(N)=O)c3N)C2)C1] | 0.73 | A | 2.99 | 456.3 |
| 42 | 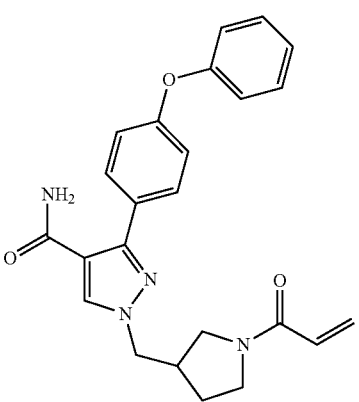 [SMILES: C=CC(=O)N1CCC(Cn2cc(C(N)=O)c(-c3ccc(Oc4ccccc4)cc3)n2)C1] | 64 | A | 2.92 | 417.4 |

-continued

TABLE of compounds and Biological activity

| Example | Structure | BTK IC50 (nM) | HPLC Method | RT (min) | m/z [M + H]+ |
|---|---|---|---|---|---|
| 43 | 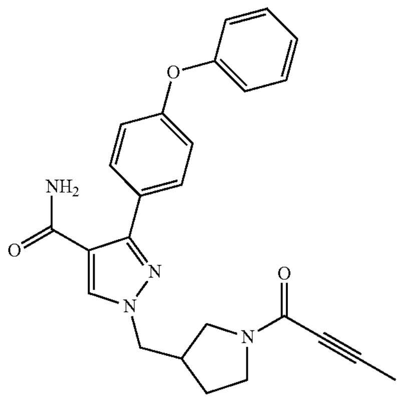 [SMILES: CC#CC(=O)N1CCC(Cn2cc(C(N)=O)c(-c3ccc(Oc4ccccc4)cc3)n2)C1] | 51 | A | 2.93 | 429.4 |
| 44 | 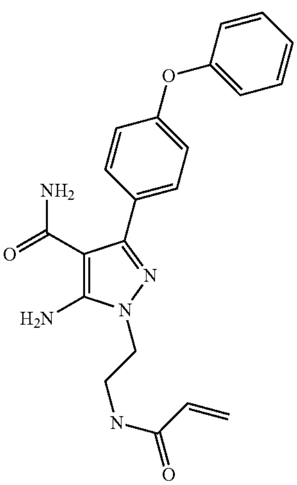 [SMILES: C=CC(=O)NCCn1nc(-c2ccc(Oc3ccccc3)cc2)c(C(N)=O)c1N] | 1 | A | 2.68 | 392.4 |
| 45 | 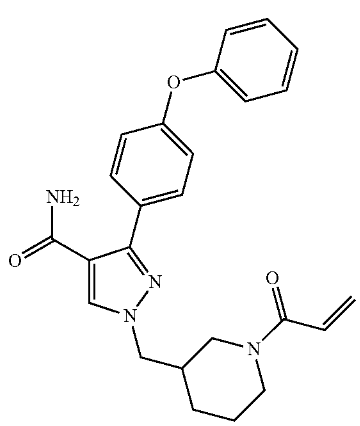 [SMILES: C=CC(=O)N1CCCC(Cn2cc(C(N)=O)c(-c3ccc(Oc4ccccc4)cc3)n2)C1] | 10 | A | 2.83 | 431.4 |

TABLE of compounds and Biological activity

| Example | Structure | BTK IC50 (nM) | HPLC Method | RT (min) | m/z [M + H]+ |
|---|---|---|---|---|---|
| 46 | 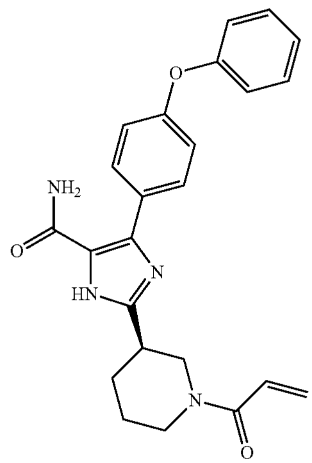 [SMILES: C=CC(=O)N1CCC[C@@H](c2nc(-c3ccc(Oc4ccccc4)cc3)c(C(N)=O)[nH]2)C1] | 1.2 | A | 2.85 | 417.4 |
| 47 | 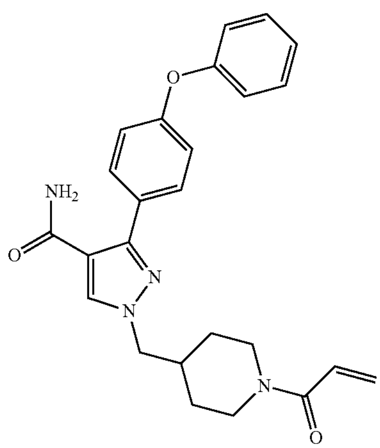 [SMILES: C=CC(=O)N1CCC(Cn2cc(C(N)=O)c(-c3ccc(Oc4ccccc4)cc3)n2)CC1] | 10 | A | 2.84 | 431.4 |
| 48 | 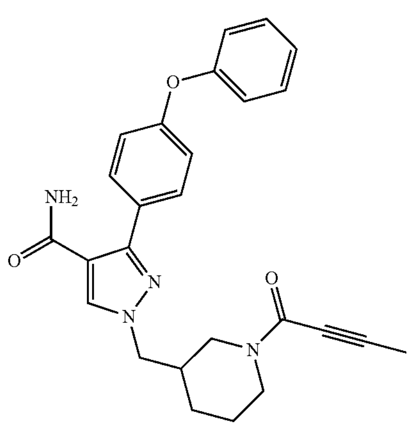 [SMILES: CC#CC(=O)N1CCCC(Cn2cc(C(N)=O)c(-c3ccc(Oc4ccccc4)cc3)n2)C1] | 90 | A | 2.97 | 443.4 |

-continued

TABLE of compounds and Biological activity

| Example | Structure | BTK IC50 (nM) | HPLC Method | RT (min) | m/z [M + H]+ |
|---|---|---|---|---|---|
| 49 | 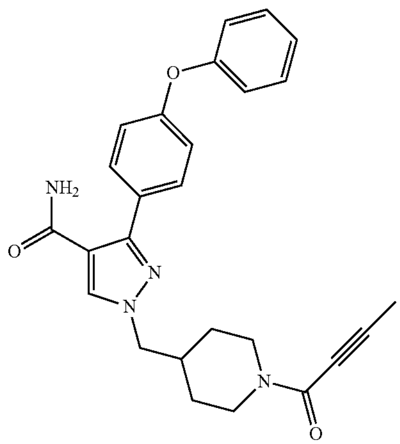 [SMILES: CC#CC(=O)N1CCC(Cn2cc(C(N)=O)c(-c3ccc(Oc4ccccc4)cc3)n2)CC1] | 180 | A | 2.96 | 443.4 |
| 50 | 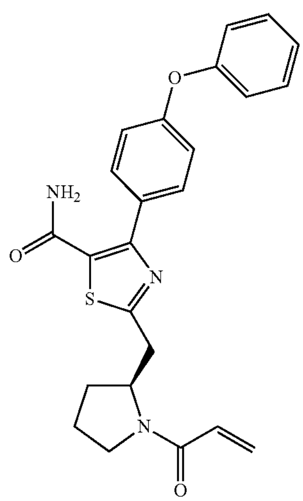 [SMILES: C=CC(=O)N1CCC[C@H]1Cc1nc(-c2ccc(Oc3ccccc3)cc2)c(C(N)=O)s1] | 3 | A | 2.98 | 434.3 |
| 51 | 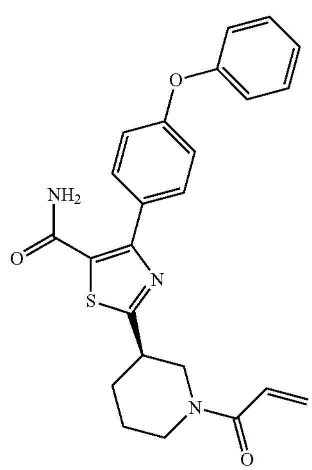 [SMILES: C=CC(=O)N1CCC[C@@H](c2nc(-c3ccc(Oc4ccccc4)cc3)c(C(N)=O)s2)C1] | 1.7 | A | 3.00 | 434.3 |

-continued

TABLE of compounds and Biological activity

| Example | Structure | BTK IC50 (nM) | HPLC Method | RT (min) | m/z [M + H]+ |
|---|---|---|---|---|---|
| 52 | 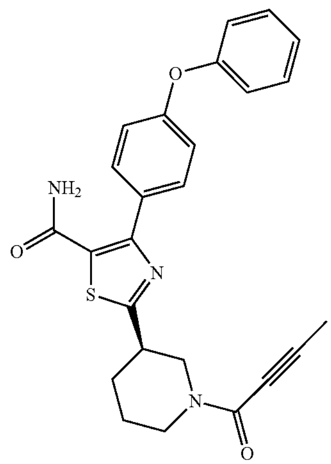 [SMILES: CC#CC(=O)N1CCC[C@@H](c2nc(-c3ccc(Oc4ccccc4)cc3)c(C(N)=O)s2)C1] | 18 | A | 3.02 | 446.3 |
| 53 | 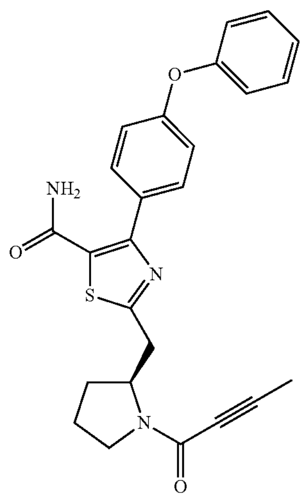 [SMILES: CC#CC(=O)N1CCC[C@H]1Cc1nc(-c2ccc(Oc3ccccc3)cc2)c(C(N)=O)s1] | 14 | A | 3.00 | 446.3 |
| 54 | 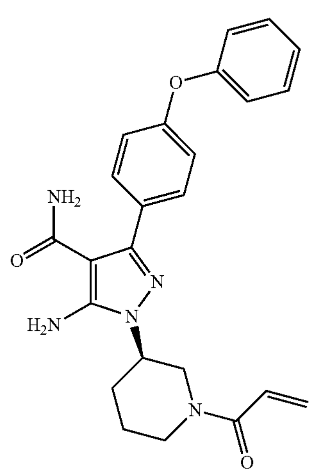 [SMILES: C=CC(=O)N1CCC[C@@H](n2nc(-c3ccc(Oc4ccccc4)cc3)c(C(N)=O)c2N)C1] | 0.73 | A | 3.00 | 432.4 |

-continued
TABLE of compounds and Biological activity
| Example | Structure | BTK IC50 (nM) | HPLC Method | RT (min) | m/z [M + H]+ |
|---|---|---|---|---|---|
| 55 | 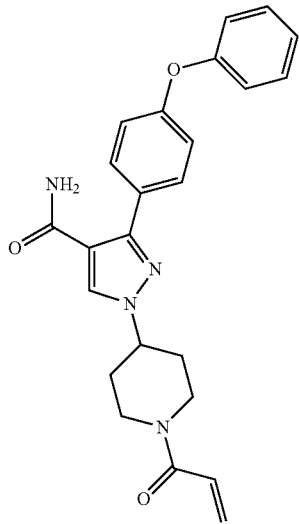 [SMILES: C=CC(=O)N1CCC(n2cc(C(N)=O)c(-c3ccc(Oc4ccccc4)cc3)n2)CC1] | 6.6 | A | 2.93 | 417.4 |
| 56 | 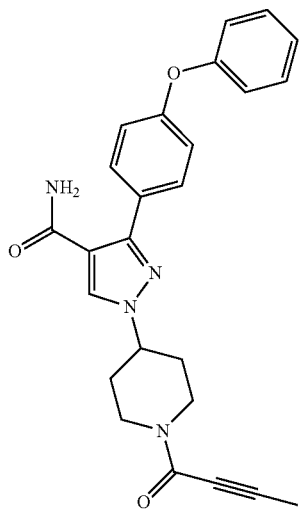 [SMILES: CC#CC(=O)N1CCC(n2cc(C(N)=O)c(-c3ccc(Oc4ccccc4)cc3)n2)CC1] | 15 | A | 2.95 | 429.4 |

TABLE of compounds and Biological activity
| Example | Structure | BTK IC50 (nM) | HPLC Method | RT (min) | m/z [M + H]+ |
|---|---|---|---|---|---|
| 57 | 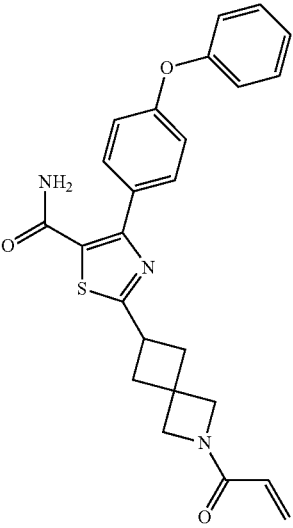 [SMILES: C=CC(=O)N1CC2(CC(c3nc(-c4ccc(Oc5ccccc5)cc4)c(C(N)=O)s3)C2)C1] | 3.2 | A | 2.99 | 446.3 |
| 58 | 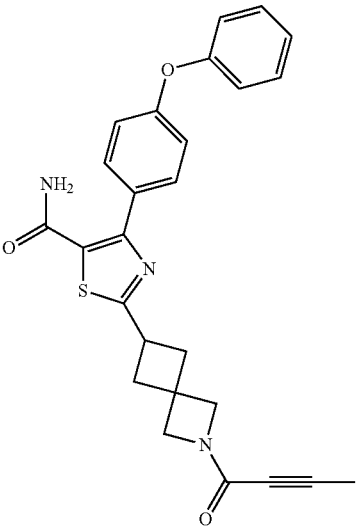 [SMILES: CC#CC(=O)N1CC2(CC(c3nc(-c4ccc(Oc5ccccc5)cc4)c(C(N)=O)s3)C2)C1] | 1.1 | A | 3.01 | 458.3 |
| 59 | 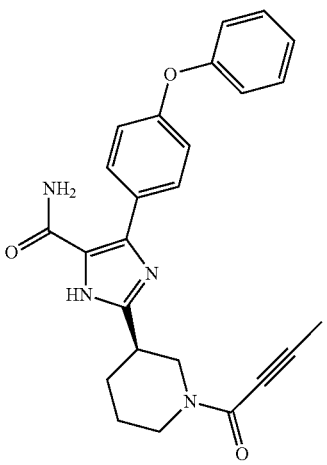 [SMILES: CC#CC(=O)N1CCC[C@@H](c2nc(-c3ccc(Oc4ccccc4)cc3)c(C(N)=O)[nH]2)C1] | 8.9 | A | 2.75 | 429.4 |

-continued

TABLE of compounds and Biological activity

| Example | Structure | BTK IC50 (nM) | HPLC Method | RT (min) | m/z [M + H]+ |
|---|---|---|---|---|---|
| 60 | 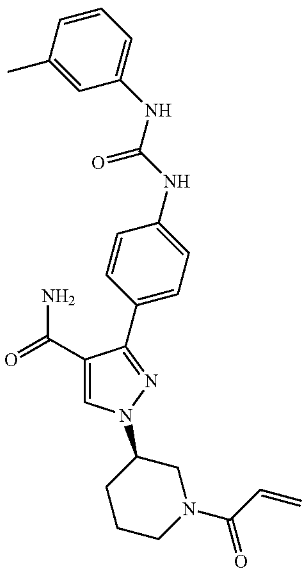 [SMILES: C=CC(=O)N1CCC[C@@H](n2cc(C(N)=O)c(-c3ccc(NC(=O)Nc4cccc(C)c4)cc3)n2)C1] | 41 | A | 2.82 | 473.4 |
| 61 | 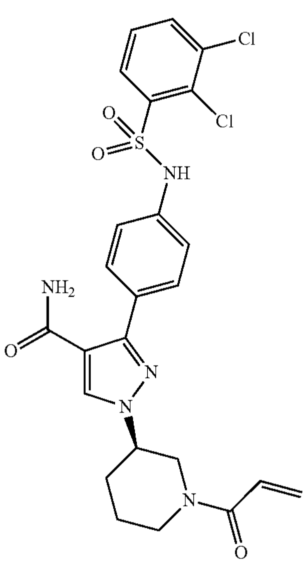 [SMILES: C=CC(=O)N1CCC[C@@H](n2cc(C(N)=O)c(-c3ccc(NS(=O)(=O)c4cccc(Cl)c4Cl)cc3)n2)C1] | 780 | A | 2.86 | 548.1 |

TABLE of compounds and Biological activity
| Example | Structure | BTK IC50 (nM) | HPLC Method | RT (min) | m/z [M + H]+ |
|---|---|---|---|---|---|
| 62 | 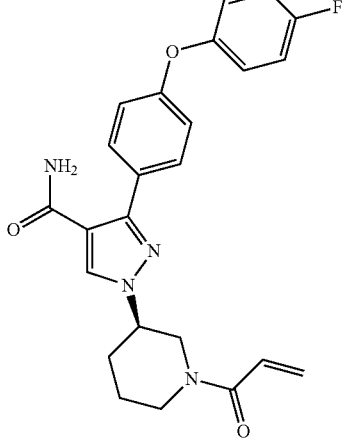 | 93 | A | 2.97 | 435.3 |
| 63 | 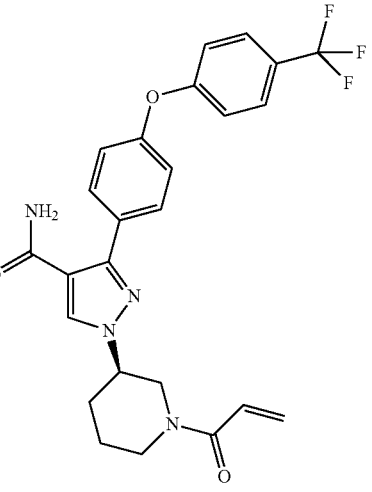 | 660 | A | 3.08 | 485.3 |
| 64 | 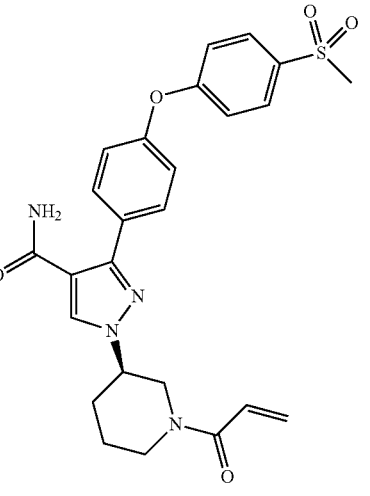 | 6500 | A | 2.79 | 495.1 |

-continued

TABLE of compounds and Biological activity

| Example | Structure | BTK IC50 (nM) | HPLC Method | RT (min) | m/z [M + H]+ |
|---|---|---|---|---|---|
| 65 | 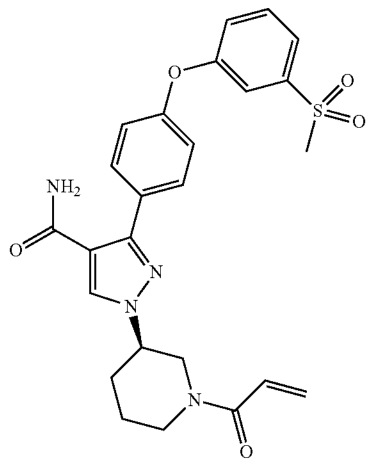 [SMILES: C=CC(=O)N1CCC[C@@H](n2cc(C(N)=O)c(-c3ccc(Oc4cccc(S(C)(=O)=O)c4)cc3)n2)C1] | 330 | B | 0.65 | 495.1 |
| 66 | 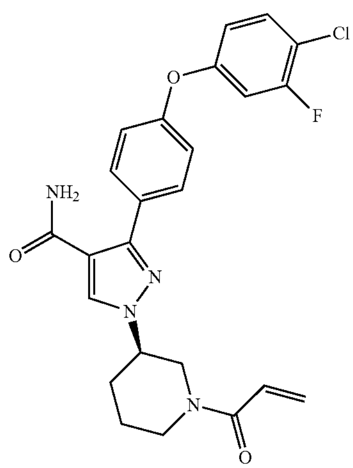 [SMILES: C=CC(=O)N1CCC[C@@H](n2cc(C(N)=O)c(-c3ccc(Oc4ccc(Cl)c(F)c4)cc3)n2)C1] | 43 | A | 3.10 | 469.2 |
| 67 | 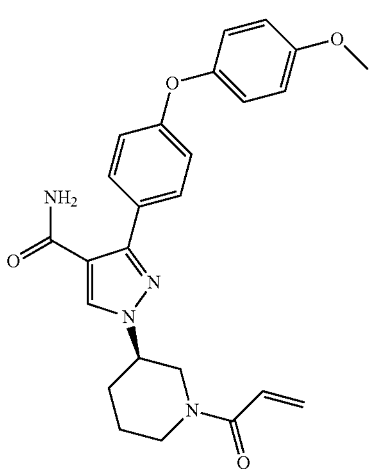 [SMILES: C=CC(=O)N1CCC[C@@H](n2cc(C(N)=O)c(-c3ccc(Oc4ccc(OC)cc4)cc3)n2)C1] | 38 | A | 2.95 | 447.3 |

-continued
TABLE of compounds and Biological activity
| Example | Structure | BTK IC50 (nM) | HPLC Method | RT (min) | m/z [M + H]+ |
|---|---|---|---|---|---|
| 68 | 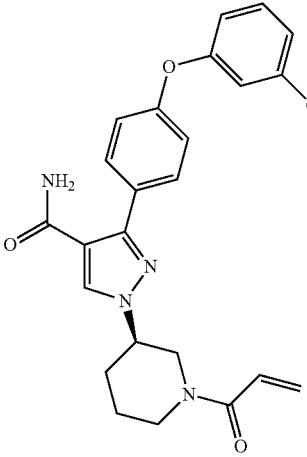 | 41 | A | 3.08 | 451.4 |
| 69 | 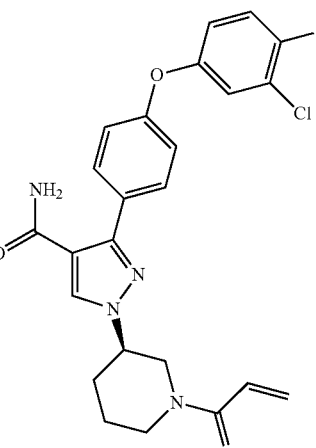 | 43 | A | 3.20 | 485.3 |
| 70 | 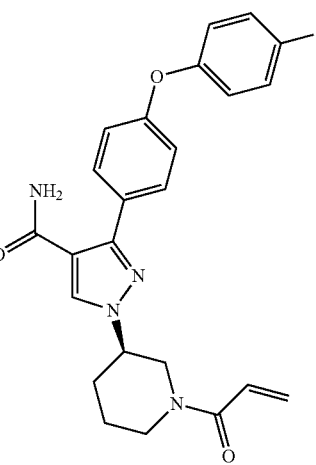 | 45 | A | 3.07 | 451.3 |

-continued

TABLE of compounds and Biological activity

| Example | Structure | BTK IC50 (nM) | HPLC Method | RT (min) | m/z [M + H]+ |
|---|---|---|---|---|---|
| 71 | 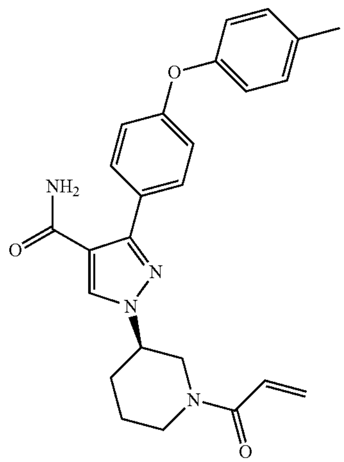 [SMILES: C=CC(=O)N1CCC[C@@H](n2cc(C(N)=O)c(-c3ccc(Oc4ccc(C)cc4)cc3)n2)C1] | 14 | A | 3.04 | 431.4 |
| 72 | 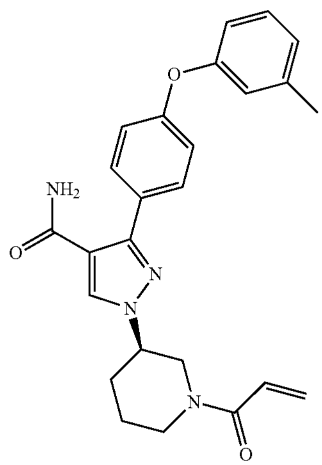 [SMILES: C=CC(=O)N1CCC[C@@H](n2cc(C(N)=O)c(-c3ccc(Oc4cccc(C)c4)cc3)n2)C1] | 4 | A | 3.04 | 431.4 |
| 73 | 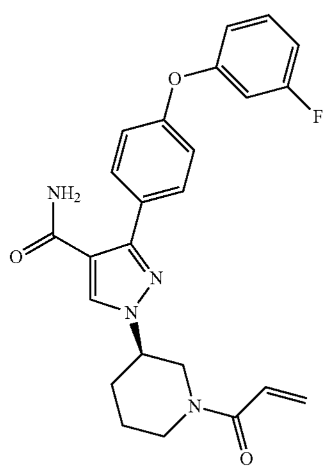 [SMILES: C=CC(=O)N1CCC[C@@H](n2cc(C(N)=O)c(-c3ccc(Oc4cccc(F)c4)cc3)n2)C1] | 9.3 | A | 3.00 | 435.3 |

TABLE of compounds and Biological activity

| Example | Structure | BTK IC50 (nM) | HPLC Method | RT (min) | m/z [M + H]+ |
|---|---|---|---|---|---|
| 74 | 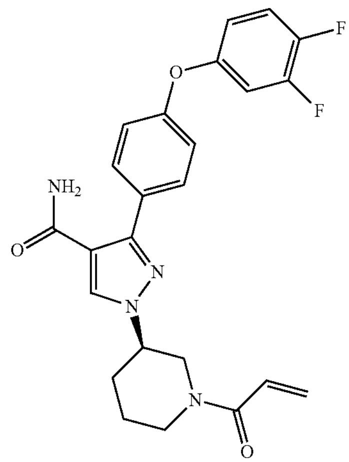 [SMILES: C=CC(=O)N1CCC[C@@H](n2cc(C(N)=O)c(-c3ccc(Oc4ccc(F)c(F)c4)cc3)n2)C1] | — | A | 2.89 | 453.3 |
| 75 | 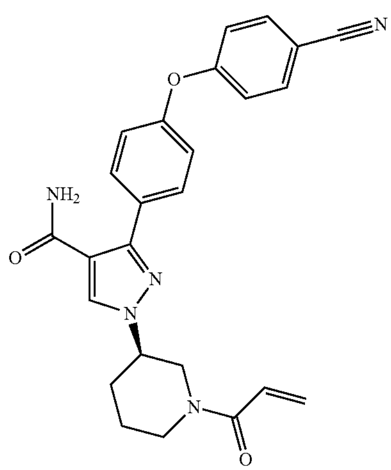 [SMILES: C=CC(=O)N1CCC[C@@H](n2cc(C(N)=O)c(-c3ccc(Oc4ccc(C#N)cc4)cc3)n2)C1] | 6600 | A | 2.91 | 442.3 |
| 76 | 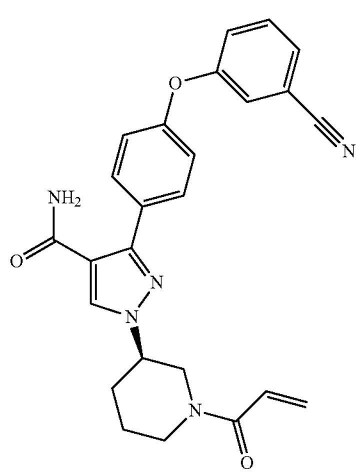 [SMILES: C=CC(=O)N1CCC[C@@H](n2cc(C(N)=O)c(-c3ccc(Oc4cccc(C#N)c4)cc3)n2)C1] | 61 | A | 2.92 | 442.4 |

TABLE of compounds and Biological activity

| Example | Structure | BTK IC50 (nM) | HPLC Method | RT (min) | m/z [M + H]+ |
|---------|-----------|---------------|-------------|----------|--------------|
| 77 | 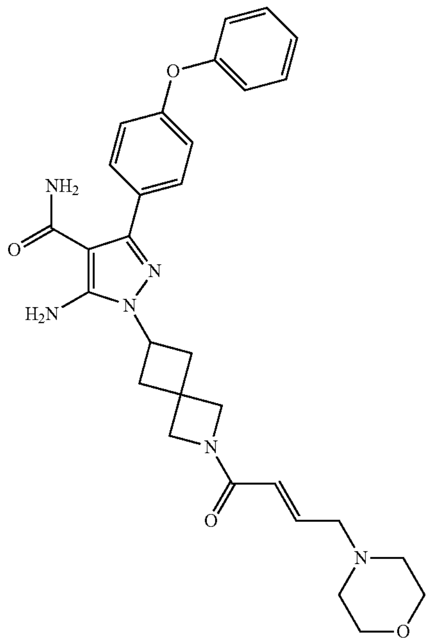 [SMILES: NC(=O)c1c(-c2ccc(Oc3ccccc3)cc2)nn(C2CC3(C2)CN(C(=O)/C=C/CN2CCOCC2)C3)c1N] | 1.9 | A | 2.72 | 543.3 |
| 78 | 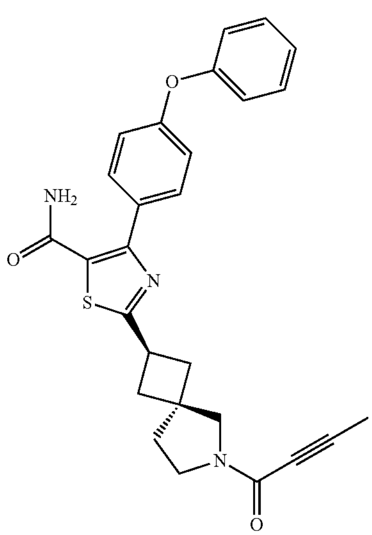 [SMILES: CC#CC(=O)N1CC[C@]2(C1)C[C@@H](c1nc(-c3ccc(Oc4ccccc4)cc3)c(C(N)=O)s1)C2] | 2.1 | A | 2.95 | 472.2 |

TABLE of compounds and Biological activity
| Example | Structure | BTK IC50 (nM) | HPLC Method | RT (min) | m/z [M + H]+ |
|---|---|---|---|---|---|
| 79 | 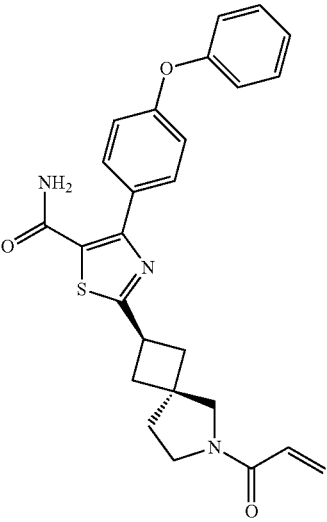 [SMILES: C=CC(=O)N1CC[C@]2(C1)C[C@@H](c1nc(-c3ccc(Oc4ccccc4)cc3)c(C(N)=O)s1)C2] | 6.4 | A | 3.05 | 460.2 |
| 80 | 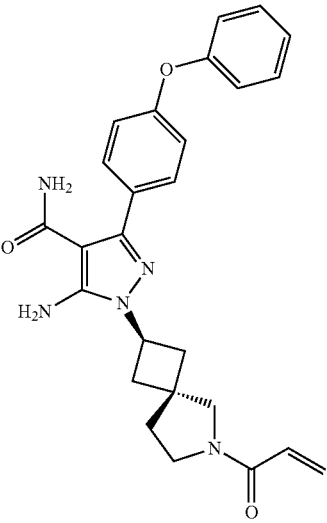 [SMILES: C=CC(=O)N1CC[C@]2(C1)C[C@H](n1nc(-c3ccc(Oc4ccccc4)cc3)c(C(N)=O)c1N)C2] | 0.93 | A | 3.04 | 458.4 |

-continued

TABLE of compounds and Biological activity

| Example | Structure | BTK IC50 (nM) | HPLC Method | RT (min) | m/z [M + H]+ |
|---------|-----------|---------------|-------------|----------|--------------|
| 81 | 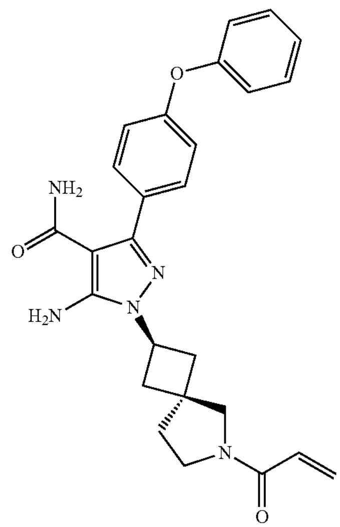 [SMILES: C=CC(=O)N1CC[C@]2(C1)C[C@@H](n1nc(-c3ccc(Oc4ccccc4)cc3)c(C(N)=O)c1N)C2] | 0.79 | A | 2.91 | 458.3 |
| 82 | 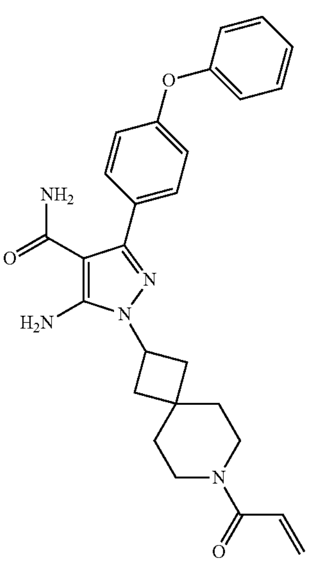 [SMILES: C=CC(=O)N1CCC2(CC1)CC(n1nc(-c3ccc(Oc4ccccc4)cc3)c(C(N)=O)c1N)C2] | 2 | A | 2.95 | 472.2 |

-continued

TABLE of compounds and Biological activity

| Example | Structure | BTK IC50 (nM) | HPLC Method | RT (min) | m/z [M + H]+ |
|---|---|---|---|---|---|
| 83 | 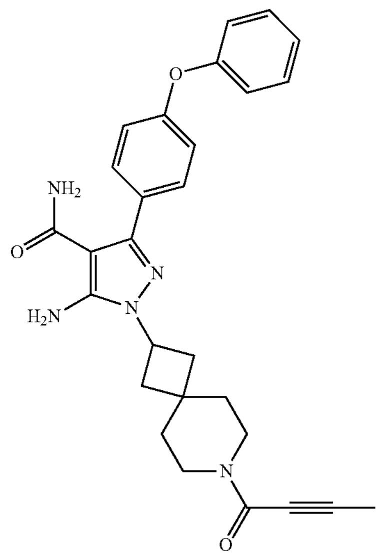 [SMILES: CC#CC(=O)N1CCC2(CC1)CC(n1nc(-c3ccc(Oc4ccccc4)cc3)c(C(N)=O)c1N)C2] | 2.1 | A | 2.99 | 484.3 |
| 84 | 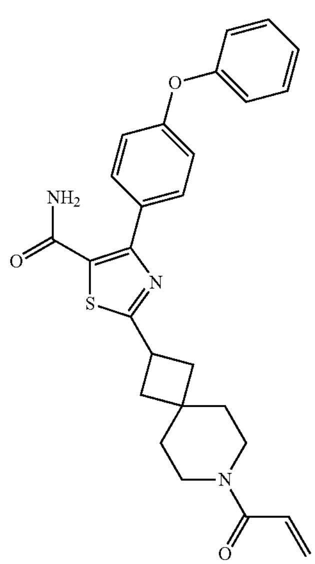 [SMILES: C=CC(=O)N1CCC2(CC1)CC(c1nc(-c3ccc(Oc4ccccc4)cc3)c(C(N)=O)s1)C2] | 52 | A | 3.10 | 474.2 |

-continued

TABLE of compounds and Biological activity

| Example | Structure | BTK IC50 (nM) | HPLC Method | RT (min) | m/z [M + H]+ |
|---|---|---|---|---|---|
| 85 | 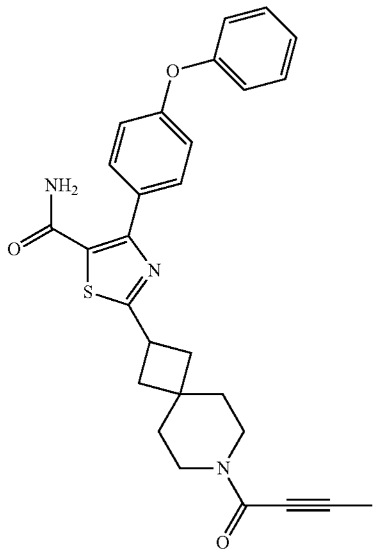 [SMILES: CC#CC(=O)N1CCC2(CC1)CC(c1nc(-c3ccc(Oc4ccccc4)cc3)c(C(N)=O)s1)C2] | 300 | A | 3.11 | 486.2 |
| 86 | 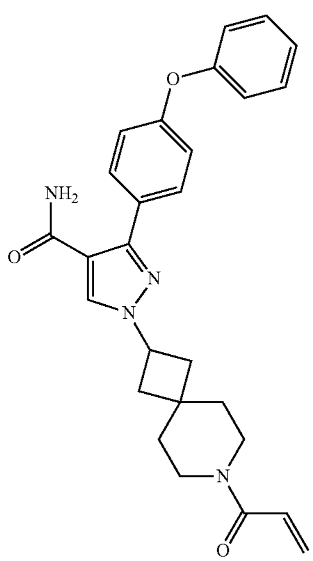 [SMILES: C=CC(=O)N1CCC2(CC1)CC(n1cc(C(N)=O)c(-c3ccc(Oc4ccccc4)cc3)n1)C2] | 95 | A | 3.03 | 457.4 |

-continued

TABLE of compounds and Biological activity

| Example | Structure | BTK IC50 (nM) | HPLC Method | RT (min) | m/z [M + H]+ |
|---|---|---|---|---|---|
| 87 | 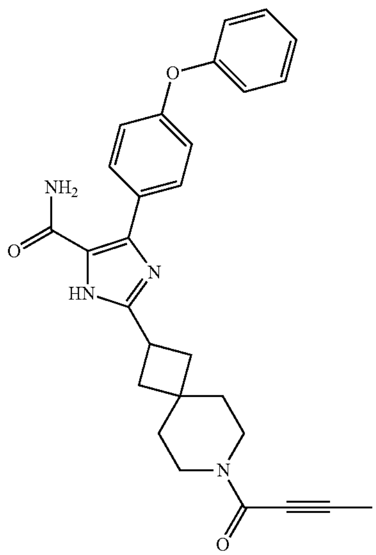 [SMILES: CC#CC(=O)N1CCC2(CC1)CC(c1nc(-c3ccc(Oc4ccccc4)cc3)c(C(N)=O)[nH]1)C2] | 4.3 | A | 2.87 | 469.3 |
| 88 | 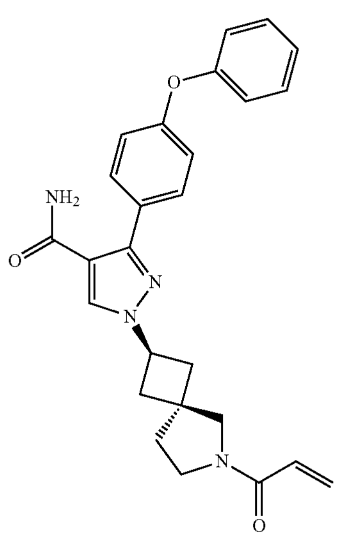 [SMILES: C=CC(=O)N1CC[C@]2(C1)C[C@@H](n1cc(C(N)=O)c(-c3ccc(Oc4ccccc4)cc3)n1)C2] | 21 | A | 2.96 | 443.4 |

TABLE of compounds and Biological activity

| Example | Structure | BTK IC50 (nM) | HPLC Method | RT (min) | m/z [M + H]+ |
|---|---|---|---|---|---|
| 89 | 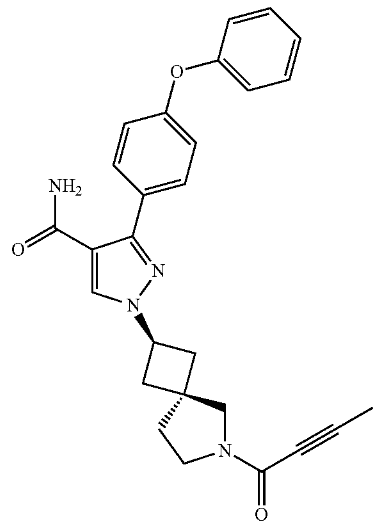 [SMILES: CC#CC(=O)N1CC[C@]2(C1)C[C@@H](n1cc(C(N)=O)c(-c3ccc(Oc4ccccc4)cc3)n1)C2] | 34 | A | 2.98 | 455.3 |
| 90 | 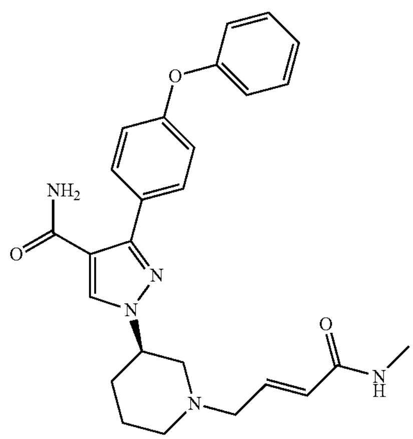 [SMILES: CNC(=O)/C=C/CN1CCC[C@@H](n2cc(C(N)=O)c(-c3ccc(Oc4ccccc4)cc3)n2)C1] | 90 | B | 0.55 | 460.1 |
| 91 | 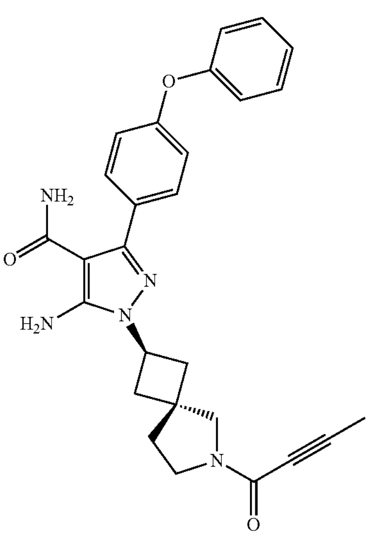 [SMILES: CC#CC(=O)N1CC[C@]2(C1)C[C@H](n1nc(-c3ccc(Oc4ccccc4)cc3)c(C(N)=O)c1N)C2] | 0.79 | A | 2.94 | 470.3 |

-continued

TABLE of compounds and Biological activity

| Example | Structure | BTK IC50 (nM) | HPLC Method | RT (min) | m/z [M + H]+ |
|---|---|---|---|---|---|
| 92 | 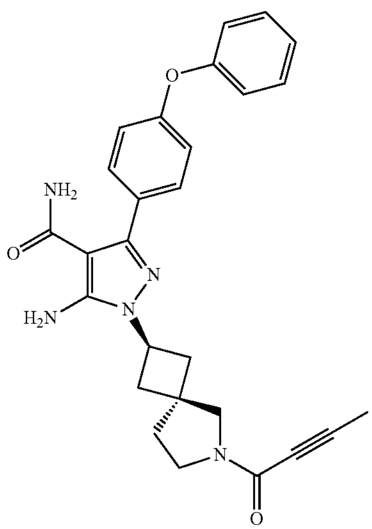 [SMILES: CC#CC(=O)N1CC[C@]2(C1)C[C@@H](n1nc(-c3ccc(Oc4ccccc4)cc3)c(C(N)=O)c1N)C2] | 0.89 | A | 2.88 | 470.3 |
| 93 | 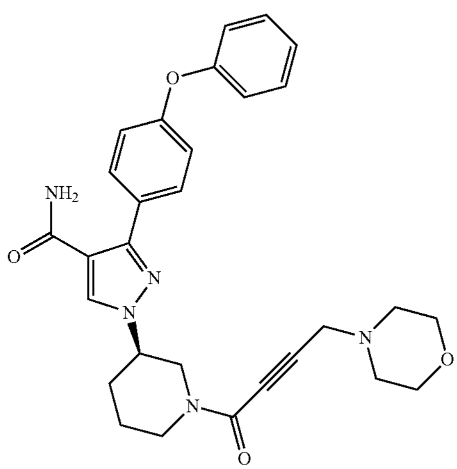 [SMILES: NC(=O)c1cn([C@@H]2CCCN(C(=O)C#CCN3CCOCC3)C2)nc1-c1ccc(Oc2ccccc2)cc1] | 33 | A | 2.80 | 514.3 |
| 94 | 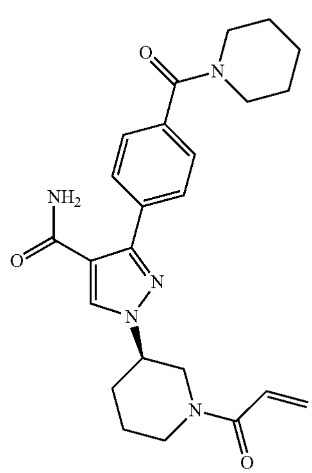 [SMILES: C=CC(=O)N1CCC[C@@H](n2cc(C(N)=O)c(-c3ccc(C(=O)N4CCCCC4)cc3)n2)C1] | 8200 | A | 2.75 | 436.3 |

-continued

TABLE of compounds and Biological activity

| Example | Structure | BTK IC50 (nM) | HPLC Method | RT (min) | m/z [M + H]+ |
|---|---|---|---|---|---|
| 95 | 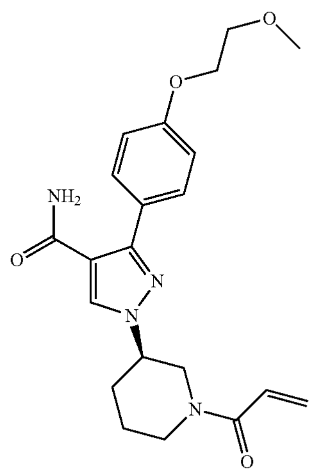 [SMILES: C=CC(=O)N1CCC[C@@H](n2cc(C(N)=O)c(-c3ccc(OCCOC)cc3)n2)C1] | 1600 | A | 2.71 | 399.3 |
| 96 | 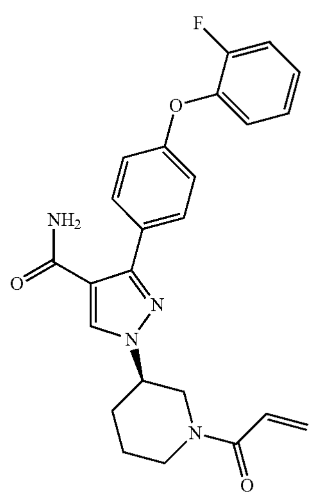 [SMILES: C=CC(=O)N1CCC[C@@H](n2cc(C(N)=O)c(-c3ccc(Oc4ccccc4F)cc3)n2)C1] | 4.8 | A | 2.95 | 435.3 |
| 97 | 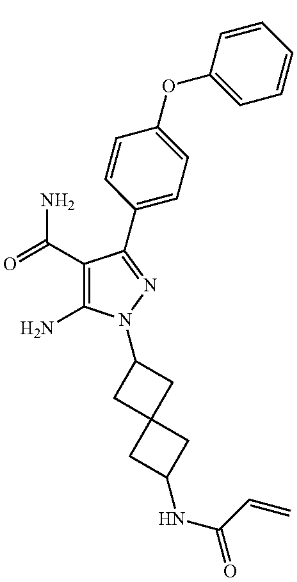 [SMILES: C=CC(=O)NC1CC2(C1)CC(n1nc(-c3ccc(Oc4ccccc4)cc3)c(C(N)=O)c1N)C2] | 0.8 | A | 2.93 | 458.3 |

-continued

TABLE of compounds and Biological activity

| Example | Structure | BTK IC50 (nM) | HPLC Method | RT (min) | m/z [M + H]+ |
|---------|-----------|---------------|-------------|----------|--------------|
| 98 | 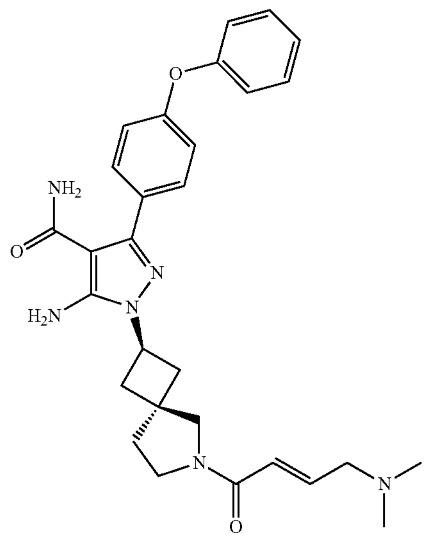 [SMILES: CN(C)C/C=C/C(=O)N1CC[C@]2(C1)C[C@@H](n1nc(-c3ccc(Oc4ccccc4)cc3)c(C(N)=O)c1N)C2] | 0.7 | A | 2.69 | 515.4 |
| 99 | 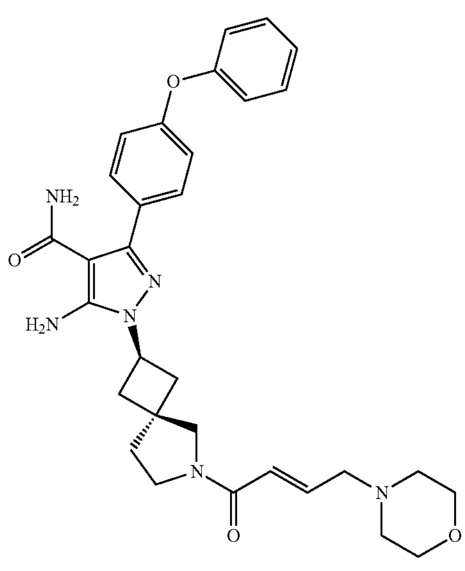 [SMILES: NC(=O)c1c(-c2ccc(Oc3ccccc3)cc2)nn([C@H]2C[C@]3(CCN(C(=O)/C=C/CN4CCOCC4)C3)C2)c1N] | 3.2 | A | 2.76 | 557.3 |

-continued
TABLE of compounds and Biological activity
| Example | Structure | BTK IC50 (nM) | HPLC Method | RT (min) | m/z [M + H]+ |
|---|---|---|---|---|---|
| 100 | 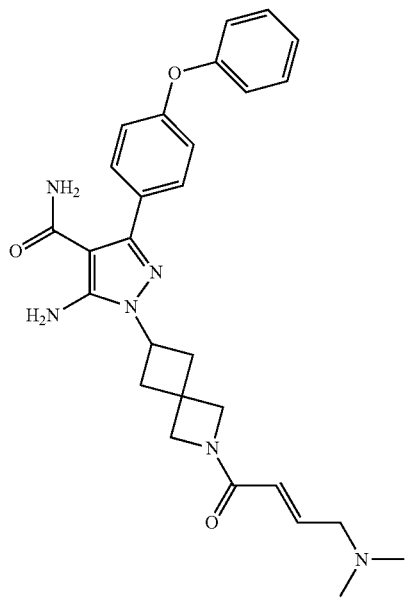 [SMILES: CN(C)C/C=C/C(=O)N1CC2(CC(n3nc(-c4ccc(Oc5ccccc5)cc4)c(C(N)=O)c3N)C2)C1] | 0.8 | A | 2.63 | 501.3 |
| 101 | 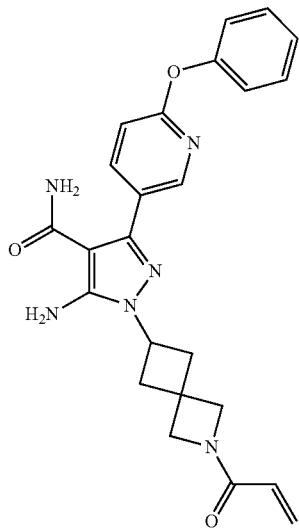 [SMILES: C=CC(=O)N1CC2(CC(n3nc(-c4ccc(Oc5ccccc5)nc4)c(C(N)=O)c3N)C2)C1] | 9.2 | A | 2.71 | 445.4 |

-continued
TABLE of compounds and Biological activity
| Example | Structure | BTK IC50 (nM) | HPLC Method | RT (min) | m/z [M + H]+ |
|---|---|---|---|---|---|
| 102 | 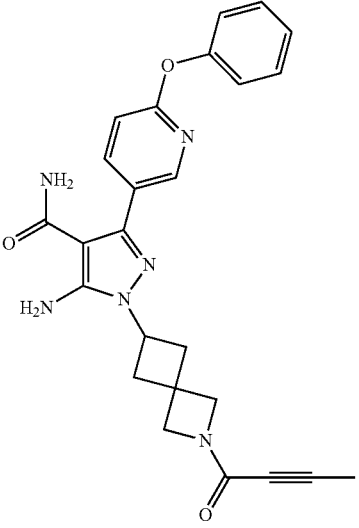 [SMILES: CC#CC(=O)N1CC2(CC(n3nc(-c4ccc(Oc5ccccc5)nc4)c(C(N)=O)c3N)C2)C1] | 2.7 | A | 2.83 | 457.3 |
| 103 | 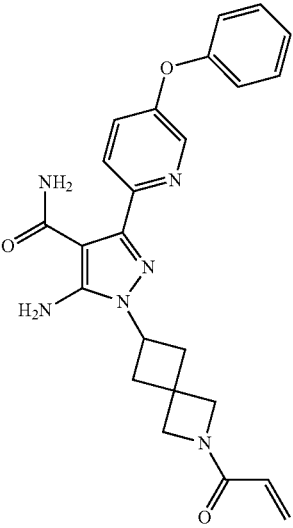 [SMILES: C=CC(=O)N1CC2(CC(n3nc(-c4ccc(Oc5ccccc5)cn4)c(C(N)=O)c3N)C2)C1] | 2.8 | A | 3.13 | 445.2 |

TABLE of compounds and Biological activity
| Example | Structure | BTK IC50 (nM) | HPLC Method | RT (min) | m/z [M + H]+ |
|---------|-----------|---------------|-------------|----------|--------------|
| 104 | 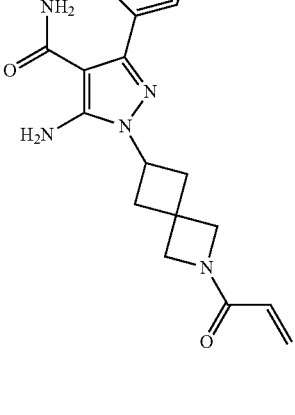 | 19 | A | 2.79 | 422.4 |
| 105 | 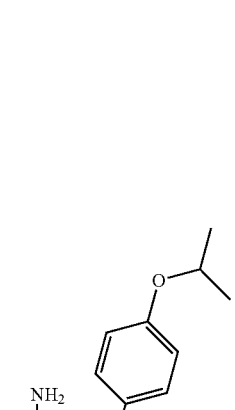 | 13 | A | 2.77 | 410.3 |

-continued

TABLE of compounds and Biological activity

| Example | Structure | BTK IC50 (nM) | HPLC Method | RT (min) | m/z [M + H]+ |
|---|---|---|---|---|---|
| 106 | 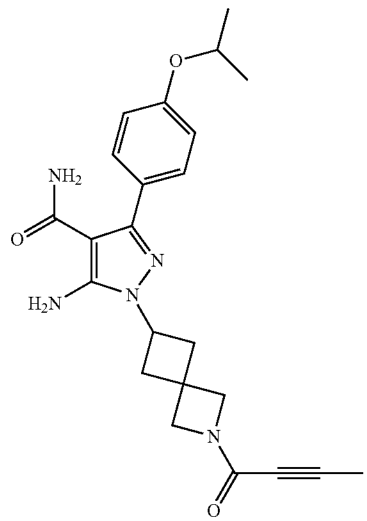 [SMILES: CC#CC(=O)N1CC2(CC(n3nc(-c4ccc(OC(C)C)cc4)c(C(N)=O)c3N)C2)C1] | 13 | A | 2.81 | 422.4 |
| 107 | 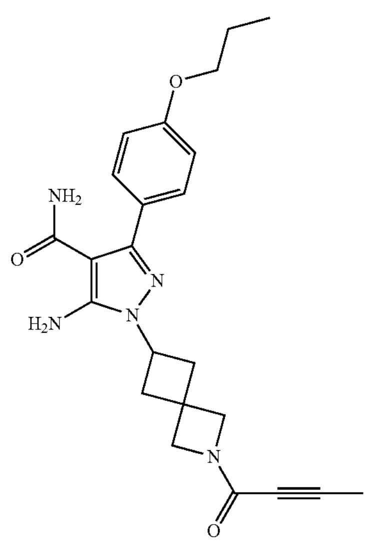 | 3.3 | A | 2.81 | 422.4 |

TABLE of compounds and Biological activity
| Example | Structure | BTK IC50 (nM) | HPLC Method | RT (min) | m/z [M + H]+ |
|---|---|---|---|---|---|
| 108 | 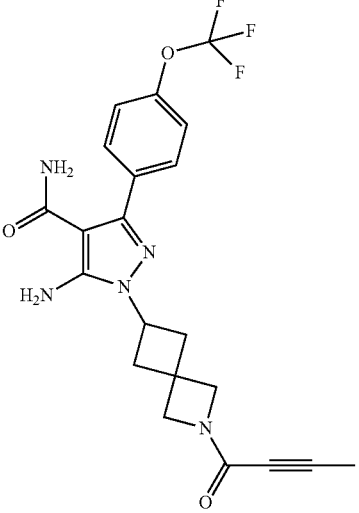 | 14 | A | 2.75 | 448.3 |
| 109 | 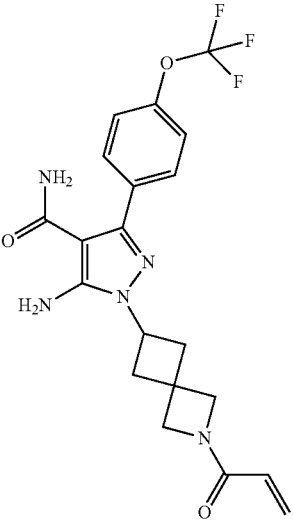 [SMILES: C=CC(=O)N1CC2(CC(n3nc(-c4ccc(OC(F)(F)F)cc4)c(C(N)=O)c3N)C2)C1] | 24 | A | 2.86 | 436.3 |

TABLE of compounds and Biological activity
| Example | Structure | BTK IC50 (nM) | HPLC Method | RT (min) | m/z [M + H]+ |
|---|---|---|---|---|---|
| 110 | 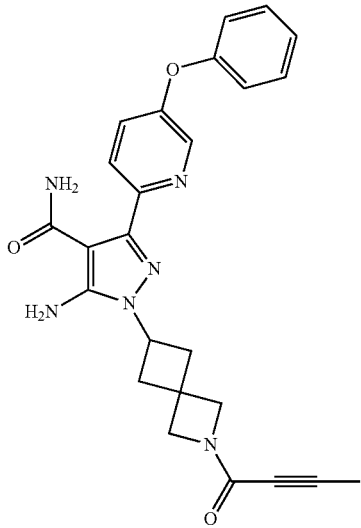 [SMILES: CC#CC(=O)N1CC2(CC(n3nc(-c4ccc(Oc5ccccc5)cn4)c(C(N)=O)c3N)C2)C1] | 0.87 | A | 3.09 | 457.3 |
| 111 | 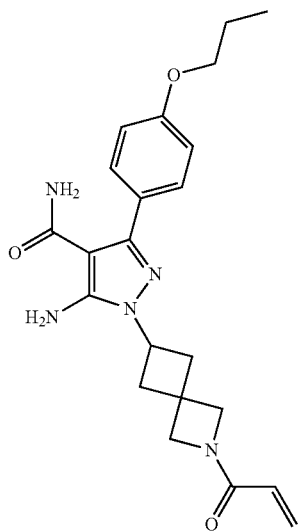 [SMILES: C=CC(=O)N1CC2(CC(n3nc(-c4ccc(OCCC)cc4)c(C(N)=O)c3N)C2)C1] | 16 | A | 2.77 | 410.4 |

TABLE of compounds and Biological activity

| Example | Structure | BTK IC50 (nM) | HPLC Method | RT (min) | m/z [M + H]+ |
|---------|-----------|---------------|-------------|----------|--------------|
| 112 | 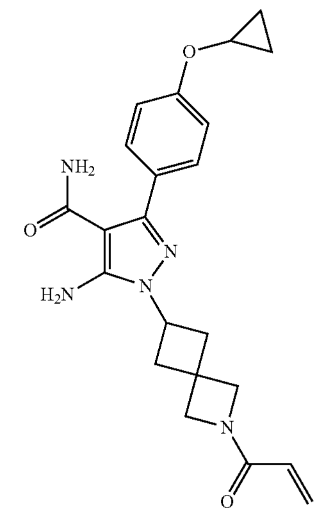 [SMILES: C=CC(=O)N1CC2(CC(n3nc(-c4ccc(OC5CC5)cc4)c(C(N)=O)c3N)C2)C1] | 6.7 | A | 2.82 | 408.4 |
| 113 | 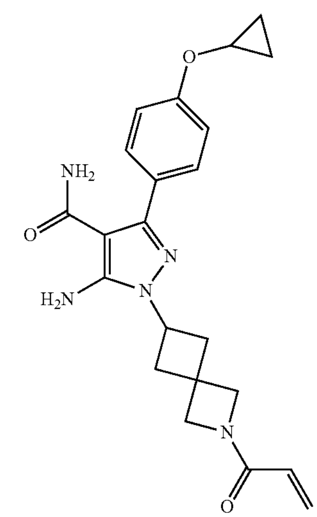 [SMILES: C=CC(=O)N1CC2(CC(n3nc(-c4ccc(OC5CC5)cc4)c(C(N)=O)c3N)C2)C1] | 4.3 | A | 2.85 | 420.4 |
| 114 | 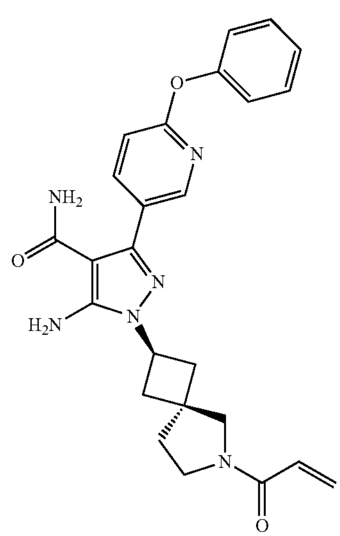 [SMILES: C=CC(=O)N1CC[C@]2(C1)C[C@@H](n1nc(-c3ccc(Oc4ccccc4)nc3)c(C(N)=O)c1N)C2] | 3.4 | A | 2.87 | 459.3 |

-continued
TABLE of compounds and Biological activity
| Example | Structure | BTK IC50 (nM) | HPLC Method | RT (min) | m/z [M + H]+ |
|---|---|---|---|---|---|
| 115 | 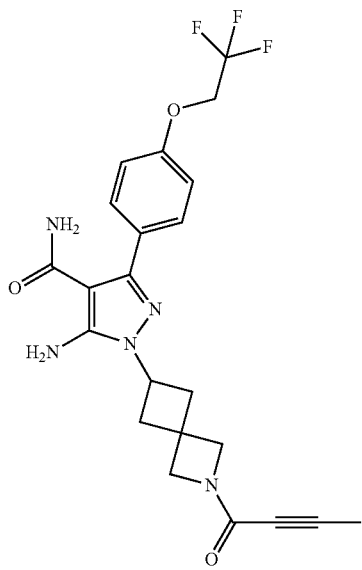 [SMILES: CC#CC(=O)N1CC2(CC(n3nc(-c4ccc(OCC(F)(F)F)cc4)c(C(N)=O)c3N)C2)C1] | 3.5 | A | 2.82 | 462.3 |
| 116 | 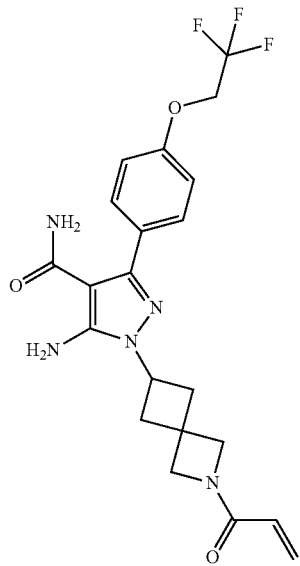 [SMILES: C=CC(=O)N1CC2(CC(n3nc(-c4ccc(OCC(F)(F)F)cc4)c(C(N)=O)c3N)C2)C1] | 12 | A | 2.78 | 450.3 |

TABLE of compounds and Biological activity

| Example | Structure | BTK IC50 (nM) | HPLC Method | RT (min) | m/z [M + H]+ |
|---|---|---|---|---|---|
| 117 | 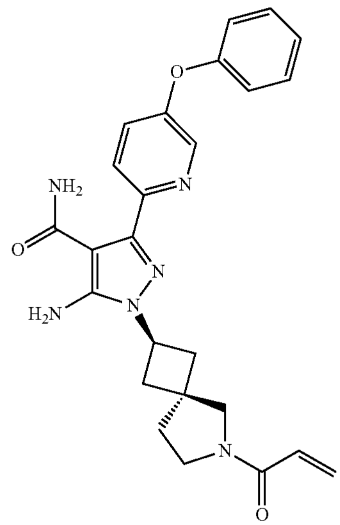 [SMILES: C=CC(=O)N1CC[C@]2(C1)C[C@@H](n1nc(-c3ccc(Oc4ccccc4)cn3)c(C(N)=O)c1N)C2] | 1.1 | A | 3.52 | 459.2 |
| 118 | 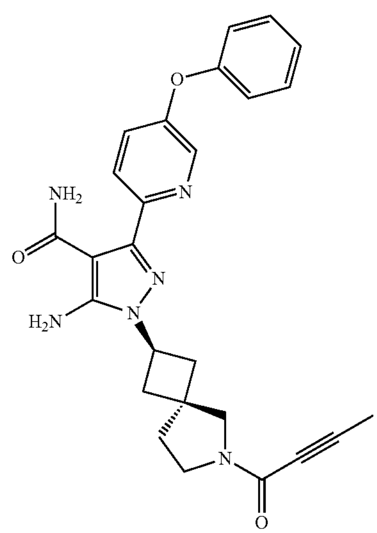 | 0.5 | A | 3.49 | 471.2 |

-continued
TABLE of compounds and Biological activity
| Example | Structure | BTK IC50 (nM) | HPLC Method | RT (min) | m/z [M + H]+ |
|---|---|---|---|---|---|
| 119 | 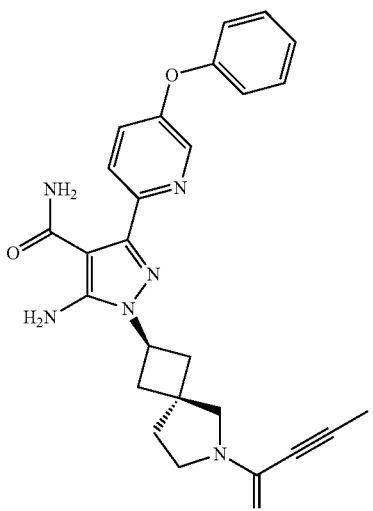 | 11 | A | 3.25 | 471.3 |
| 120 | 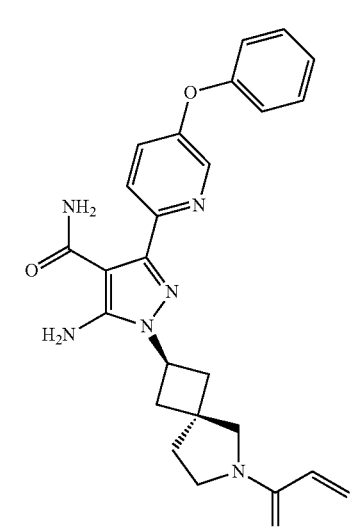 | 3.5 | A | 3.29 | 459.2 |
| 121 | 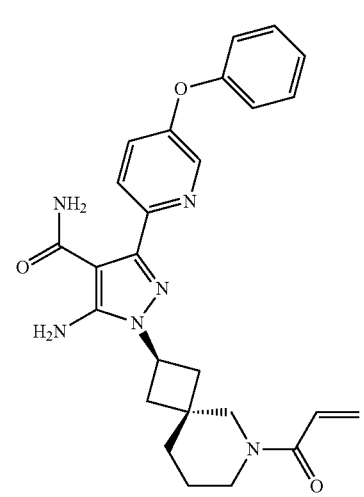 [SMILES: C=CC(=O)N1CCC[C@]2(C1)C[C@H](n1nc(-c3ccc(Oc4ccccc4)cn3)c(C(N)=O)c1N)C2] | 0.2 | A | 3.13 | 472.2 |

TABLE of compounds and Biological activity -continued

| Example | Structure | BTK IC50 (nM) | HPLC Method | RT (min) | m/z [M + H]+ |
|---|---|---|---|---|---|
| 122 | 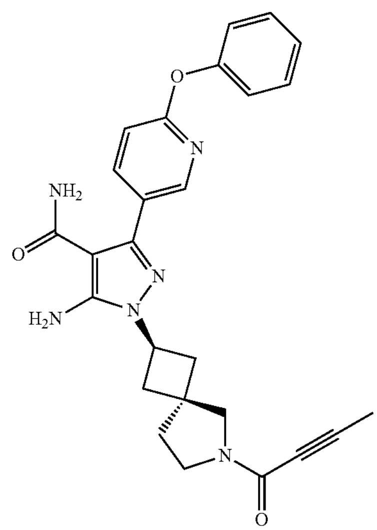 | 17 | A | 2.91 | 471.3 |
| 123 | 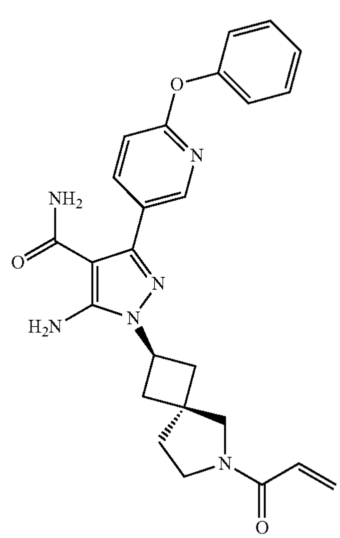 [SMILES: C=CC(=O)N1CC[C@]2(C1)C[C@@H](n1nc(-c3ccc(Oc4ccccc4)nc3)c(C(N)=O)c1N)C2] | 9.1 | A | 2.88 | 459.3 |

TABLE of compounds and Biological activity

| Example | Structure | BTK IC50 (nM) | HPLC Method | RT (min) | m/z [M + H]+ |
|---|---|---|---|---|---|
| 124 | 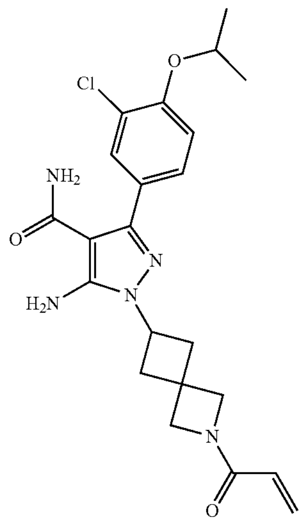 [SMILES: C=CC(=O)N1CC2(CC(n3nc(-c4ccc(OC(C)C)c(Cl)c4)c(C(N)=O)c3N)C2)C1] | 10 | B | 1.73 | 444.1 |
| 125 | 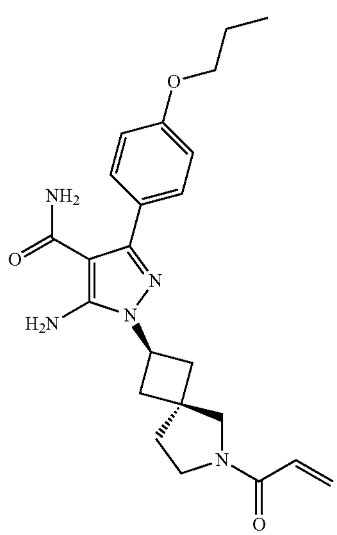 [SMILES: C=CC(=O)N1CC[C@]2(C1)C[C@@H](n1nc(-c3ccc(OCCC)cc3)c(C(N)=O)c1N)C2] | 7.5 | B | 0.85 | 424.0 |

TABLE of compounds and Biological activity
| Example | Structure | BTK IC50 (nM) | HPLC Method | RT (min) | m/z [M + H]+ |
|---|---|---|---|---|---|
| 126 | 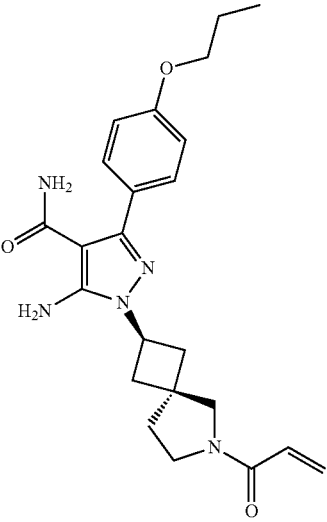 [SMILES: C=CC(=O)N1CC[C@]2(C1)C[C@@H](n1nc(-c3ccc(OCCC)cc3)c(C(N)=O)c1N)C2] | 28 | A | 2.98 | 424.3 |
| 127 | 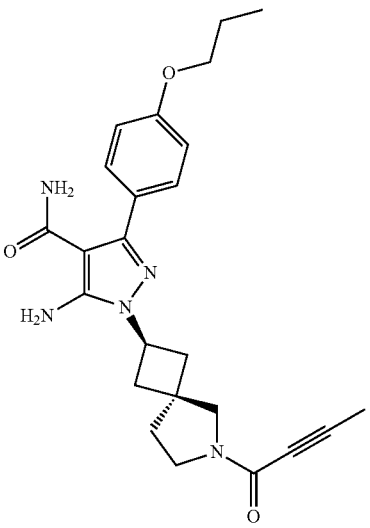 [SMILES: CC#CC(=O)N1CC[C@]2(C1)C[C@@H](n1nc(-c3ccc(OCCC)cc3)c(C(N)=O)c1N)C2] | 15 | B | 0.86 | 436 |
| 128 | 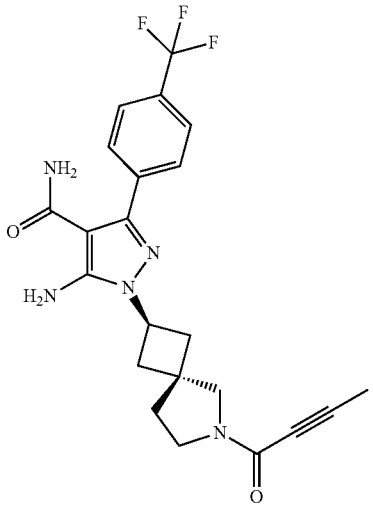 [SMILES: CC#CC(=O)N1CC[C@]2(C1)C[C@H](n1nc(-c3ccc(C(F)(F)F)cc3)c(C(N)=O)c1N)C2] | 0.9 | A | 3.02 | 446.4 |

-continued
TABLE of compounds and Biological activity
| Example | Structure | BTK IC50 (nM) | HPLC Method | RT (min) | m/z [M + H]+ |
|---|---|---|---|---|---|
| 129 | 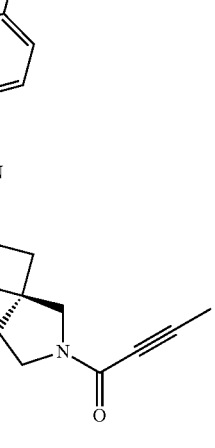 | 29 | B | 0.85 | 446.1 |
| 130 | 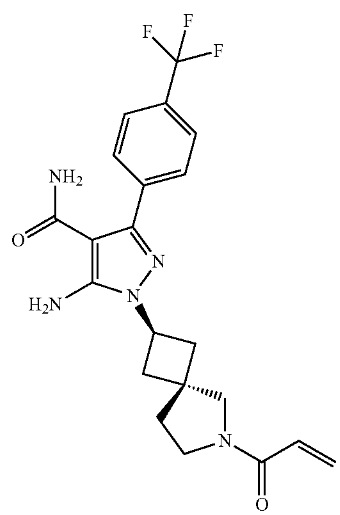 [SMILES: C=CC(=O)N1CC[C@]2(C1)C[C@H](n1nc(-c3ccc(C(F)(F)F)cc3)c(C(N)=O)c1N)C2] | 6.4 | A | 3 | 434.4 |
| 131 | 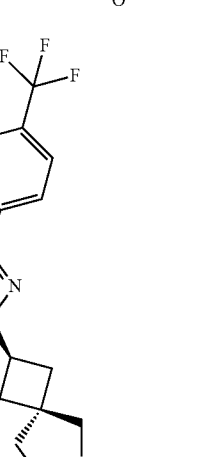 | 28 | B | 0.80 | 433.9 |

-continued

TABLE of compounds and Biological activity

| Example | Structure | BTK IC50 (nM) | HPLC Method | RT (min) | m/z [M + H]+ |
|---------|-----------|---------------|-------------|----------|--------------|
| 132 | 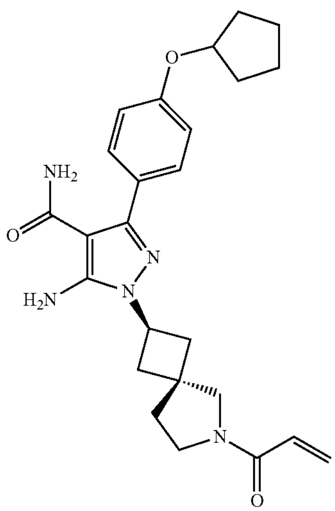 [SMILES: C=CC(=O)N1CC[C@]2(C1)C[C@H](n1nc(-c3ccc(OC4CCCC4)cc3)c(C(N)=O)c1N)C2] | 1.9 | B | 1.02 | 451.5 |
| 133 | 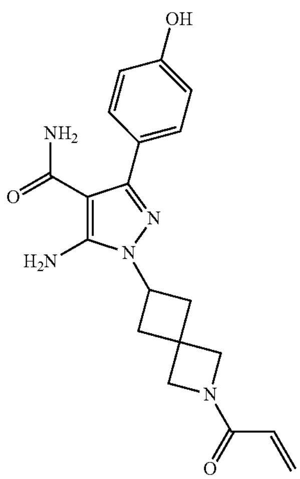 [SMILES: C=CC(=O)N1CC2(CC(n3nc(-c4ccc(O)cc4)c(C(N)=O)c3N)C2)C1] | 8.4 | A | 2.64 | 368.3 |
| 134 | 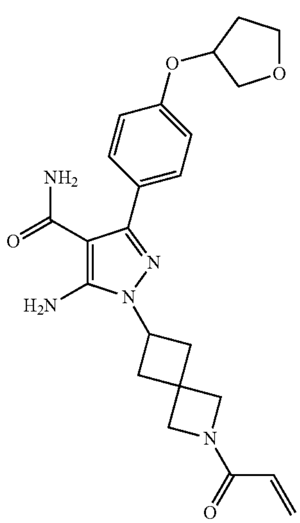 [SMILES: C=CC(=O)N1CC2(CC(n3nc(-c4ccc(OC5CCOC5)cc4)c(C(N)=O)c3N)C2)C1] | 120 | B | 0.59 | 438.3 |

-continued

TABLE of compounds and Biological activity

| Example | Structure | BTK IC50 (nM) | HPLC Method | RT (min) | m/z [M + H]+ |
|---------|-----------|---------------|-------------|----------|--------------|
| 135 | 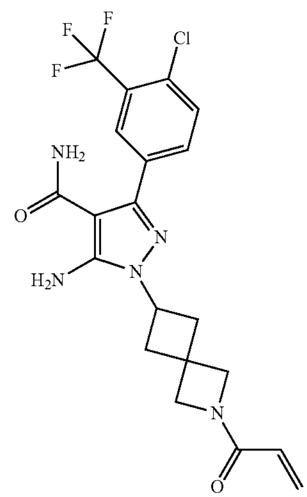 [SMILES: C=CC(=O)N1CC2(CC(n3nc(-c4ccc(Cl)c(C(F)(F)F)c4)c(C(N)=O)c3N)C2)C1] | 26 | A | 2.83 | 454.3 |
| 136 | 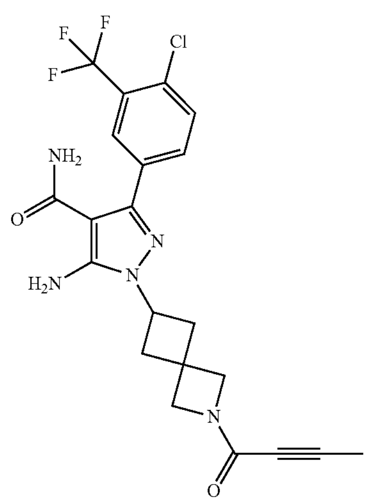 [SMILES: CC#CC(=O)N1CC2(CC(n3nc(-c4ccc(Cl)c(C(F)(F)F)c4)c(C(N)=O)c3N)C2)C1] | 14 | B | 0.91 | 466 |
| 137 | 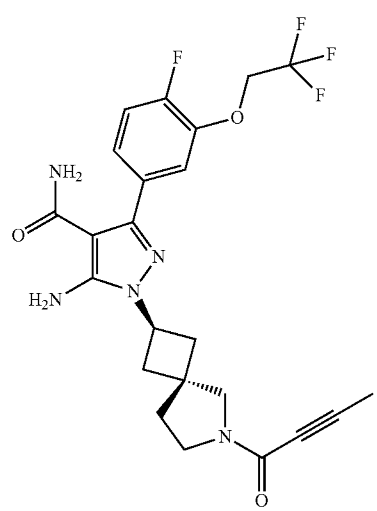 [SMILES: CC#CC(=O)N1CC[C@]2(C1)C[C@H](n1nc(-c3ccc(F)c(OCC(F)(F)F)c3)c(C(N)=O)c1N)C2] | 1.6 | B | 0.89 | 494.1 |

TABLE of compounds and Biological activity
| Example | Structure | BTK IC50 (nM) | HPLC Method | RT (min) | m/z [M + H]+ |
|---|---|---|---|---|---|
| 138 | 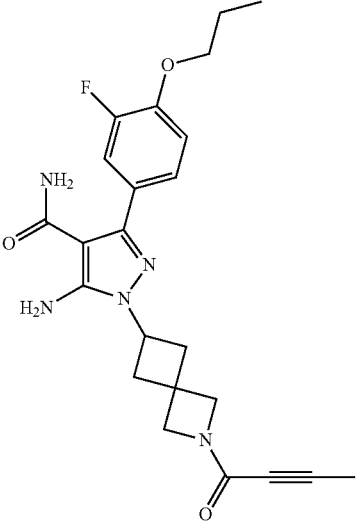 [SMILES: CC#CC(=O)N1CC2(CC(n3nc(-c4ccc(OCCC)c(F)c4)c(C(N)=O)c3N)C2)C1] | 2.2 | B | 0.86 | 440.1 |
| 139 | 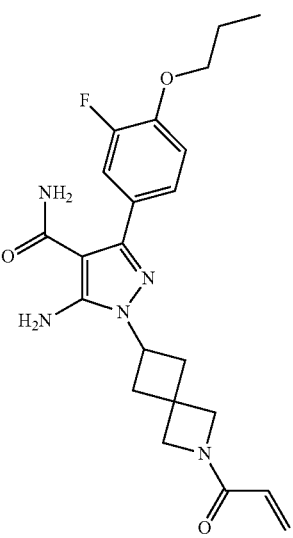 [SMILES: C=CC(=O)N1CC2(CC(n3nc(-c4ccc(OCCC)c(F)c4)c(C(N)=O)c3N)C2)C1] | 16 | B | 0.56 | 428.1 |

-continued

TABLE of compounds and Biological activity

| Example | Structure | BTK IC50 (nM) | HPLC Method | RT (min) | m/z [M + H]+ |
|---|---|---|---|---|---|
| 140 | 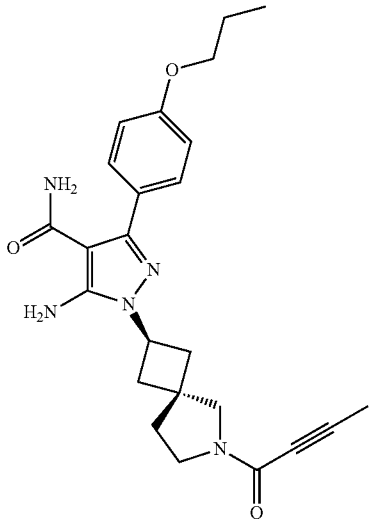 [SMILES: CC#CC(=O)N1CC[C@]2(C1)C[C@H](n1nc(-c3ccc(OCCC)cc3)c(C(N)=O)c1N)C2] | 0.9 | B | 0.90 | 436.2 |
| 141 | 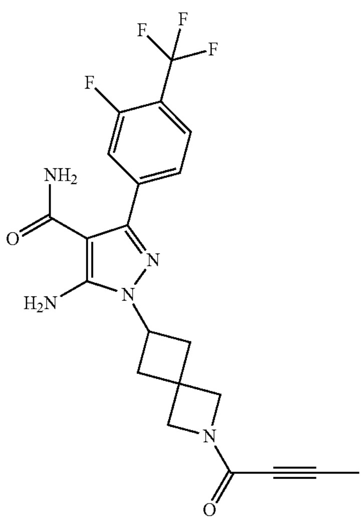 [SMILES: CC#CC(=O)N1CC2(CC(n3nc(-c4ccc(C(F)(F)F)c(F)c4)c(C(N)=O)c3N)C2)C1] | 14 | B | 0.87 | 450.0 |
| 142 | 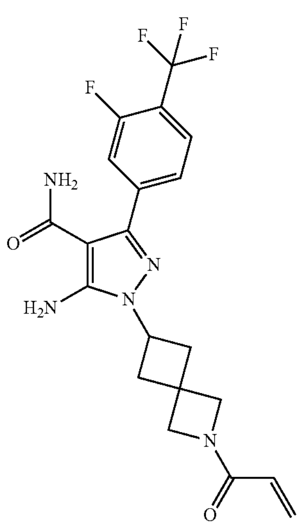 [SMILES: C=CC(=O)N1CC2(CC(n3nc(-c4ccc(C(F)(F)F)c(F)c4)c(C(N)=O)c3N)C2)C1] | 29 | B | 0.82 | 438.0 |

-continued

TABLE of compounds and Biological activity

| Example | Structure | BTK IC50 (nM) | HPLC Method | RT (min) | m/z [M + H]+ |
|---|---|---|---|---|---|
| 143 | 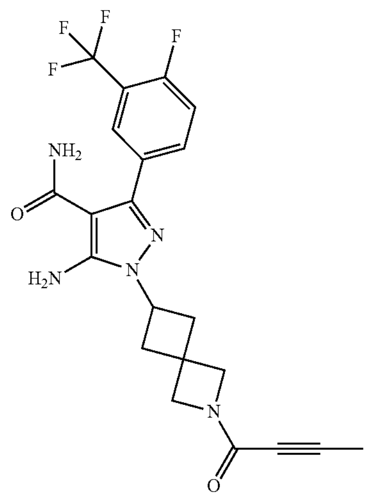 [SMILES: CC#CC(=O)N1CC2(CC(n3nc(-c4ccc(F)c(C(F)(F)F)c4)c(C(N)=O)c3N)C2)C1] | 37 | B | 0.85 | 450.0 |
| 144 | 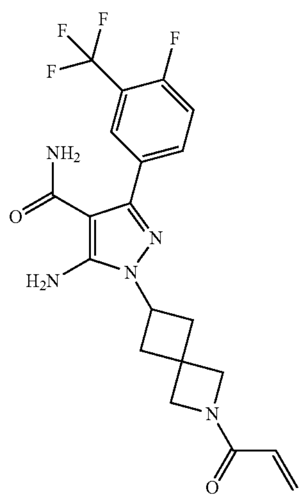 [SMILES: C=CC(=O)N1CC2(CC(n3nc(-c4ccc(F)c(C(F)(F)F)c4)c(C(N)=O)c3N)C2)C1] | 72 | B | 0.80 | 438.1 |
| 145 | 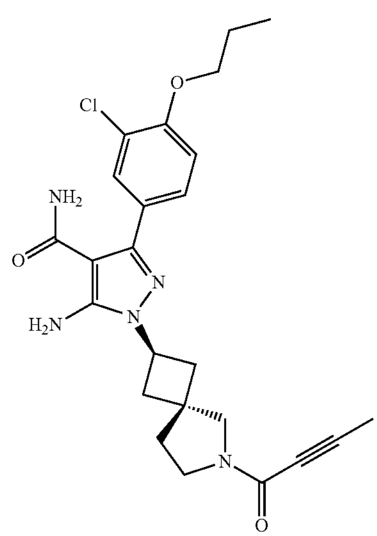 [SMILES: CC#CC(=O)N1CC[C@]2(C1)C[C@H](n1nc(-c3ccc(OCCC)c(Cl)c3)c(C(N)=O)c1N)C2] | 3.5 | A | 3.17 | 458.4 |

TABLE of compounds and Biological activity
| Example | Structure | BTK IC50 (nM) | HPLC Method | RT (min) | m/z [M + H]+ |
|---|---|---|---|---|---|
| 146 | 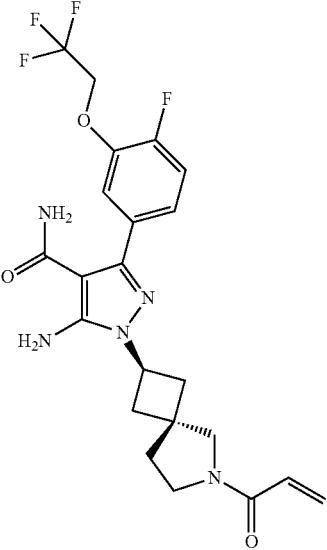 [SMILES: C=CC(=O)N1CC[C@]2(C1)C[C@H](n1nc(-c3ccc(F)c(OCC(F)(F)F)c3)c(C(N)=O)c1N)C2] | 22 | A | 2.95 | 482.4 |
| 147 | 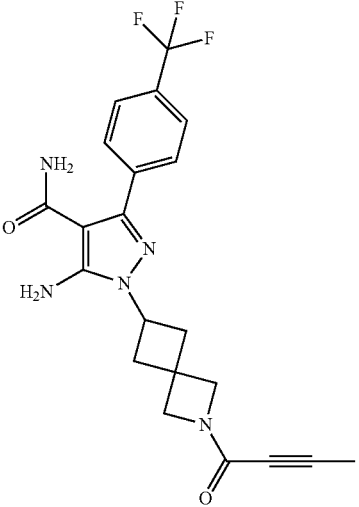 [SMILES: CC#CC(=O)N1CC2(CC(n3nc(-c4ccc(C(F)(F)F)cc4)c(C(N)=O)c3N)C2)C1] | 9.2 | B | 0.84 | 432.0 |

-continued

TABLE of compounds and Biological activity

| Example | Structure | BTK IC50 (nM) | HPLC Method | RT (min) | m/z [M + H]+ |
|---------|-----------|---------------|-------------|----------|--------------|
| 148 | 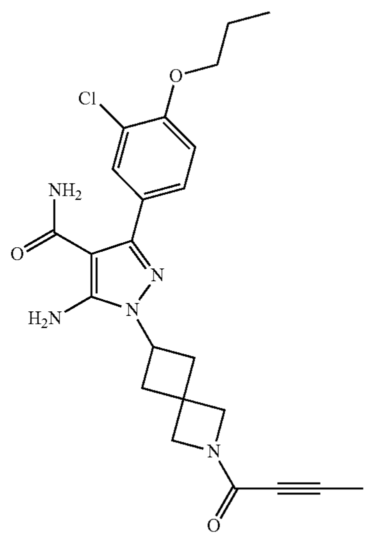 | 3.0 | A | 3.03 | 456.3 |
| 149 | 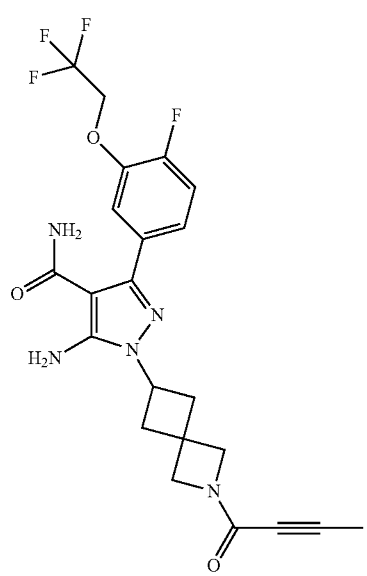 [SMILES: CC#CC(=O)N1CC2(CC(n3nc(-c4ccc(F)c(OCC(F)(F)F)c4)c(C(N)=O)c3N)C2)C1] | 100 | B | 0.78 | 480.4 |

-continued

TABLE of compounds and Biological activity

| Example | Structure | BTK IC50 (nM) | HPLC Method | RT (min) | m/z [M + H]+ |
|---|---|---|---|---|---|
| 150 | 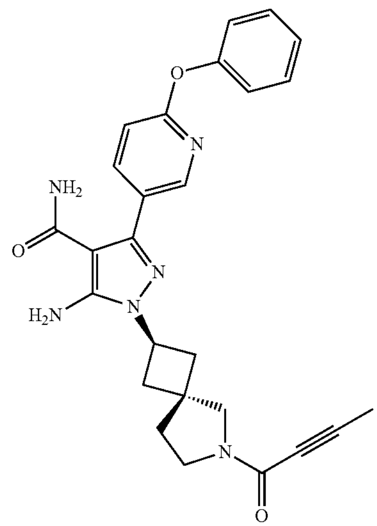 [SMILES: CC#CC(=O)N1CC[C@]2(C1)C[C@H](n1nc(-c3ccc(Oc4ccccc4)nc3)c(C(N)=O)c1N)C2] | 0.8 | B | 0.83 | 471.2 |
| 151 | 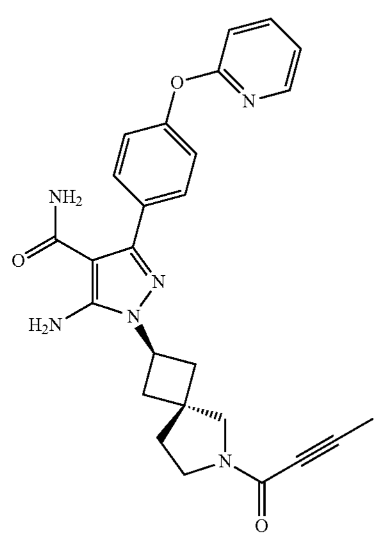 [SMILES: CC#CC(=O)N1CC[C@]2(C1)C[C@H](n1nc(-c3ccc(Oc4ccccn4)cc3)c(C(N)=O)c1N)C2] | 0.7 | B | 0.78 | 471.3 |

TABLE of compounds and Biological activity

| Example | Structure | BTK IC50 (nM) | HPLC Method | RT (min) | m/z [M + H]+ |
|---|---|---|---|---|---|
| 152 | 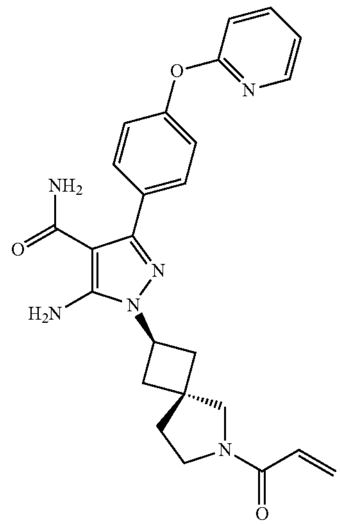 [SMILES: C=CC(=O)N1CC[C@]2(C1)C[C@H](n1nc(-c3ccc(Oc4ccccn4)cc3)c(C(N)=O)c1N)C2] | 1.5 | B | 0.73 | 459.3 |
| 153 | 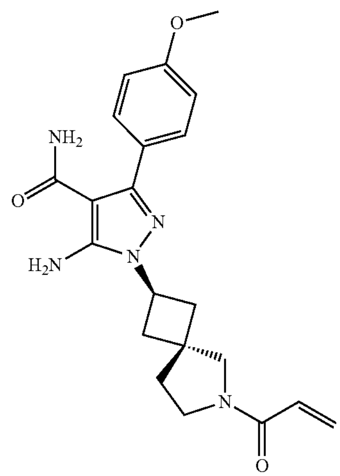 [SMILES: C=CC(=O)N1CC[C@]2(C1)C[C@H](n1nc(-c3ccc(OC)cc3)c(C(N)=O)c1N)C2] | 2.3 | B | 0.68 | 396.1 |
| 154 | 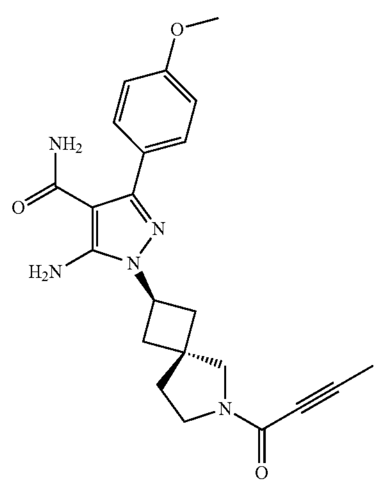 [SMILES: CC#CC(=O)N1CC[C@]2(C1)C[C@H](n1nc(-c3ccc(OC)cc3)c(C(N)=O)c1N)C2] | 0.6 | B | 0.71 | 408.3 |

TABLE of compounds and Biological activity -continued

| Example | Structure | BTK IC50 (nM) | HPLC Method | RT (min) | m/z [M + H]+ |
|---|---|---|---|---|---|
| 155 | 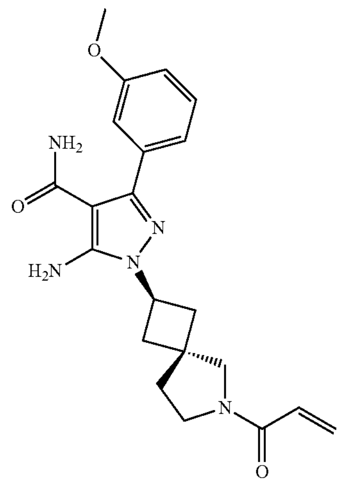 [SMILES: C=CC(=O)N1CC[C@]2(C1)C[C@H](n1nc(-c3cccc(OC)c3)c(C(N)=O)c1N)C2] | 7.3 | B | 0.69 | 396.2 |
| 156 | 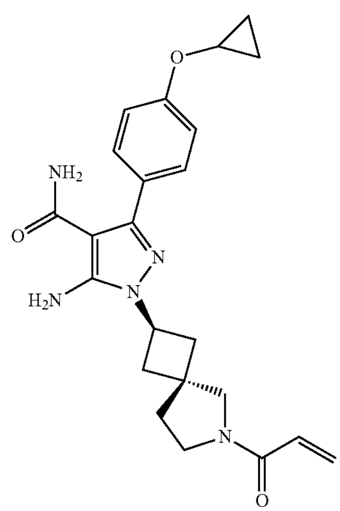 [SMILES: C=CC(=O)N1CC[C@]2(C1)C[C@H](n1nc(-c3ccc(OC4CC4)cc3)c(C(N)=O)c1N)C2] | 16 | B | 0.70 | 420.4 [M − H]+ |
| 157 | 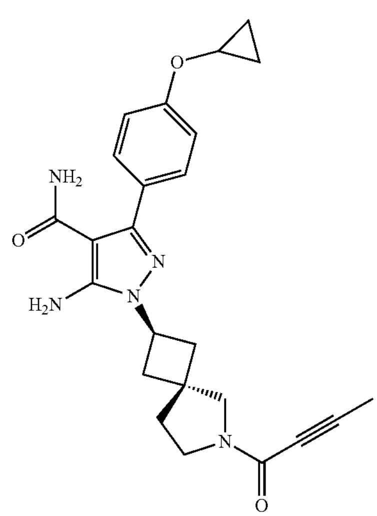 [SMILES: CC#CC(=O)N1CC[C@]2(C1)C[C@H](n1nc(-c3ccc(OC4CC4)cc3)c(C(N)=O)c1N)C2] | 2.0 | B | 0.86 | 434.6 |

-continued

TABLE of compounds and Biological activity

| Example | Structure | BTK IC50 (nM) | HPLC Method | RT (min) | m/z [M + H]+ |
|---------|-----------|---------------|-------------|----------|--------------|
| 158 | 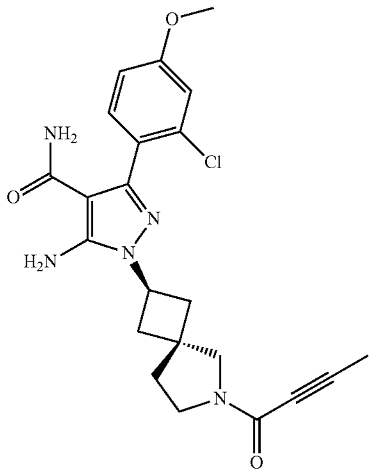 [SMILES: CC#CC(=O)N1CC[C@]2(C1)C[C@H](n1nc(-c3ccc(OC)cc3Cl)c(C(N)=O)c1N)C2] | 6.3 | B | 0.80 | 442.1 |
| 159 | 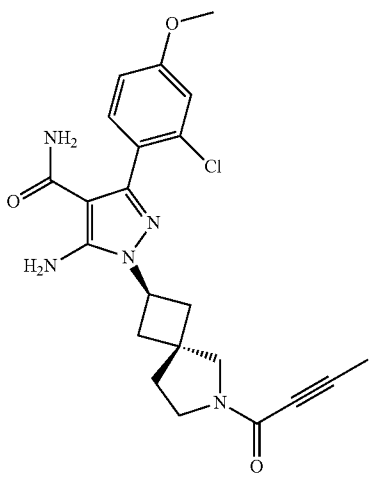 [SMILES: CC#CC(=O)N1CC[C@]2(C1)C[C@H](n1nc(-c3ccc(OC)cc3Cl)c(C(N)=O)c1N)C2] | 20 | B | 0.75 | 430.2 |
| 160 | 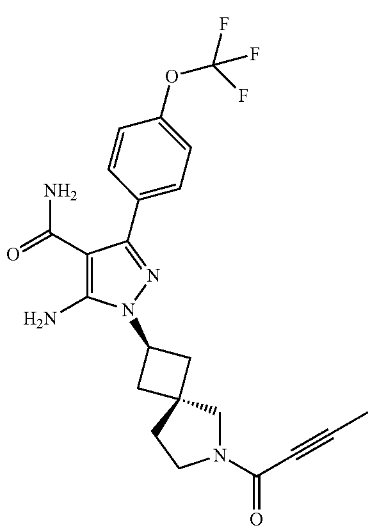 [SMILES: CC#CC(=O)N1CC[C@]2(C1)C[C@H](n1nc(-c3ccc(OC(F)(F)F)cc3)c(C(N)=O)c1N)C2] | 1.4 | B | 0.87 | 462.1 |

TABLE of compounds and Biological activity

| Example | Structure | BTK IC50 (nM) | HPLC Method | RT (min) | m/z [M + H]+ |
|---|---|---|---|---|---|
| 161 | 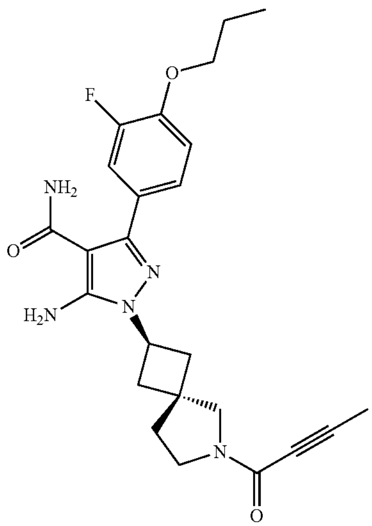 [SMILES: CC#CC(=O)N1CC[C@]2(C1)C[C@H](n1nc(-c3ccc(OCCC)c(F)c3)c(C(N)=O)c1N)C2] | 1.1 | B | 0.87 | 454.462.8 |
| 162 | 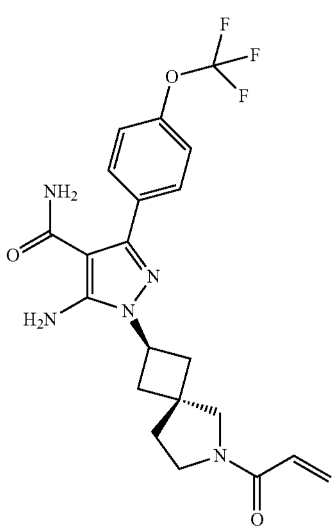 [SMILES: C=CC(=O)N1CC[C@]2(C1)C[C@H](n1nc(-c3ccc(OC(F)(F)F)cc3)c(C(N)=O)c1N)C2] | 9.2 | B | 0.91 | 450.2 |

TABLE of compounds and Biological activity
| Example | Structure | BTK IC50 (nM) | HPLC Method | RT (min) | m/z [M + H]+ |
|---|---|---|---|---|---|
| 163 | 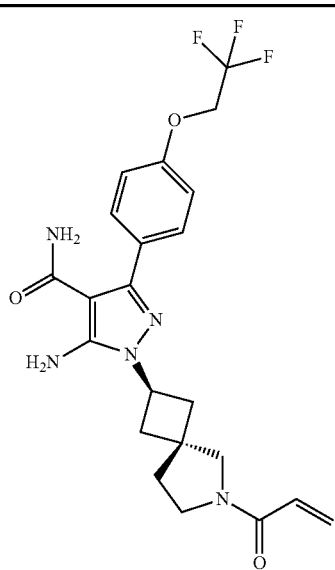 | 4.8 | B | 0.86 | 464.5 |
| 164 | 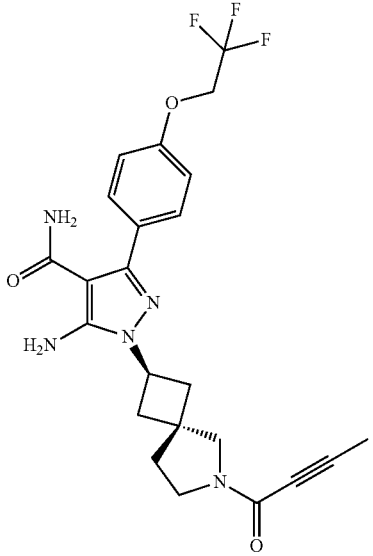 [SMILES: CC#CC(=O)N1CC[C@]2(C1)C[C@H](n1nc(-c3ccc(OCC(F)(F)F)cc3)c(C(N)=O)c1N)C2] | 0.5 | B | 0.90 | 476.2 |

TABLE of compounds and Biological activity

| Example | Structure | BTK IC50 (nM) | HPLC Method | RT (min) | m/z [M + H]+ |
|---|---|---|---|---|---|
| 165 | 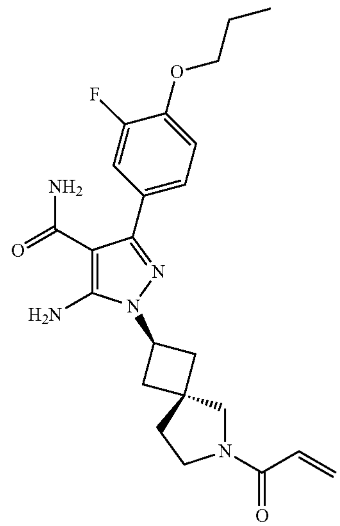 [SMILES: C=CC(=O)N1CC[C@]2(C1)C[C@H](n1nc(-c3ccc(OCCC)c(F)c3)c(C(N)=O)c1N)C2] | 15 | B | 0.89 | 440.2 [M − H]+ 443.2 |
| 166 | 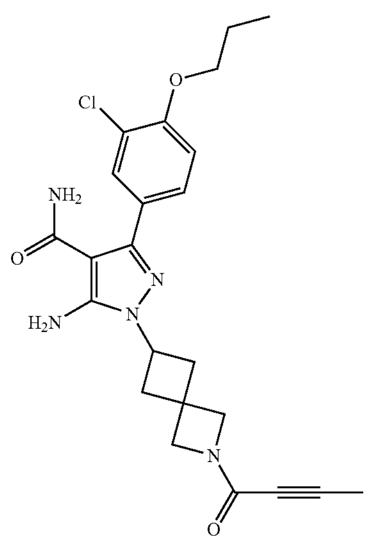 | 6.6 | B | 1.06 | 420.3 |

TABLE of compounds and Biological activity

| Example | Structure | BTK IC50 (nM) | HPLC Method | RT (min) | m/z [M + H]+ |
|---------|-----------|---------------|-------------|----------|--------------|
| 167 | 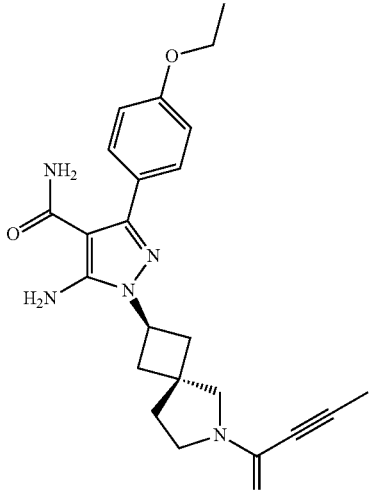 | 0.9 | B | 0.75 | 422.2 |
| 168 | 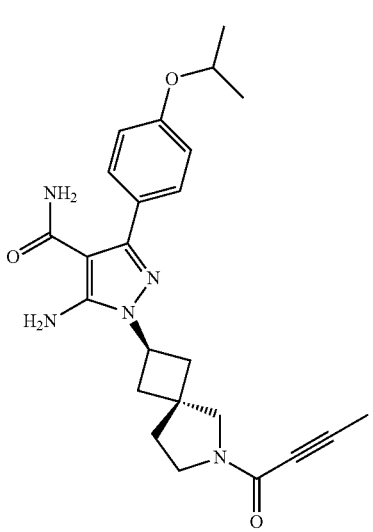 [SMILES: CC#CC(=O)N1CC[C@]2(C1)C[C@H](n1nc(-c3ccc(OC(C)C)cc3)c(C(N)=O)c1N)C2] | 1.2 | B | 0.84 | 436.3 | or the pharmaceutically acceptable salts thereof.

The present invention further relates to metabolites, and prodrugs of compounds of the formula (I).

The present invention further relates to a pharmaceutically acceptable salt of a compound of the formula (I) with inorganic or organic acids or bases.

In another aspect the invention relates to compounds of formula (I)—or the pharmaceutically acceptable salts thereof—as medicaments.

In another aspect the invention relates to compounds of formula (I)—or the pharmaceutically acceptable salts thereof—for use in a method for treatment of a patient.

In another aspect the invention relates to compounds of formula (I)—or the pharmaceutically acceptable salts thereof—for use in the treatment of autoimmune diseases and allergic disorders.

In another aspect the invention relates to the use of compounds of formula (I)—or the pharmaceutically acceptable salts thereof—for preparing a pharmaceutical composition for the treatment of autoimmune diseases and allergic disorders.

In another aspect the invention relates to a method for the treatment of autoimmune diseases and allergic disorders comprising administering a therapeutically effective amount of a compound of formula (I)—or one of the pharmaceutically acceptable salts thereof—to a patient.

In another aspect the invention relates to a pharmaceutical preparation containing as active substance one or more compounds of formula (I)—or the pharmaceutically acceptable salts thereof—optionally in combination with conventional excipients and/or carriers.

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example H₃C—, H₃C—CH₂—, H₃C—CH₂—CH₂—, H₃C—CH (CH₃)—, H₃C—CH₂—CH₂—CH₂—, H₃C—CH₂—CH (CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH (CH₃)—CH₂—CH₂—, H₃C—CH₂—C(CH₃)₂—, H₃C—C (CH₃)₂—CH₂—, H₃C—CH(CH₃)—CH(CH₃)— and H₃C—CH₂—CH(CH₂CH₃)—.

Further examples of alkyl are methyl (Me; —CH₃), ethyl (Et; —CH₂CH₃), 1-propyl (n-propyl; n-Pr; —CH₂CH₂CH₃), 2-propyl (i-Pr; iso-propyl; —CH(CH₃)₂), 1-butyl (n-butyl; n-Bu; —CH₂CH₂CH₂CH₃), 2-methyl-1-propyl (iso-butyl; i-Bu; —CH₂CH(CH₃)₂), 2-butyl (sec-butyl; sec-Bu; —CH(CH₃)CH₂CH₃), 2-methyl-2-propyl (tert-butyl; t-Bu; —C(CH₃)₃), 1-pentyl (n-pentyl; —CH₂CH₂CH₂CH₂CH₃), 2-pentyl (—CH(CH₃) CH₂CH₂CH₃), 3-pentyl (—CH(CH₂CH₃)₂), 3-methyl-1-butyl (iso-pentyl; —CH₂CH₂CH(CH₃)₂), 2-methyl-2-butyl (—C(CH₃)₂CH₂CH₃), 3-methyl-2-butyl (—CH(CH₃)CH (CH₃)₂), 2,2-dimethyl-1-propyl (neo-pentyl; —CH₂C (CH₃)₃), 2-methyl-1-butyl (—CH₂CH(CH₃)CH₂CH₃), 1-hexyl (n-hexyl; —CH₂CH₂CH₂CH₂CH₂CH₃), 2-hexyl (—CH(CH₃)CH₂CH₂CH₂CH₃), 3-hexyl (—CH(CH₂CH₃) (CH₂CH₂CH₃)), 2-methyl-2-pentyl (—C(CH₃)₂ CH₂CH₂CH₃), 3-methyl-2-pentyl (—CH(CH₃)CH(CH₃) CH₂CH₃), 4-methyl-2-pentyl (—CH(CH₃)CH₂CH(CH₃) 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C (CH₃)₂CH(CH₃)₂), 3,3-dimethyl-2-butyl (—CH(CH₃)C (CH₃)₃), 2,3-dimethyl-1-butyl (—CH₂CH(CH₃)CH(CH₃) CH₃), 2,2-dimethyl-1-butyl (—CH₂C(CH₃)₂CH₂CH₃), 3,3-dimethyl-1-butyl (—CH₂CH₂C(CH₃)₃), 2-methyl-1-pentyl (—CH₂CH(CH₃)CH₂CH₂CH₃), 3-methyl-1-pentyl (—CH₂CH₂CH(CH₃)CH₂CH₃), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$ alkylamino or $C_{x-y}$alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF=CF₂, —CCl=CH₂, —CBr=CH₂, —CHFCH₂CH₃, —CHFCH₂CF₃ etc.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl.

Corresponding groups are an example:
cyclohexyl

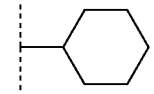

Spirocycle is a spiro-hydrocarbon ring one carbon atom (spiroatom) belongs to two rings together.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl and naphthyl.

The above definition of aryl also applies if aryl is part of another (combined) group as for example in arylamino, aryloxy or arylalkyl.

Heterocyclyl denotes ring systems, which are derived from the previously defined cycloalkyl or spirocycle by replacing one or more of the groups —CH$_2$— independently of one another in the hydrocarbon rings by the groups —O—, —S— or —NH—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide).

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuranyl, tetrahydropyranyl, piperidinyl, piperazinyl, pyrrolidinyl, morpholinyl,
or the following heterocyclic spirocycles

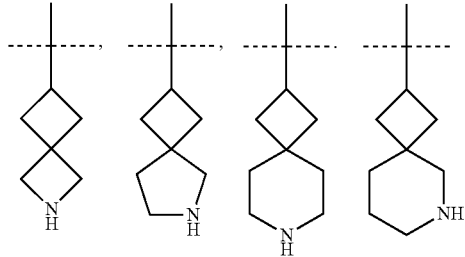

Heteroaryl denotes monocyclic heteroaromatic rings or polycyclic rings with at least one heteroaromatic ring, which compared with the corresponding aryl or cycloalkyl, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are, pyridinyl, pyridazinyl, pyrimidinyl, pyrazinyl, benzoxazolyl, indolyl, isoindolyl, benzofuranyl, benzimidazolyl, benzothiazolyl, and the like.

Heteroatoms may optionally be present in all the possible oxidation stages (sulphur→sulphoxide —SO—, sulphone —SO$_2$—; nitrogen→N-oxide).

Carbocycles include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

All cyclic and acyclic systems defined in this section hereinabove shall be understood to be optionally partially or fully halogenated where possible and unless otherwise indicated.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below: In a representation such as for example

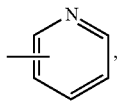

the solid line means that the ring system may be attached to the molecule via the carbon atom 1, 2 or 3, and is thus equivalent to the following representation

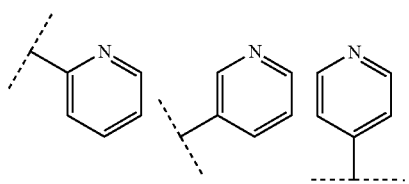

By a therapeutically effective amount for the purposes of this invention is meant a quantity of substance that is capable of obviating symptoms of illness or alleviating these symptoms, or which prolong the survival of a treated patient.

| List of abbreviations | |
|---|---|
| Ac | Acetyl |
| ACN | Acetonitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DME | 1,2-dimethoxyethane |
| DMF | N,N-dimethylformamide |
| DMSO | Dimethylsulphoxide |
| dppf | 1,1'-bis(diphenylphosphino)ferrocene |
| EDC | 1-Ethyl-3-(3-dimethylaminopropyl)carbodiimide |
| ESI | electron spray ionization |
| Et | Ethyl |
| Et$_2$O | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |

-continued

| List of abbreviations | |
|---|---|
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf (R$_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |

Features and advantages of the present invention will become apparent from the following detailed examples which illustrate the fundamentals of the invention by way of example without restricting its scope:

Preparation of the Compounds According to the Invention
General Synthetic Methods Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns:

a) Waters Sunfire OBD C18 5 μm 30×150 mm column
b) Waters XBridge OBD C18 5 μm 30×150 mm column
c) Waters ODB C8 5 μm 19×150 mm column.
d) Waters Atlantis ODB C18 5 μm 19×50 mm column.
e) Waters Atlantis T3 OBD 5 μm 30×100 mm column
f) Phenomenex Gemini Axia C18 5 μm 30×100 mm column HPLC Methods:
Analytical LC/MS Analysis Method A:
Column: Thermo Scientific, Aquasil C18, 50×2.1 mm, 5 μm column
Gradient:

| Time (min) | 0.1% Formic Acid in Water | 0.1% Formic Acid in CAN | Flow (ml/min) |
|---|---|---|---|
| 0 | 90 | 10 | 0.5 |
| 0.5 | 90 | 10 | 0.5 |

153
-continued

| Time (min) | 0.1% Formic Acid in Water | 0.1% Formic Acid in CAN | Flow (ml/min) |
|---|---|---|---|
| 1.5 | 1 | 99 | 0.5 |
| 2.5 | 1 | 99 | 0.5 |
| 3.3 | 90 | 10 | 0.5 |
| 4.0 | 90 | 10 | 0.5 |

Analytical LC/MS Analysis Method B:
Column: Waters BEH 2.1×50 mm C18 1.7 μm column
Gradient:

| Time (min) | 95% Water/ 5% ACN (0.05% TFA) | ACN (0.05% TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme Ia and Ib below.

Scheme 1a:

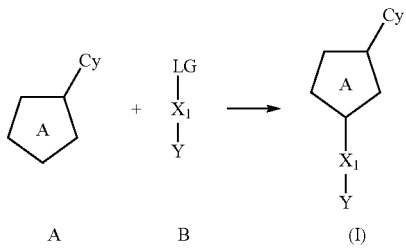

A          B          (I)

In scheme Ia, a heterocycle A is treated with a suitable base and reacted with an $X_1$-Y group containing a leaving group (LG) B to afford the compound of general formula (I).

Scheme 1b:

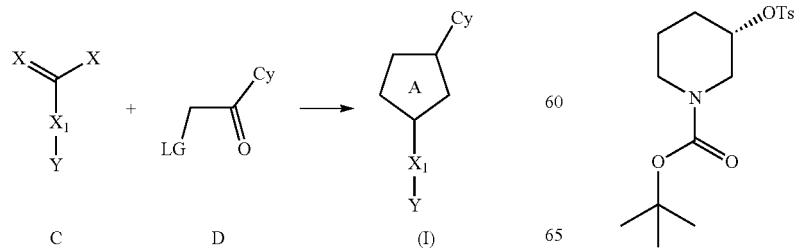

C          D          (I)

In scheme Ib, C (where X=O, N, S, or $NH_2$) is condensed with D to afford the compound of general formula (I).

SYNTHETIC EXAMPLES

Method 1

Synthesis of Intermediate I-1

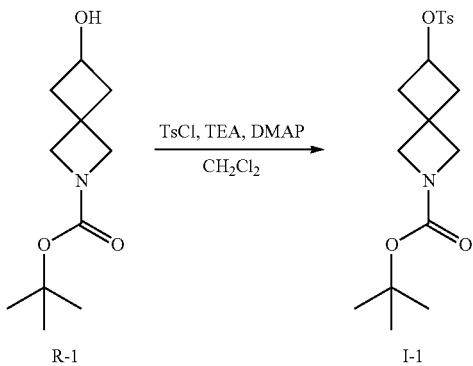

R-1          I-1

A solution of R-1 (5.0 g, 23 mmol) in $CH_2Cl_2$ is treated with TEA (6.5 mL, 47 mmol) and DMAP (0.57 g, 4.7 mmol). The mixture is stirred for 24 h then concentrated in vacuo. The residue is dissolved in EtOAc and washed with saturated aqueous ammonium chloride and brine. The organics are collected and volatiles are removed in vacuo. The crude residue is triturated with $Et_2O$ and solid filtered and collected to afford I-1 (5.6 g, 65%) m/z 367.9 [M+].

The following intermediates were prepared in a similar manner

| Structure | Intermediate | m/z |
|---|---|---|
| ![OTs spiro piperidine Boc] | I-2 | 396.3 [M + H] |
| ![OTs piperidine Boc] | I-3 | 356.0 [M + H] |

Method 2

Synthesis of Intermediate I-4 and Separation of Diastereomers I-5 and I-6

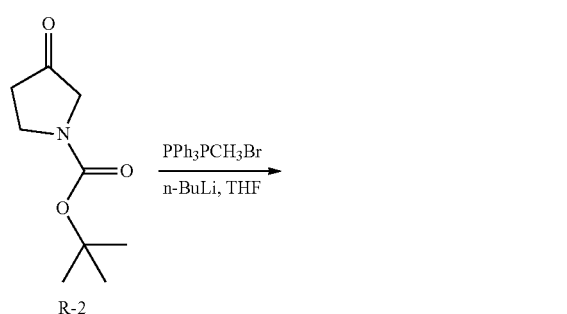

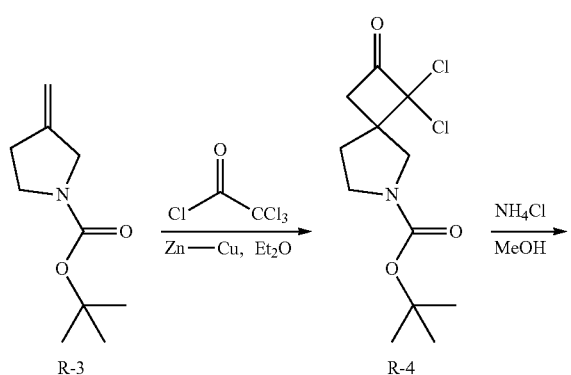

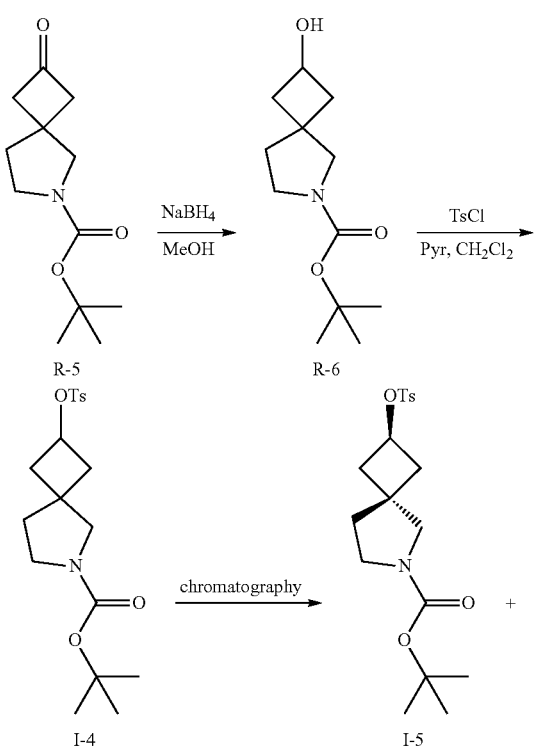

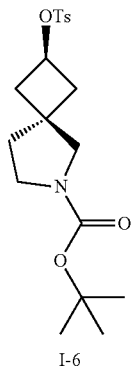

I-6

To a solution of PPh₃CH₃Br (578 g, 1.62 mol) in THF (3.5 L) is added a solution of n-BuLi (600 mL, 1.5 mol) at −78° C. under N₂. The mixture is stirred at 0° C. for 1 h then R-2 (200 g, 1.08 mol) in THF (2.0 L) is added to the reaction mixture at 0° C. The mixture is allowed to warm to ambient temperature, stirred for 1 h, then poured into H₂O and extracted with EtOAc. The organic layers are washed with brine, dried with Na₂SO₄, concentrated and purified by flash chromatography (SiO₂, Hep to 25% EtOAc in Hep) to give compound R-3 (70 g, 36%).

To a solution of R-3 (20 g, 109 mmol) in Et₂O (150 mL) is added Zn—Cu (56.2 g, 436 mmol) at 10° C. under N₂. Trichloroacetyl chloride (39.7 g, 218 mmol) in DME (150 mL) is added. The mixture is allowed to warm to ambient temperature and stirred for 2 days. The mixture is treated with aqueous NaHCO₃ and extracted with EtOAc. The organic layers are washed with brine, dried with Na₂SO₄, concentrated and purified by flash chromatography (SiO₂, Hep to 25% EtOAc in Hep) to give R-4 (11 g, 34%).

To a solution of R-4 (35.5 g, 121 mmol) in saturated NH₄Cl (64.7 g, 1.21 mol) in MeOH (400 mL) is added Zn (79.1 g, 1.21 mol). The mixture is stirred at ambient temperature for 8 h. The mixture is treated with H₂O and extracted with EtOAc. The organic layers are washed with brine, dried with Na₂SO₄, concentrated and purified by flash chromatography (SiO₂, Hep to 25% EtOAc in Hep) to afford R-5 (19 g, 69%).

To the mixture of R-5 (19 g, 84.3 mmol) in THF (200 mL) is added NaBH₄ (12.8 g, 337.2 mmol) at 0° C. and then stirred at ambient temperature for 6 h. The mixture is treated with MeOH and H₂O, then extracted with EtOAc. The organic layers are washed with brine, dried with Na₂SO₄, concentrated and purified by flash chromatography (SiO₂, Hep to 50% EtOAc in Hep) to yield R-6 (12 g, 63%).

To the mixture of R-6 (22 g, 96.8 mmol) and pyridine (23.2 g, 290.4 mmol) in CH₂Cl₂ (300 mL) is added TsCl (27.7 g, 145.2 mmol) at 0° C. and then stirred at ambient temperature overnight. The mixture is treated with H₂O and extracted with EtOAc. The organic layers are washed with brine, dried with Na₂SO₄, concentrated and purified by flash chromatography (SiO₂, Hep to 40% EtOAc in Hep) to give I-4 (26.6 g, 72%) m/z 382.2 [M+H]. I-4 is separated by flash chromatography (SiO₂, Hep to 40% EtOAc in Hep) to give diastereomers I-5 (m/z 382.2 [M+H]) and I-6 (m/z 382.2 [M+H]).

Method 3

Synthesis of Intermediate I-8

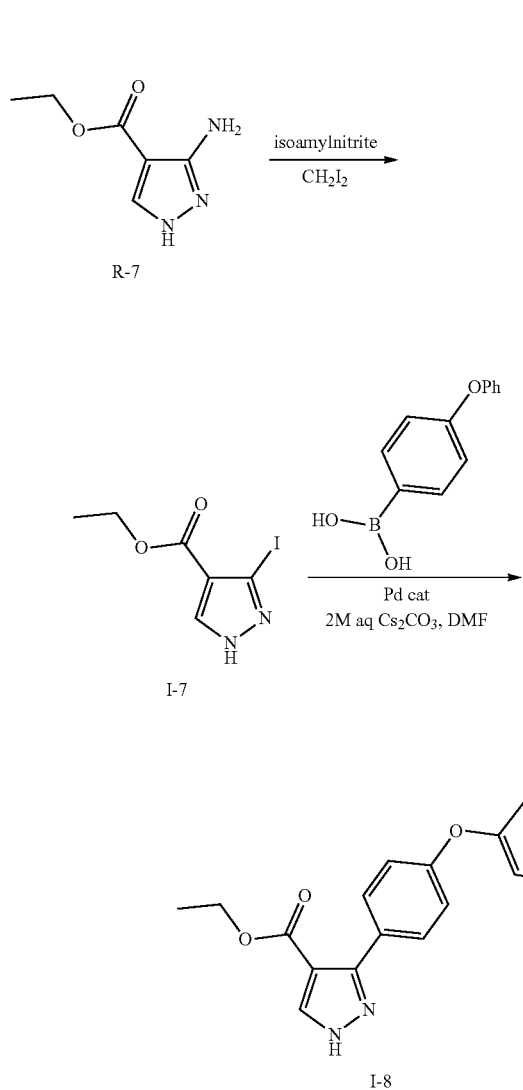

To a solution of R-7 (15.0 g, 97 mmol) in CH$_2$I$_2$ (350 mL) is added isoamylnitrite (58.7 g, 580 mmol). The solution is stirred for 15 min at ambient temperature then heated at 70° C. for 2 h. The mixture is cooled to ambient temperature then partitioned between EtOAc and aqueous sodium bisulfite. The organics are collected, dried over MgSO$_4$, filtered, and concentrated in vacuo. The crude is purified by flash chromatography (SiO$_2$, Hep to 50% EtOAc in Hep) to give the I-7 (13.1 g, 51%) m/z 266.8 [M+H].

A solution of I-7 (2.0 g, 7.5 mmol), 4-phenoxyphenylboronic acid (2.0 g, 9.3 mmol), and bis(di-tert-butyl(4-dimethylaminophenyl)phosphine) dichloropalladium(II) (1.5 g, 2.1 mmol) in DMF (20 mL) and 2M aqueous Cs$_2$CO$_3$ (10 mL) is heated at 120° C. for 2 h. The mixture is cooled to ambient temperature then partitioned between EtOAc and aqueous NH$_4$Cl. The organics are collected, dried over MgSO$_4$, filtered, and concentrated in vacuo. The crude is purified by flash chromatography (SiO$_2$, 10-30% EtOAc in Hep) to give I-8 (1.6 g, 69%). m/z 309.1 [M+H].

Method 4

Synthesis of Intermediate I-9

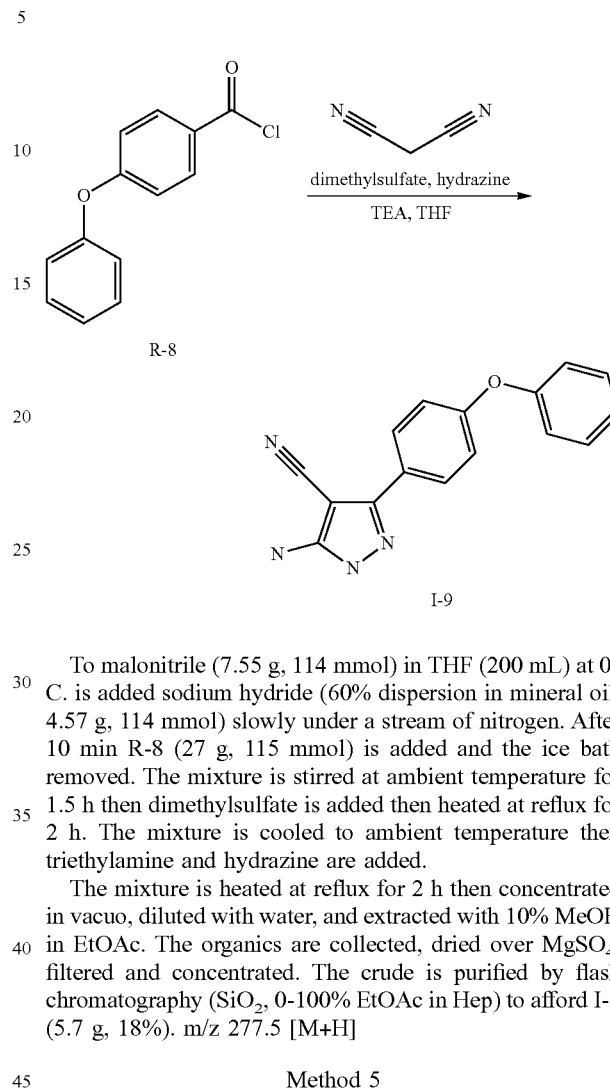

To malonitrile (7.55 g, 114 mmol) in THF (200 mL) at 0° C. is added sodium hydride (60% dispersion in mineral oil, 4.57 g, 114 mmol) slowly under a stream of nitrogen. After 10 min R-8 (27 g, 115 mmol) is added and the ice bath removed. The mixture is stirred at ambient temperature for 1.5 h then dimethylsulfate is added then heated at reflux for 2 h. The mixture is cooled to ambient temperature then triethylamine and hydrazine are added.

The mixture is heated at reflux for 2 h then concentrated in vacuo, diluted with water, and extracted with 10% MeOH in EtOAc. The organics are collected, dried over MgSO$_4$, filtered and concentrated. The crude is purified by flash chromatography (SiO$_2$, 0-100% EtOAc in Hep) to afford I-9 (5.7 g, 18%). m/z 277.5 [M+H]

Method 5

Synthesis of Intermediate I-10

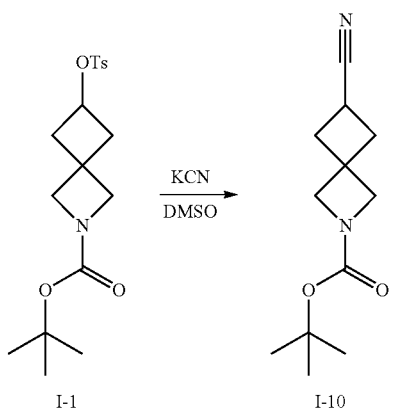

To a solution of I-1 (200 mg, 0.54 mmol) in DMSO (2.5 mL) was added KCN (71 mg, 1.1 mmol). The mixture was heated at 100° C. for 18 h then cooled to ambient temperature and partitioned between EtOAc and water. The organics were collected, dried over MgSO$_4$, filtered and concentrated in vacuo to afford I-10 (quant, 120 mg). m/z 223.1 [M+H]

The following intermediates were prepared in a similar manner

| Structure | Intermediate | m/z |
|---|---|---|
| 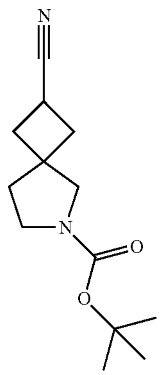 [SMILES: CC(C)(C)OC(=O)N1CCC2(CC(C#N)C2)C1] | I-11 | 181.0 [M − tBu] |
| 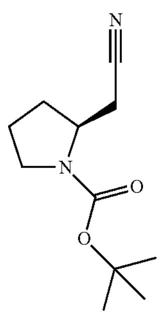 | I-12 | 211.1 [M + H] |
| 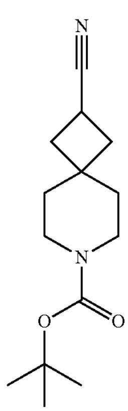 [SMILES: CC(C)(C)OC(=O)N1CCC2(CC1)CC(C#N)C2] | I-13 | 195.4 [M − tBu] |

Method 6

Synthesis of Intermediate I-14

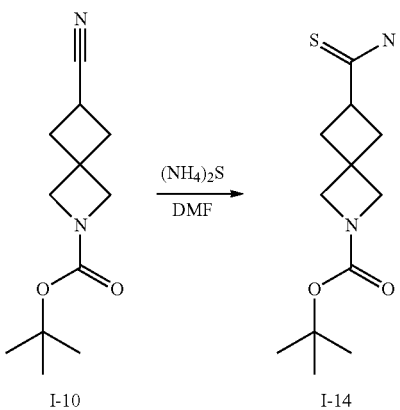

I-10    I-14

To a solution of I-10 (250 mg, 1.1 mmol) in DMF (2 mL) is added 20% (w/w) aqueous (NH$_4$)$_2$S (2 mL, 5.9 mmol). The mixture is stirred at ambient temperature for 17 h then diluted with water. The resulting white solid is filtered and collected to give I-14 (160 mg, 55%). m/z 257.0 [M+H]

The following intermediates were prepared in a similar manner

| Structure | Intermediate | m/z |
|---|---|---|
| 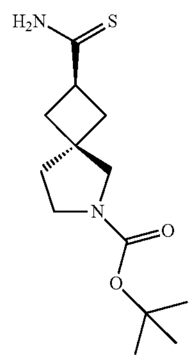 [SMILES: CC(C)(C)OC(=O)N1CC[C@]2(C1)C[C@@H](C(N)=S)C2] | I-15 | 271.1 [M + H] |
| 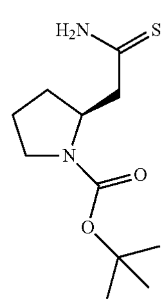 [SMILES: CC(C)(C)OC(=O)N1CCC[C@H]1CC(N)=S] | I-16 | 189.0 [M − tBu] |

| Structure | Intermediate | m/z |
|---|---|---|
| 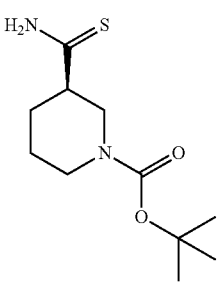 [SMILES: CC(C)(C)OC(=O)N1CCC[C@@H](C(N)=S)C1] | I-17 | 245.0 [M + H] |
| 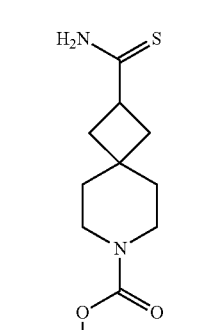 | I-18 | 285.1 [M + H] |

Method 7

Synthesis of Intermediate I-19

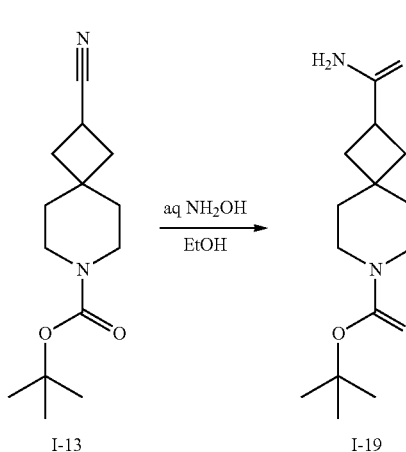

A solution of I-13 (422 mg, 1.69 mmol) in EtOH (8.4 mL) is treated with 50% (w/w) aqueous hydroxylamine (1.1 mL, 16.9 mmol). The solution is heated at 70° C. for 2 h then volatiles are removed in vacuo to afford I-19 (478 mg, quant) m/z 284.1 [M+H].

The following intermediates were prepared in similar manner

| Structure | Intermediate | m/z |
|---|---|---|
| 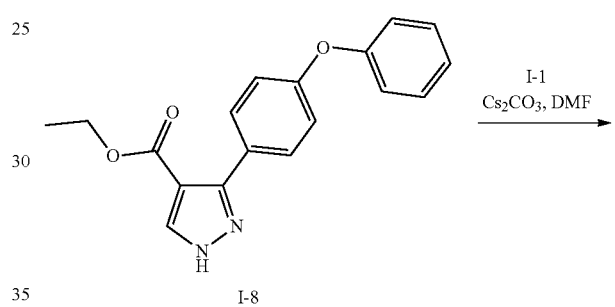 | I-20 | 244.1 [M + H] |

Method 8

Synthesis of Intermediate I-21

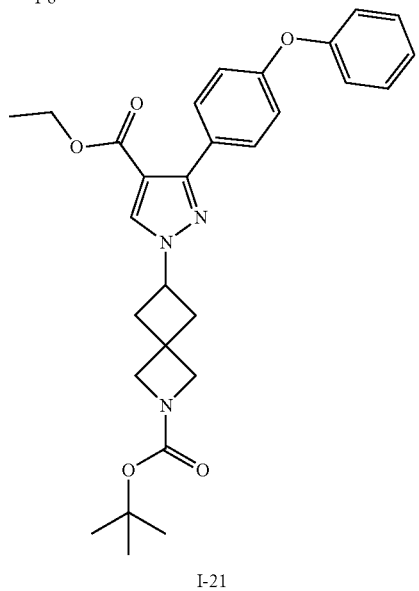

To a solution of I-8 (200 mg, 0.65 mmol) and $Cs_2CO_3$ (423 mg, 1.30 mmol) in DMF (3 mL) is added I-1 (262 mg, 0.71 mmol). The mixture is heated at 60° C. for 18 h then concentrated in vacuo. The residue is purified by flash chromatography ($SiO_2$, Hep to 50% EtOAc in Hep) to give I-21 (217 mg, 66%) m/z 504.2 [M+H].

The following intermediates were prepared in similar fashion:

| Structure | Intermediate | m/z |
|---|---|---|
| 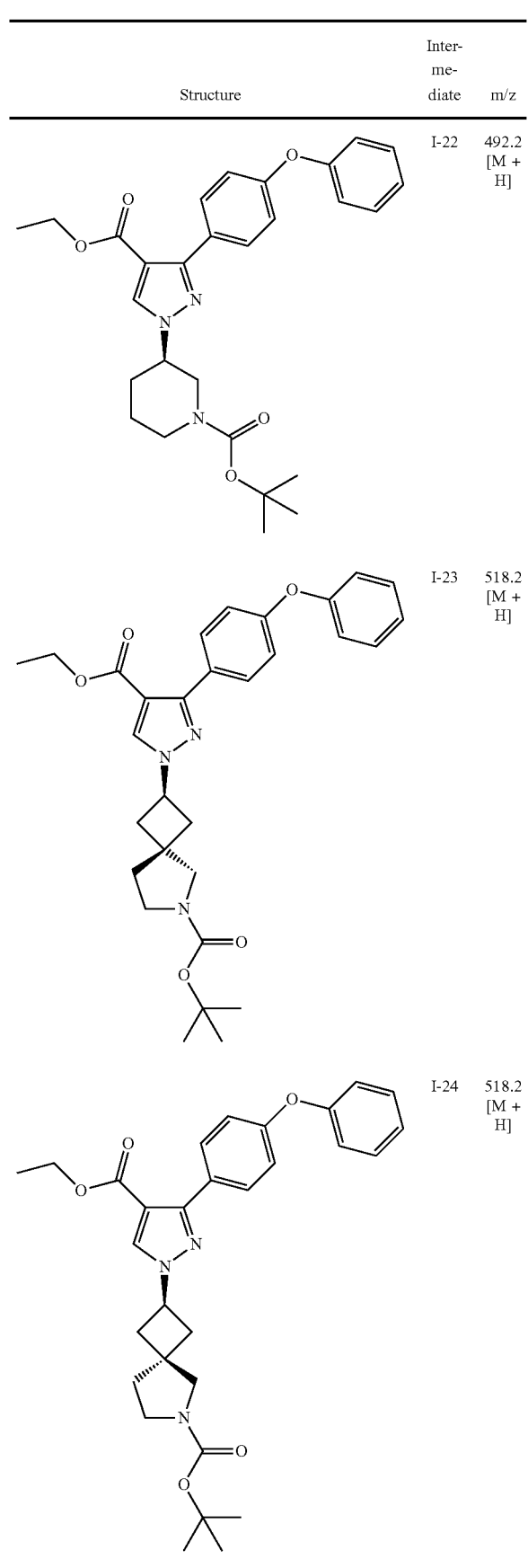 | I-22 | 492.2 [M + H] |
| 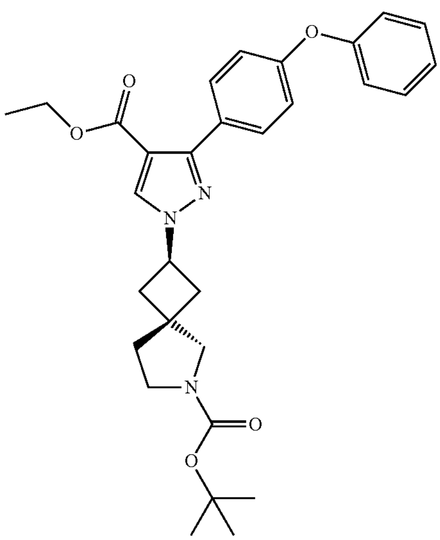 | I-23 | 518.2 [M + H] |
| 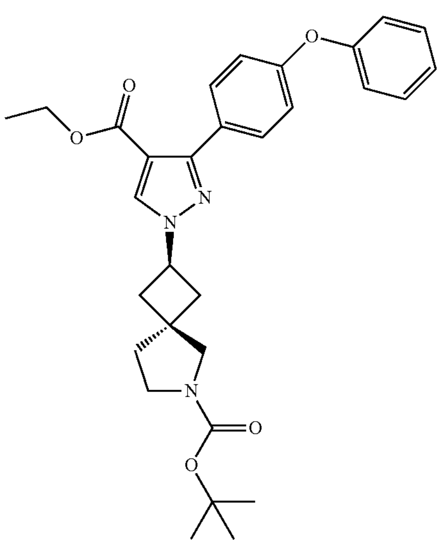 [SMILES: CCOC(=O)c1cn([C@H]2C[C@]3(CCN(C(=O)OC(C)(C)C)C3)C2)nc1-c1ccc(Oc2ccccc2)cc1] | I-24 | 518.2 [M + H] |
-continued
| Structure | Intermediate | m/z |
|---|---|---|
| 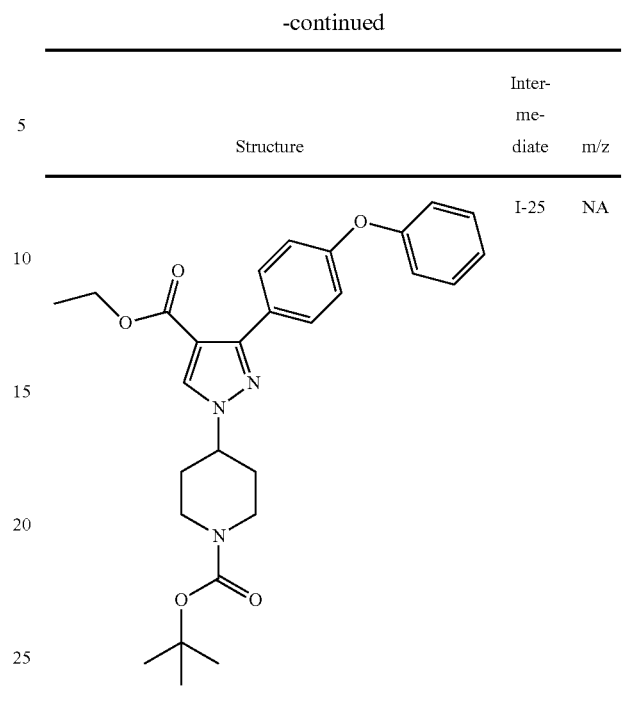 | I-25 | NA |
Method 9
Synthesis of Intermediate I-26
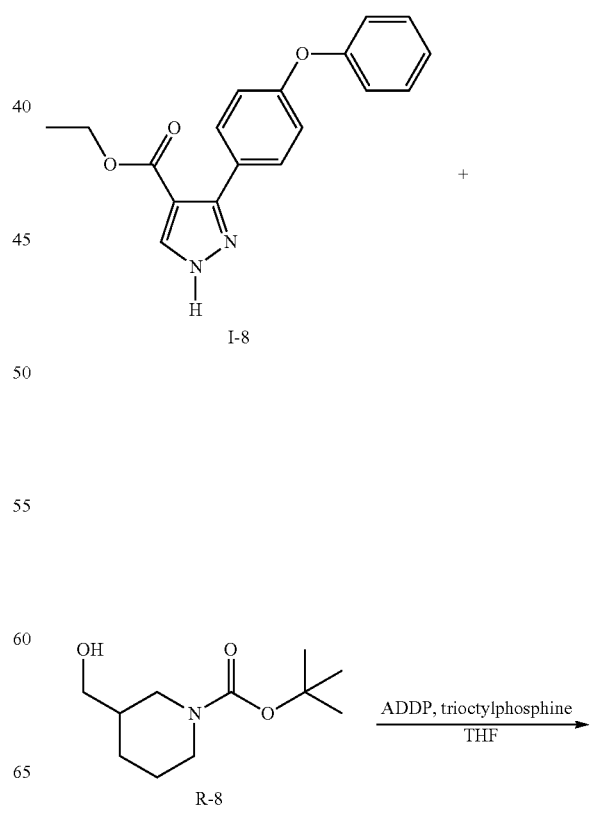

165
-continued

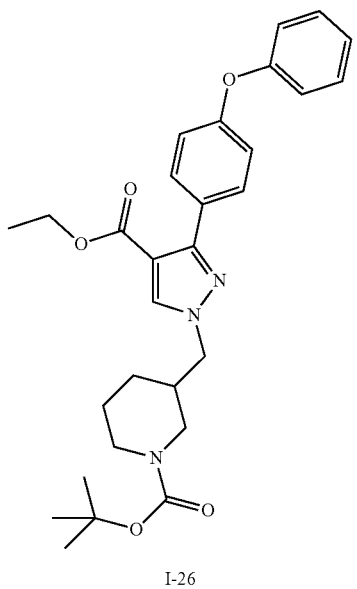

I-26

To a solution of I-6 (800 mg, 2.6 mmol) in THF (40 mL) is added R-8 (650 mg, 3.0 mmol), tri-n-octyl phosphine (3.0 g, 8.0 mmol), and ADDP (1,1'-(azodicarbonyl)dipiperidine) (2.1 g, 8.2 mmol). The mixture is stirred for 48 h then concentrated in vacuo. The residue is partitioned between saturated aqueous NH$_4$Cl and EtOAc. The organics are washed with brine, dried over Na$_2$SO$_4$, filtered, and concentrated in vacuo. The crude is purified by flash chromatography (SiO$_2$, Hep to 30% EtOAc in Hep) to give I-24 (1.1 g, 84%) m/z 506.1 [M+H].

The following intermediates are prepared in similar fashion:

166
-continued

| Structure | Intermediate | m/z |
|---|---|---|
| 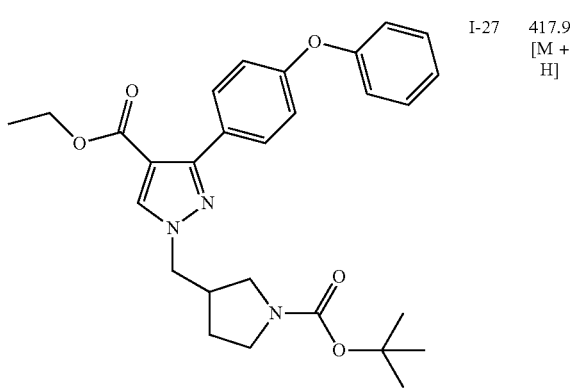 | I-25 | NA |
| 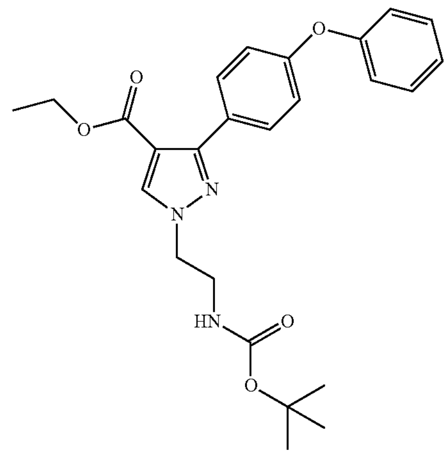 [SMILES: CCOC(=O)c1cn(CCNC(=O)OC(C)(C)C)nc1-c1ccc(Oc2ccccc2)cc1] | I-26 | NA |
| 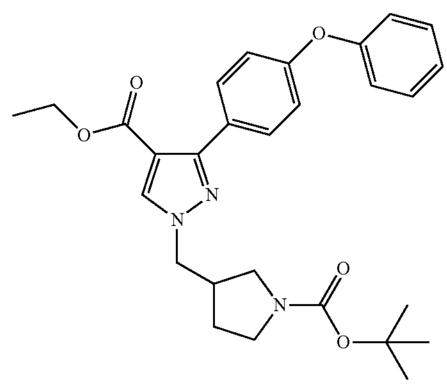 | I-27 | 417.9 [M + H] |
| 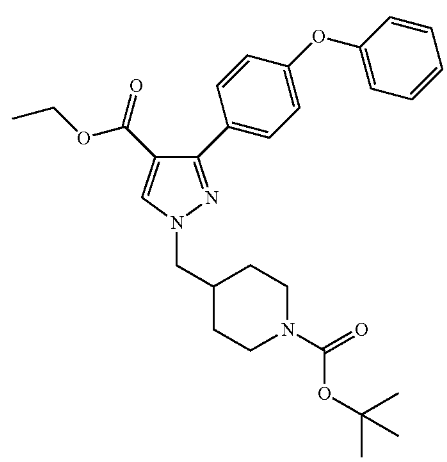 [SMILES: CCOC(=O)c1cn(CC2CCN(C(=O)OC(C)(C)C)CC2)nc1-c1ccc(Oc2ccccc2)cc1] | I-28 | NA |

Method 10

Synthesis of Intermediate I-30

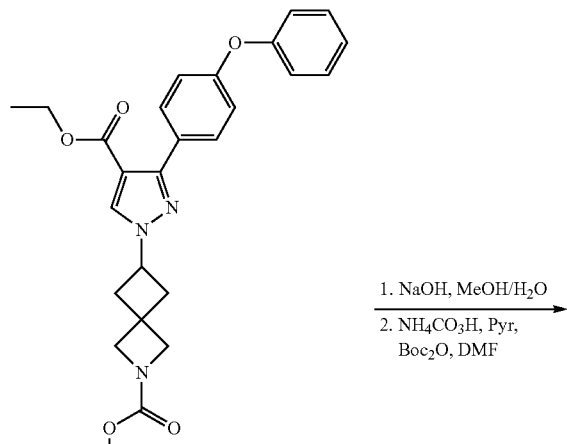

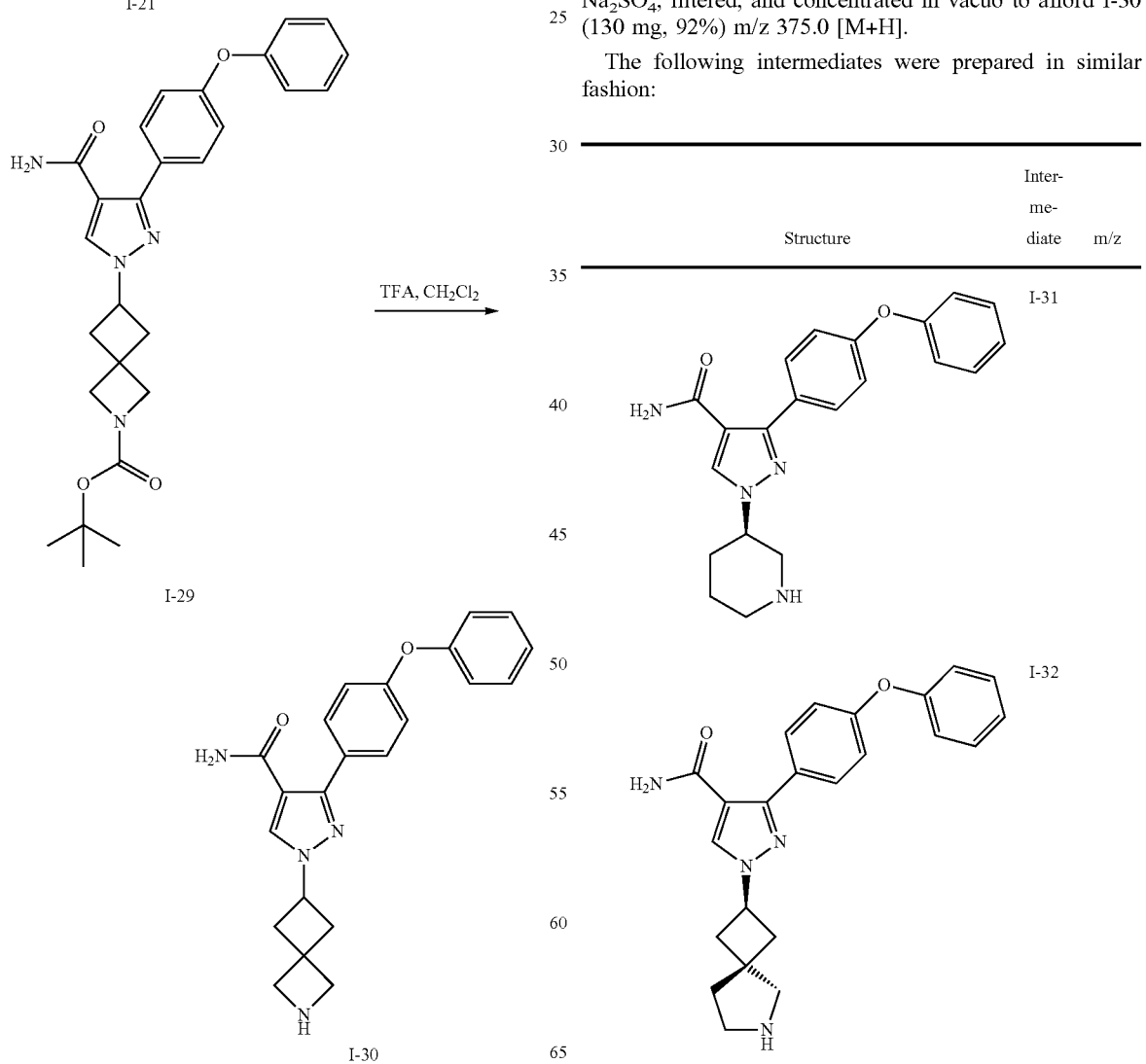

A solution of I-21 (260 mg, 0.52 mmol) in 1:1 dioxane/water (8 mL) is treated with LiOH (120 mg, 5.0 mmol). The mixture is heated at reflux for 2 h then volatiles are removed in vacuo. The residue is acidified to pH=4 with 2M aqueous HCl, extracted with EtOAc, washed with brine, dried over $Na_2SO_4$, filtered, and concentrated in vacuo. The residue is dissolved in DMF (4 mL) and treated with pyridine (80 uL, 1.0 mmol) and Boc anhydride (80 mg, 1.0 mmol). The solution is stirred for 10 min then ammonium bicarbonate (95 mg, 1.2 mmol) is added. The mixture is stirred for 16 h then volatiles are removed in vacuo. The residue is partitioned between EtOAc and saturated aqueous $NH_4Cl$. The organics are washed with brine, dried over $Na_2SO_4$, filtered, and concentrated in vacuo. The residue is purified by flash chromatography ($SiO_2$, 20-80% EtOAc in Hep, then 20% MeOH in $CH_2Cl_2$) to give I-29 (180 mg, 75%) m/z 475.0 [M+H].

To a stirred solution of I-29 (180 mg, 0.38 mmol) in $CH_2Cl_2$ (3 mL) is added TFA (2 mL). The solution is stirred at ambient temperature for 3 h then volatiles are removed in vacuo. The residue is partitioned between saturated aqueous $NaHCO_3$ and EtOAc. The organics are collected, dried over $Na_2SO_4$, filtered, and concentrated in vacuo to afford I-30 (130 mg, 92%) m/z 375.0 [M+H].

The following intermediates were prepared in similar fashion:

169
-continued
| Structure | Intermediate | m/z |
|---|---|---|
| 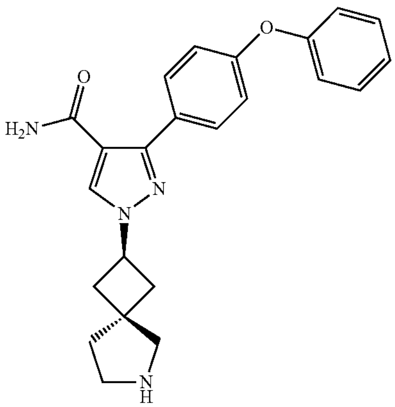 [SMILES: NC(=O)c1cn([C@H]2C[C@]3(CCNC3)C2)nc1-c1ccc(Oc2ccccc2)cc1] | I-33 | |
| 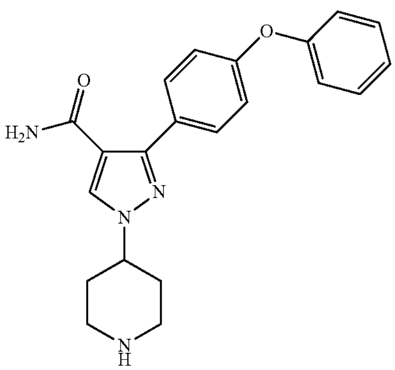 [SMILES: NC(=O)c1cn(C2CCNCC2)nc1-c1ccc(Oc2ccccc2)cc1] | I-34 | |
| 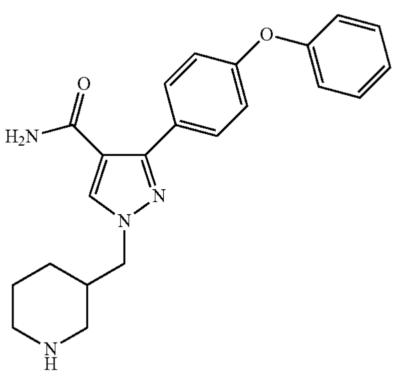 [SMILES: NC(=O)c1cn(CC2CCCNC2)nc1-c1ccc(Oc2ccccc2)cc1] | I-35 | |
| 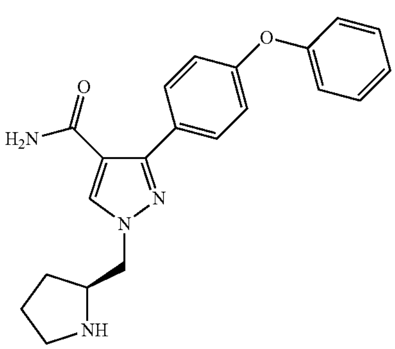 [SMILES: NC(=O)c1cn(C[C@@H]2CCCN2)nc1-c1ccc(Oc2ccccc2)cc1] | I-36 | |
170
-continued
| Structure | Intermediate | m/z |
|---|---|---|
| 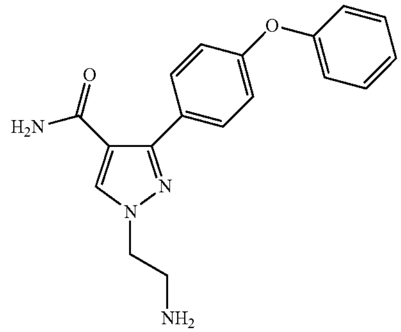 [SMILES: NCCn1cc(C(N)=O)c(-c2ccc(Oc3ccccc3)cc2)n1] | I-37 | |
| 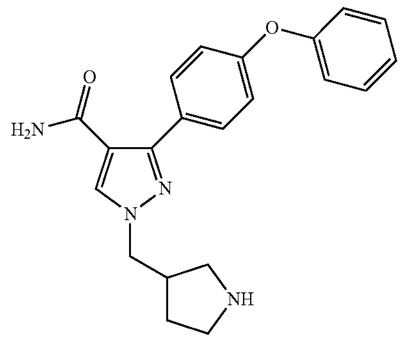 [SMILES: NC(=O)c1cn(CC2CCNC2)nc1-c1ccc(Oc2ccccc2)cc1] | I-38 | |
| 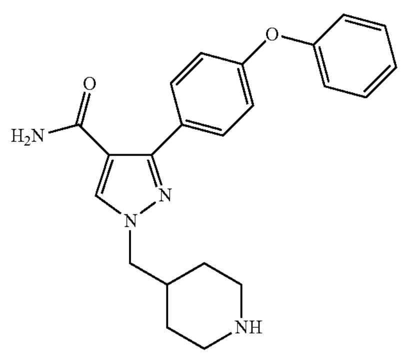 [SMILES: NC(=O)c1cn(CC2CCNCC2)nc1-c1ccc(Oc2ccccc2)cc1] | I-39 | NA |
Method 11
Synthesis of Intermediate I-41
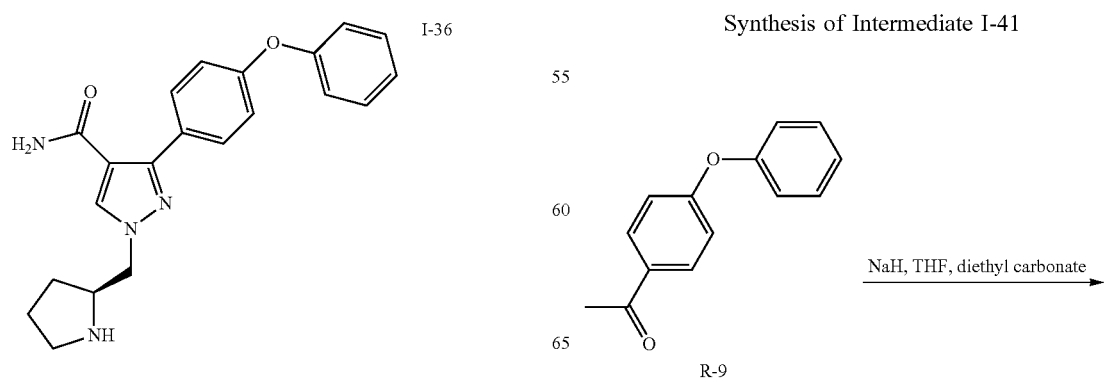

-continued

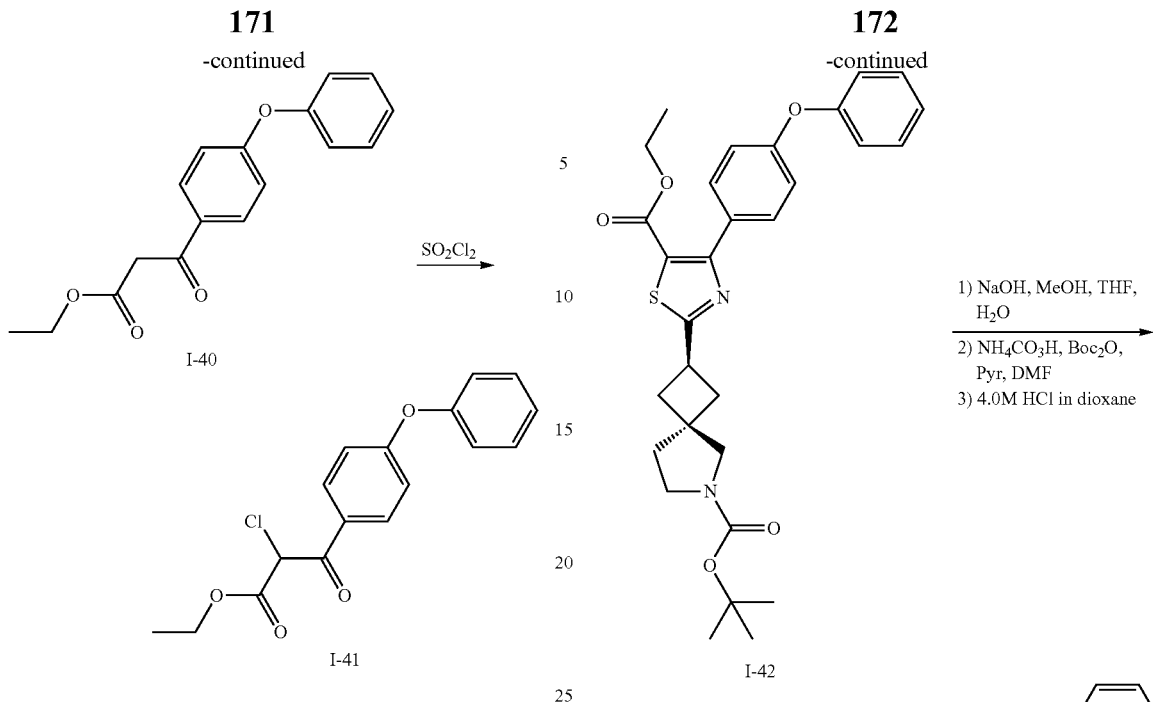

To a solution of R-9 (5.00 g, 23.6 mmol) in THF (50 mL) is added a 60% dispersion of sodium hydride in mineral oil (1.41 g, 35.1 mmol). The mixture is stirred for 5 min at ambient temperature then diethyl carbonate (5.7 mL, 47.4 mmol). The reaction is stirred for 30 min at ambient temperature then heated at reflux for 2 h. The mixture is cooled to ambient temperature then partitioned between saturated aqueous NH$_4$Cl and EtOAc. The organics are collected and concentrated in vacuo to afford a residue that is purified by flash chromatography (SiO$_2$, Hep to 70% EtOAc in Hep) to give I-40 (6.2 g, 93%) m/z 285.1 [M+H].

To a cold (0° C.) solution of I-40 (5.2 g, 18.3 mmol) in CH$_2$Cl$_2$ (46 mL) is added SO$_2$Cl$_2$ (1.5 mL, 18.3 mmol). The mixture is allowed to warm to ambient temperature and stirred for 30 min then treated with water, extracted with CH$_2$Cl$_2$, dried over Na$_2$SO$_4$, filtered, and concentrated in vacuo to afford I-41 (quant) m/z 318.9 [M+H].

Method 12

Synthesis of Intermediate I-43

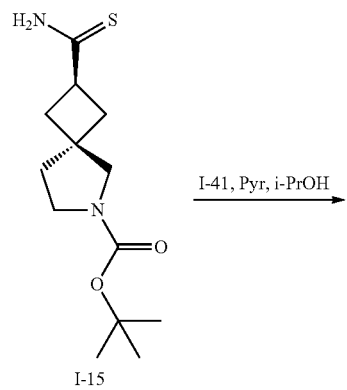

A solution of I-15 (400 mg, 1.48 mmol) and I-41 (943 mg, 2.96 mmol) in i-PrOH (15 mL) is treated with pyridine (0.36 mL, 4.44 mmol). The mixture is heated at 60° C. for 3 days then volatiles are removed in vacuo. The residue is purified by flash chromatography (SiO$_2$, Hep to 40% EtOAc in Hep) to give I-42 (240 mg, 30%) m/z 535.2 [M+H].

A solution of I-42 (240 mg, 0.45 mmol) in MeOH (3 mL), THF (1 mL), and 5M aqueous NaOH (0.5 mL) is heated at 60° C. for 3 h. The mixture is cooled to ambient temperature then acidified to pH=1 with 6M aqueous HCl. The mixture is extracted with CH$_2$Cl$_2$ then filtered through a phase Separator® then volatiles are removed in vacuo. The residue is dissolved in DMF (2 mL) and treated with pyridine (324 mg, 4.1 mmol), Boc anhydride (327 mg, 0.45 mmol), followed by ammonium bicarbonate (215 mg, 2.72 mmol). The mixture is stirred for 3 h then volatiles are removed in vacuo to afford a residue that is purified by flash chromatography (SiO$_2$, CH$_2$Cl$_2$ to 5% MeOH in CH$_2$Cl$_2$). The purified material is dissolved in CH$_2$Cl$_2$ (5 mL) and treated with 4.0M HCl in dioxane (1.1 mL). The mixture is stirred for 1 h then volatiles are removed in vacuo to afford a residue that is purified by flash chromatography (SiO$_2$, CH$_2$Cl$_2$ to 20% MeOH in CH$_2$Cl$_2$ containing 2.5% TEA) to give I-43 (134 mg, 73%) m/z 405.9 [M+H].

The following compounds are made in similar fashion:

| Structure | Intermediate | m/z |
|---|---|---|
| 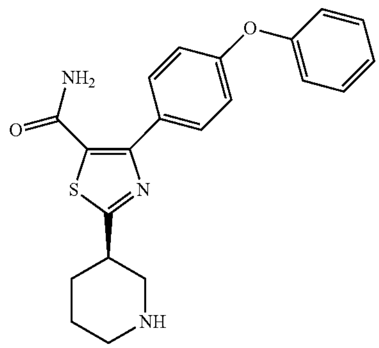 [SMILES: NC(=O)c1sc([C@@H]2CCCNC2)nc1-c1ccc(Oc2ccccc2)cc1] | I-44 | 380.8 [M + H] |
| 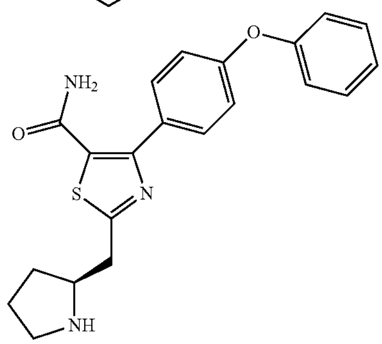 | I-45 | 380.4 [M + H] |
| 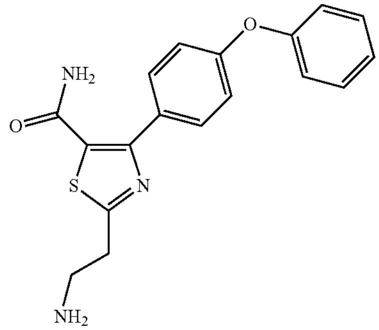 [SMILES: NCCc1nc(-c2ccc(Oc3ccccc3)cc2)c(C(N)=O)s1] | I-46 | NA |

Method 13

Synthesis of Intermediate I-46

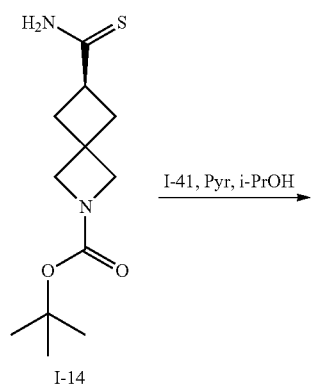

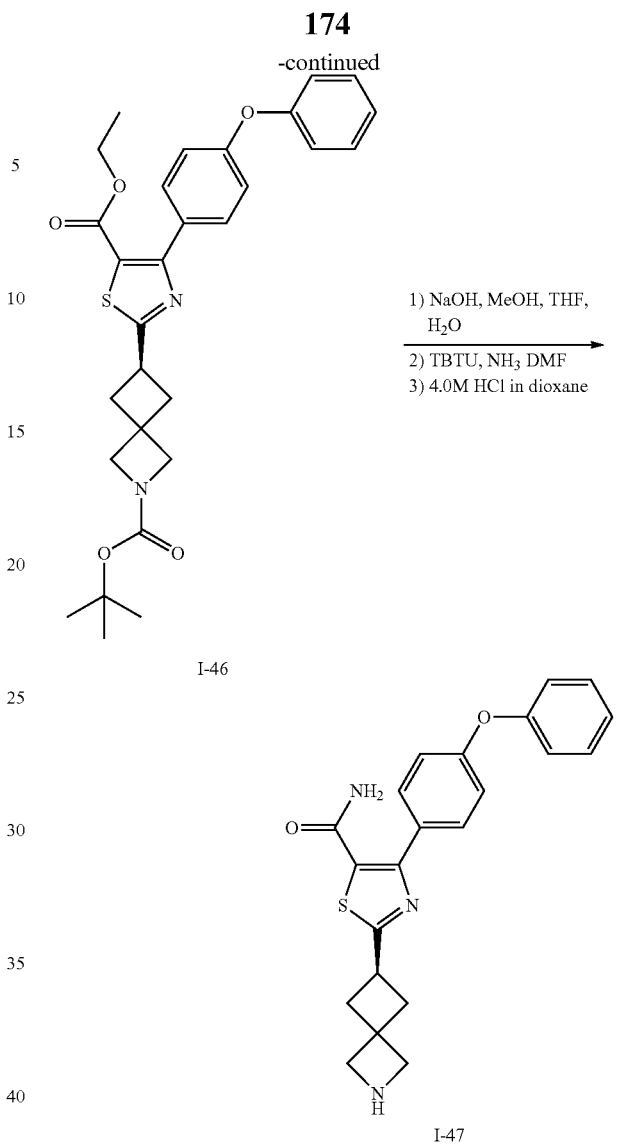

To a solution of I-14 (160 mg, 0.62 mmol) and I-41 (298 mg, 0.94 mmol) in i-PrOH (6.2 mL) is added pyridine (0.15 mL, 1.9 mmol). The solution is heated at 70° C. for 24 h then volatiles are removed in vacuo. The crude is purified by flash chromatography (SiO$_2$, Hep to 40% EtOAc in Hep) to give I-46 (144 mg, 44%) m/z 521.2 [M+H].

A solution of I-46 (144 mg, 0.28 mmol) in MeOH (2 mL) and 3M aqueous NaOH (2 mL) is heated at 65° C. for 3 h then cooled to ambient temperature. The solid is filtered, collected, and dried then dissolved in DMF (2 mL) and treated with TBTU (71 mg, 0.22 mmol). The mixture is stirred for 15 min then treated with 7M ammonia in MeOH (7 mL). The mixture is stirred for 20 min then volatiles are removed in vacuo. The residue is partitioned between water and EtOAc and organics are collected and concentrated. The crude is purified by flash chromatography (Hep to EtOAc). The resulting compound is dissolved in CH$_2$Cl$_2$ (2 mL) and treated with TFA (1 mL). The reaction mixture is stirred for 2 h then volatiles are removed in vacuo. The crude is partitioned between CH$_2$Cl$_2$ and 10% (w/w) aqueous Na$_2$CO$_3$ and CH$_2$Cl$_2$. The organics are collected and filtered through a phase Separator® to afford after removal of the volatiles I-47 (58 mg, 53%) m/z 392.1 [M+H].

Method 14

Synthesis of Intermediate I-51

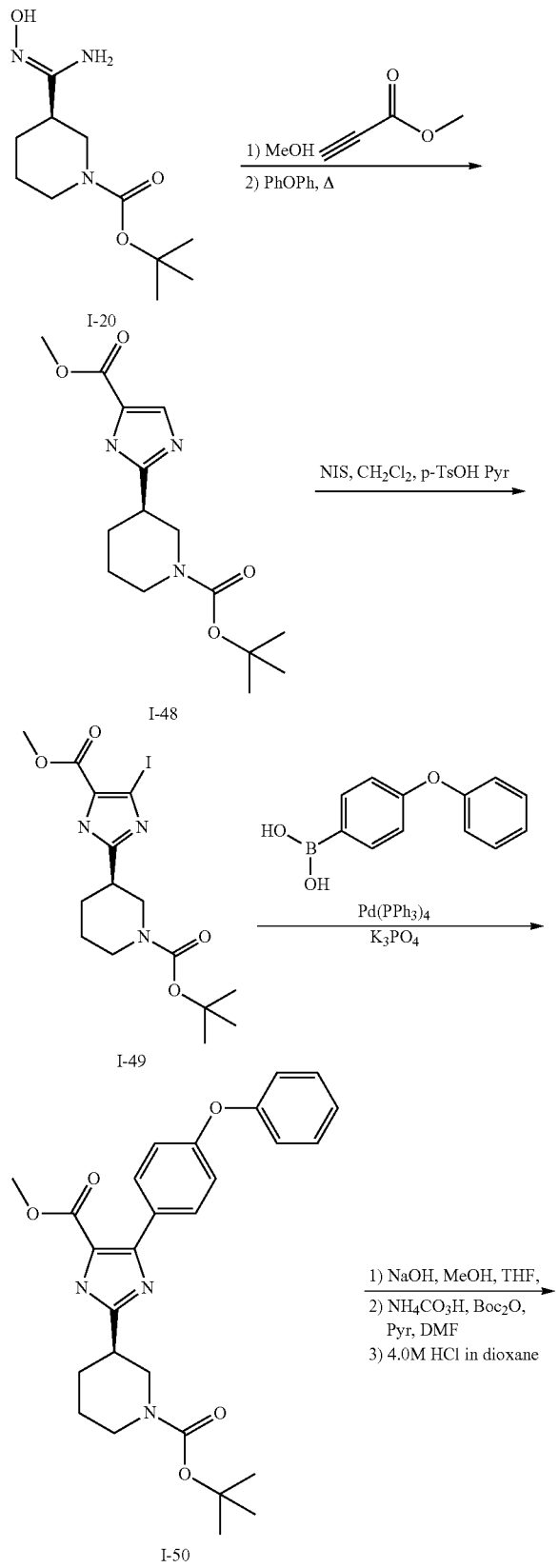

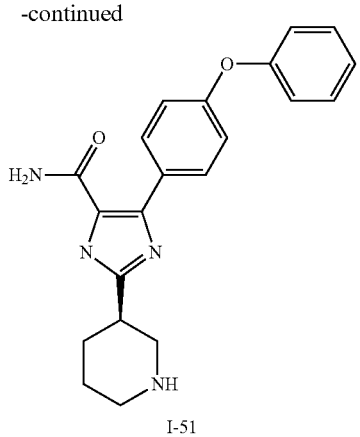

A solution of I-20 (500 mg, 2.1 mmol) and methyl propiolate (0.35 mL, 4.1 mmol) in MeOH (10 mL) is heated at 65° C. for 4 h. The mixture is concentrated in vacuo then dissolved in diphenyl ether (2 mL) and heated at 200° C. for 1 h. The mixture is cooled to ambient temperature then purified by flash chromatography (SiO$_2$, Hep to EtOAc) to give I-48 (317 mg, 50%) m/z 310.2 [M+H].

To a solution of I-48 (317 mg, 1.0 mmol) and p-TsOH Pyr (461 mg, 2.1 mmol) in CH$_2$Cl$_2$ (5 mL) is added NIS (461 mg, 2.1 mmol). The mixture is stirred in the dark at ambient temperature for 24 h. The mixture is treated with saturated aqueous Na$_2$SO$_3$ then filtered through a phase separator. The organics are collected and concentrated in vacuo to afford a residue that is purified by flash chromatography (SiO$_2$, Hep to 80% EtOAc in Hep) to afford I-49 (339 mg, 76%) m/z 436.0 [M+H].

A mixture of I-49 (339 mg, 0.78 mmol), 4-phenoxylphenylboronic acid (333 mg, 1.56 mmol), and tetrakis(triphenylphosphine)palladium(0) (90 mg, 0.078 mmol), and K$_3$PO$_4$ (827 mg, 3.89 mmol) in dioxane (4 mL) is heated at 100° C. in the microwave for 45 min. The mixture is cooled and concentrated in vacuo to afford a residue that is purified by flash chromatography (SiO$_2$, Hep to 80% EtOAc in Hep) to afford I-50 (302 mg, 81%) m/z 478.2 [M+H].

A solution of I-50 (372 mg, 0.78 mmol) in MeOH (1.5 mL), THF (1 mL), and 3M aqueous NaOH (3 mL) is heated at ambient temperature for 20 h then acidified to pH=5 with concentrated aqueous HCl. The volatiles are removed in vacuo and residue triturated with a mixture of CH$_2$Cl$_2$ and MTBE. The solid is filtered, collected, and dried. The solid is dissolved in DMF (2 mL) and treated with pyridine (0.1 mL, 1.2 mmol), Boc anhydride (69 mg, 0.87 mmol), followed by ammonium bicarbonate (96 mg, 1.2 mmol). The mixture is stirred for 16 h then partitioned between water and CH$_2$Cl$_2$. The mixture is filtered through a phase Separator® and organics are concentrated in vacuo to afford a residue that is purified by flash chromatography (SiO$_2$, CH$_2$Cl$_2$ to 5% MeOH in CH$_2$Cl$_2$). The purified material is dissolved in CH$_2$Cl$_2$ (2 mL) and treated with 4.0M HCl in dioxane (4 mL). The mixture is stirred for 2 h then volatiles are removed in vacuo to afford a residue that is purified by trituration with MTBE:EtOAc to give I-51 (75 mg, 22%) m/z 393.1 [M+H].

The following intermediate is prepared in similar fashion:

| Structure | Intermediate | m/z |
|---|---|---|
| 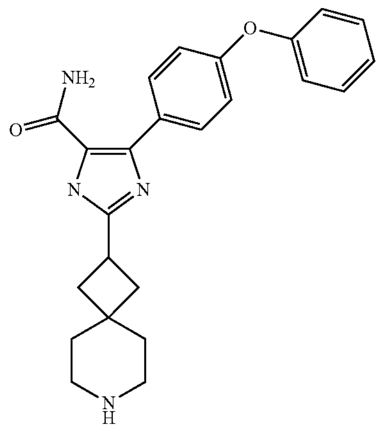 [SMILES: NC(=O)c1[nH]c(C2CC3(CCNCC3)C2)nc1-c1ccc(Oc2ccccc2)cc1] | I-52 | 403.2 [M + H] |

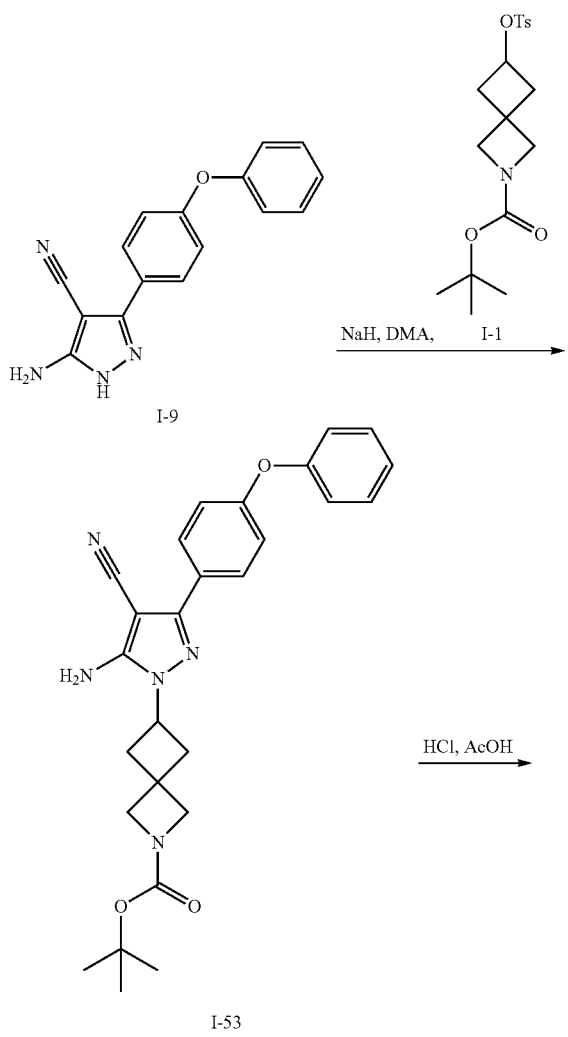

Method 15

Synthesis of Intermediate I-54

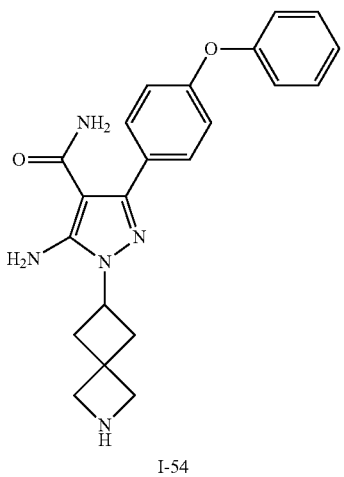

I-54

To a solution of I-9 (1.50 g, 5.4 mmol) in DMF (20 mL) is added sodium hydride (60% dispersion in mineral oil, 0.26 g, 6.5 mmol). The mixture is stirred for 5 min then I-1 (2.39 g, 6.5 mmol) is added. The mixture is heated at 70° C. for 18 h then cooled to ambient temperature. The mixture is partitioned between EtOAc and water then organics are collected, dried over $Na_2SO_4$, filtered, and concentrated in vacuo. The residue is purified by flash chromatography ($SiO_2$, Hep to 70% EtOAc in Hep) to afford I-53 (1.2 g, 47%) m/z 472.2 [M+H].

A solution of I-53 (1.00 g, 2.2 mmol) in AcOH (5 mL) and Concentrated aqueous HCl (1 mL) is heated at 90° C. for 10 h. The mixture is cooled to ambient temperature then poured into ice. The mixture is basified to pH 9-10 by addition of ammonium hydroxide then extracted with EtOAc, washed with brine, dried over $Na_2SO_4$, filtered, and concentrated in vacuo. The residue is purified by RHPLC to afford I-54 (0.39 g, 48%) m/z 390.1 [M+H].

The following intermediates are prepared in similar fashion:

| Structure | Intermediate | m/z |
|---|---|---|
| 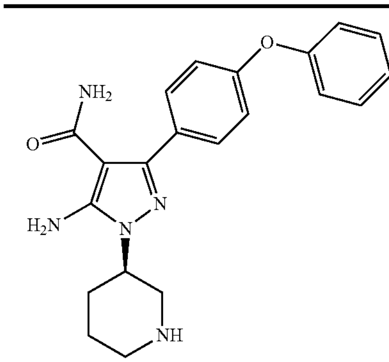 | I-54 | 378.1 [M + H] |

179
-continued
| Structure | Intermediate | m/z |
|---|---|---|
| 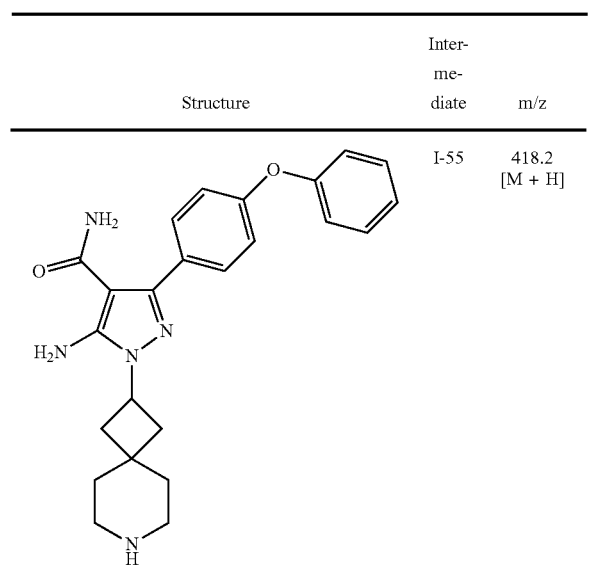 | I-55 | 418.2 [M + H] |
| 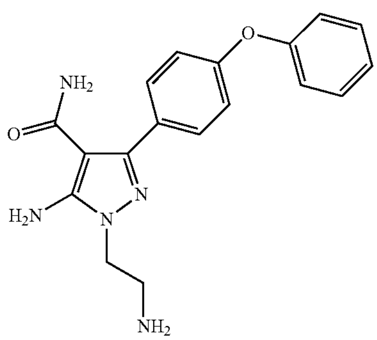 [SMILES: NCCn1nc(-c2ccc(Oc3ccccc3)cc2)c(C(N)=O)c1N] | I-56 | |
| 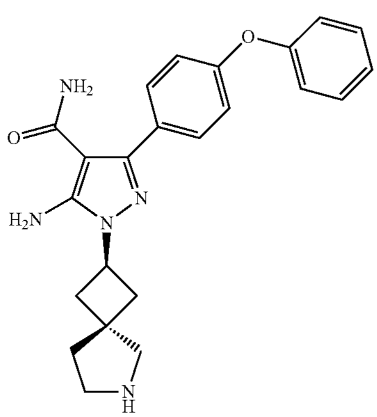 [SMILES: NC(=O)c1c(-c2ccc(Oc3ccccc3)cc2)nn([C@H]2C[C@@]3(CCNC3)C2)c1N] | I-57 | 404.1 [M + H] |
180
-continued
| Structure | Intermediate | m/z |
|---|---|---|
| 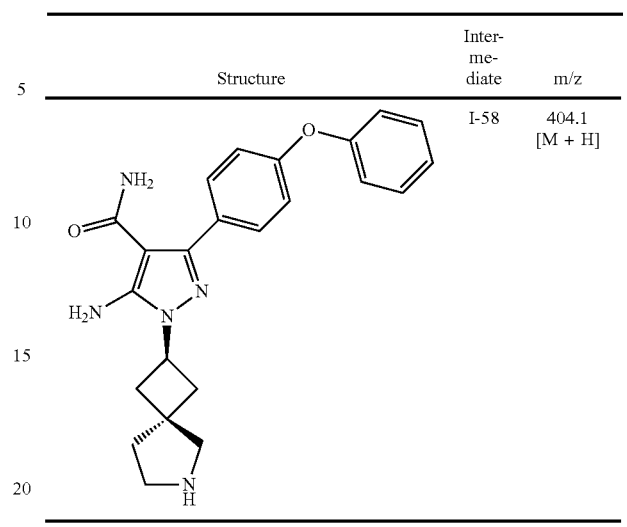 | I-58 | 404.1 [M + H] |
Method 16
Synthesis of Example 9
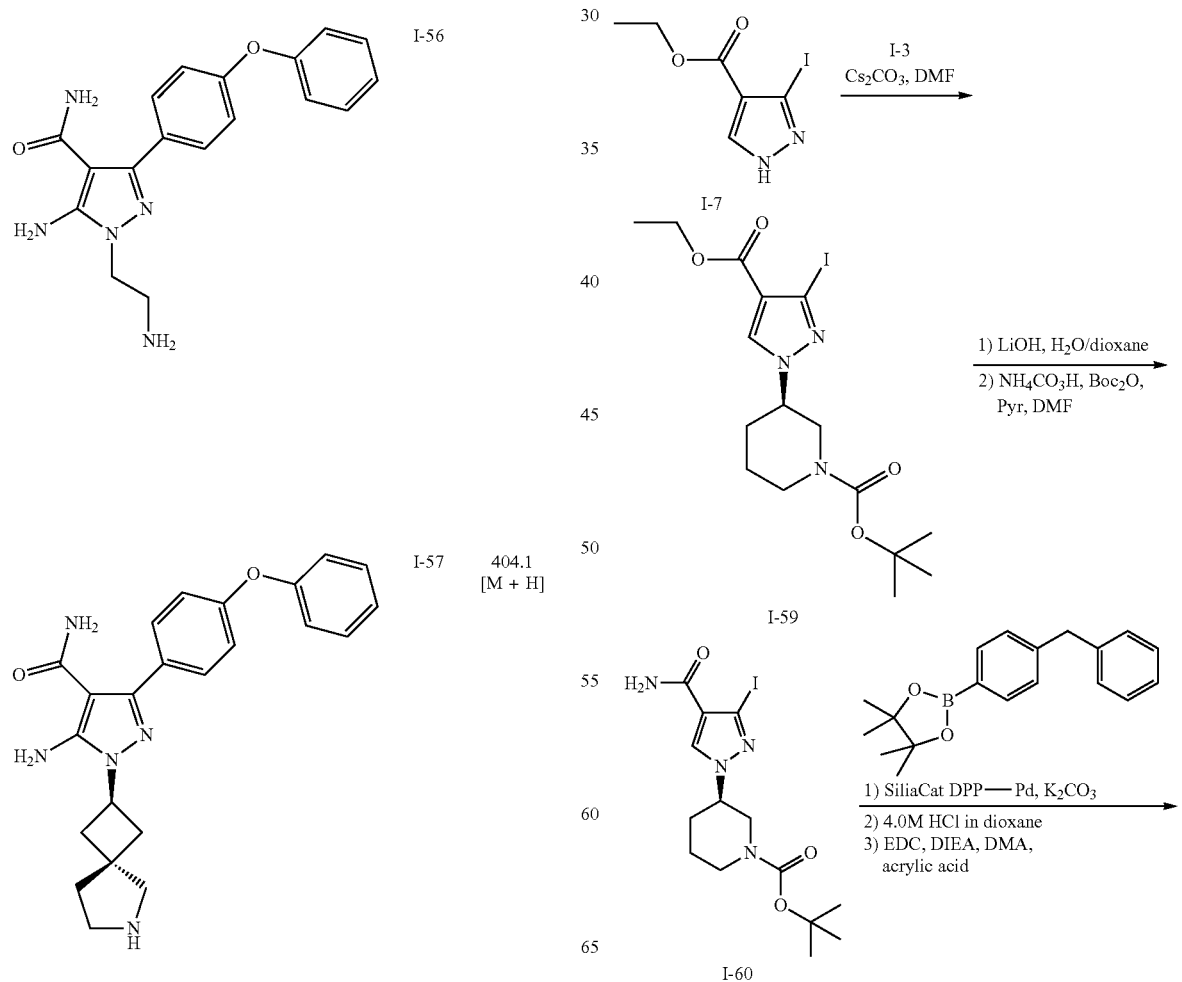

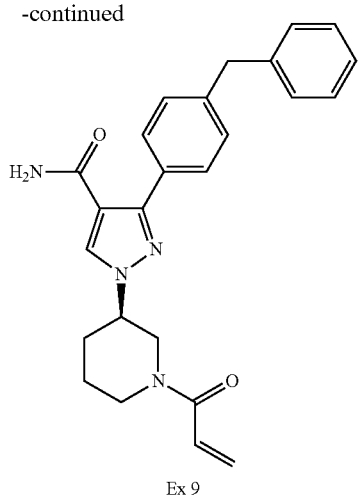

Ex 9

To a solution of I-7 (2.00 g, 7.5 mmol) in DMF (20 mL) is added Cs₂CO₃ (4.9 g, 15 mmol) and I-3 (4.0 g, 11 mmol). The reaction mixture is heated at 60° C. for 24 h then cooled to ambient temperature. The mixture is partitioned between EtOAc and water. The organics are collected, washed with water, dried over MgSO₄, filtered, and concentrated in vacuo. The crude is purified by flash chromatography (SiO₂, Hep to 30% EtOAc in Hep) to afford I-59 (2.10 g, 62%) m/z 445.0 [M+H].

To a solution of I-59 (7.00 g, 15.6 mmol) in 1:1 dioxane: water (50 mL) is added LiOH (3.00 g, 125 mmol). The reaction mixture was heated at reflux for 2 h then volatiles are removed in vacuo. The residue is acidified with aqueous 2 N HCl to pH=4 then diluted with EtOAc, washed with brine, dried over Na₂SO₄, filtered, and concentrated in vacuo. The residue is dissolved in DMF (30 mL) and treated with Boc anhydride (2.22 g, 28 mmol) followed by ammonium bicarbonate (2.21 g, 28 mmol) and pyridine (2.2 mL, 28 mmol). The mixture is stirred for 16 h then volatiles are removed in vacuo. The residue is partitioned between EtOAc and saturated aqueous NH₄Cl then organics are collected, washed with brine, dried over Na₂SO₄, filtered, and concentrated in vacuo. The crude is purified by flash chromatography (SiO₂, 20-80% EtOAc in Hep, then 20% MeOH in CH₂Cl₂) to afford I-60 (3.8 g, 61%) m/z 421.0 [M+H]

To a solution of 4-benzylphenylboronic acid pinacol ester (47 mg, 0.16 mmol) in DME (1 mL) is added a solution of I-19 (45 mg, 0.11 mmol) in DME (1 mL). To this solution is added aqueous 1 M K₂CO₃ (1 mL) and SiliaCat DPP-Pd (50 mg, 0.01 mmol). The mixture is heated at 100° C. for 16 h then concentrated in vacuo. The crude was purified by RHPLC to afford a residue that is dissolved in DCE and treated with 4.0M HCl in dioxane (0.5 mL). The mixture is stirred for 16 h then volatiles are removed in vacuo. To the residue is added a solution of acrylic acid (7.7 mg, 0.11 mmol), EDC (23 mg, 0.12 mmol), and DIEA (35 uL, 0.20 mmol) in DMA (0.8 mL). The reaction mixture is stirred for 4 h then volatiles were removed in vacuo to afford a residue that was purified by RHPLC to afford example 9 (12 mg, 26%).

The following compounds were prepared in a similar manner:

Examples 1-8, 10-27, 94-96

Method 17

Synthesis of Example 28

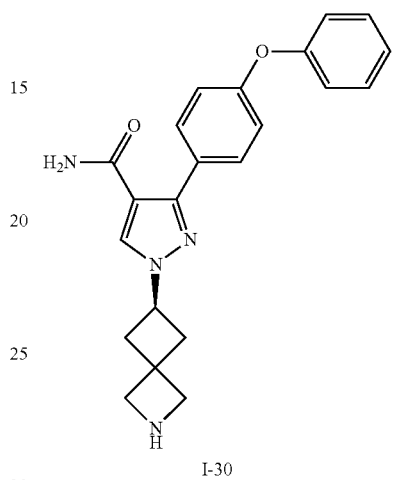

I-30 acrylic acid, TBTU, DIEA, DMF
⟶

Ex 28

To a solution of I-30 (75 mg, 0.20 mmol) in DMF (2 mL) is added DIEA (0.3 mL), TBTU (96 mg, 0.30 mmol), and acrylic acid (22 mg, 0.30 mmol). The mixture is stirred for 12 h at ambient temperature then treated with water. The mixture is extracted with EtOAc, dried over Na₂SO₄, filtered, and concentrated in vacuo. The crude is purified by flash chromatography (30 to 90% EtOAc in Hep) to give example 28 (36 mg, 42%).

The following compounds are prepared in similar fashion: Examples 29, 33, 39, 42, 45, 47, 55, 88

Method 18

Synthesis of Example 38

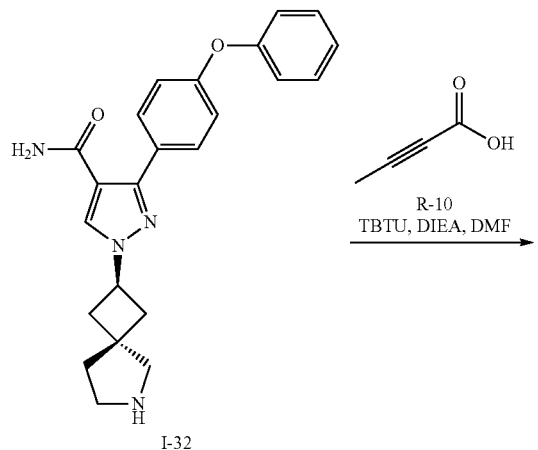

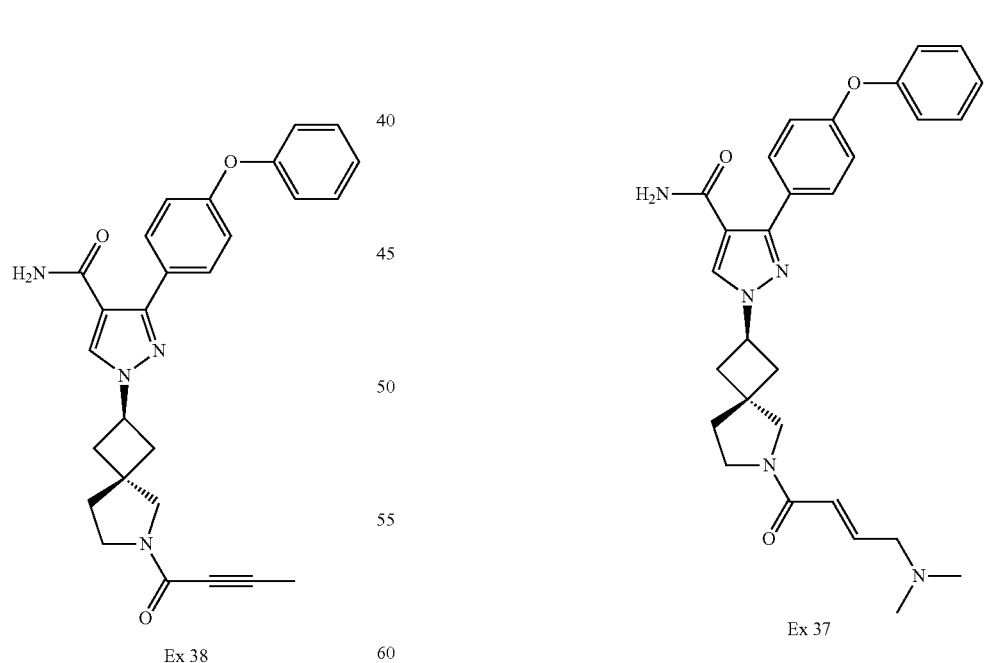

To a solution of I-32 (70 mg, 0.18 mmol) in DMF (3 mL) is added DIEA (1 mL), TBTU (116 mg, 0.36 mmol), and R-10 (17 mg, 0.20 mmol). The mixture is stirred for 12 h at ambient temperature then treated with water. The mixture is extracted with EtOAc, dried over Na$_2$SO$_4$, filtered, and concentrated in vacuo. The crude is purified by RHPLC to give example 38 (38 mg, 46%).

The following compounds are prepared in similar fashion: Examples 31, 32, 43, 48, 49, 56

Method 19

Synthesis of Example 37

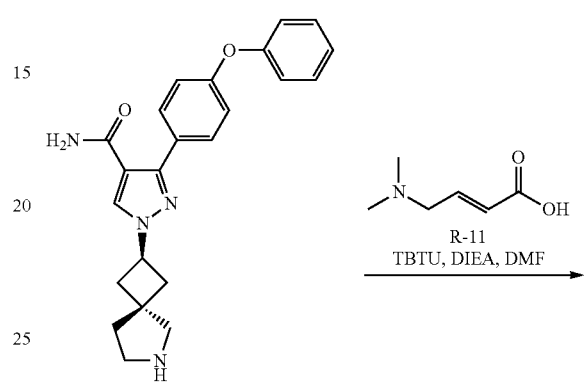

To a solution of I-32 (25 mg, 0.064 mmol) in DMF (2 mL) is added DIEA (0.4 mL), TBTU (32 mg, 0.080 mmol), and R-11 (10 mg, 0.080 mmol). The mixture is stirred for 12 h at ambient temperature then treated with water. The mixture is extracted with EtOAc, dried over Na$_2$SO$_4$, filtered, and concentrated in vacuo. The crude is purified by flash chromatography (SiO$_2$, 30 to 70% EtOAc in Hep) to give example 37 (5 mg, 16%).

The following compounds are prepared in similar fashion: Examples 30, 36

Method 20

Synthesis of Example 40

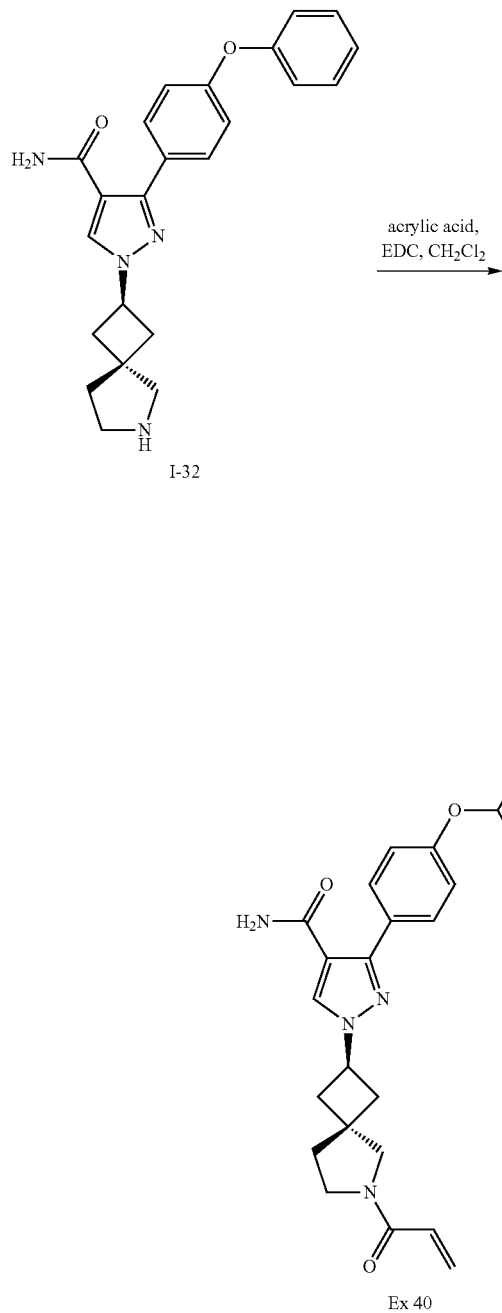

Ex 40

To a solution of I-32 (100 mg, 0.26 mmol) in CH$_2$Cl$_2$ (2 mL) is added EDC (60 mg, 0.31 mmol) followed by acrylic acid (22 mg, 0.31 mmol). The mixture is stirred at ambient temperature for 1 h then directly purified by flash chromatography (SiO$_2$, CH$_2$Cl$_2$ to 5% MeOH in CH$_2$Cl$_2$) to give example 40 (15 mg, 13%).

The following compounds were made in similar fashion: Examples 86, 89 (R-10 used instead of acrylic acid)

Method 21

Synthesis of Example 60

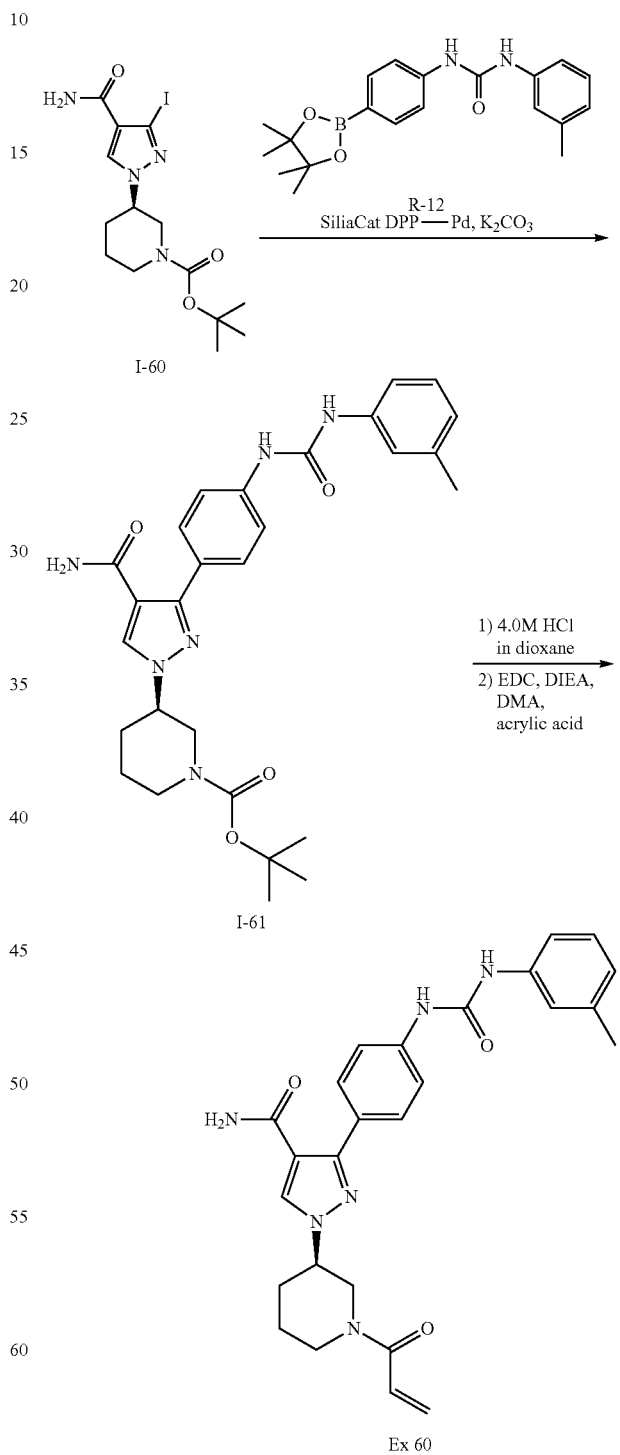

Ex 60

To a solution of I-60 (43 mg, 0.10 mmol) in DME (2 mL) is added R-12 (65 mg, 0.18 mmol), SiliaCat DPP-Pd (50 mg, 0.01 mmol), and potassium carbonate (500 mg). The mixture is heated at 140° C. in a microwave for 2 h then concentrated in vacuo. The crude is purified by flash chromatography (SiO₂, 0 to 4% MeOH in CH₂Cl₂) to give I-61 (38 mg, 72%) m/z 519.2 [M+H].

I-61 (38 mg, 0.073 mmol) is dissolved in CH₂Cl₂ (2 mL) and treated with 4.0M HCl in dioxane (3 mL). The mixture is stirred for 2 h at ambient temperature then volatiles are removed in vacuo. The residue is dissolved in CH₂Cl₂ (2 mL) and treated with acrylic acid (5 mg, 0.073 mmol) and EDC (14 mg, 0.073 mmol). The mixture is stirred for 1 h at ambient temperature then partitioned between water and CH₂Cl₂. The mixture is filtered through a phase Separator® and organics are collected and concentrated in vacuo. The crude is purified by flash chromatography (SiO₂, CH₂Cl₂ to 8% MeOH in CH₂Cl₂) to give example 60 (13 mg, 57%).

The following compound was made in similar fashion:
Example 61

Method 22

Synthesis of Example 72

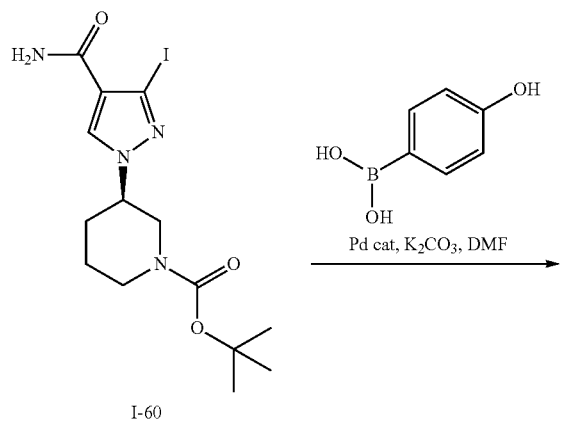

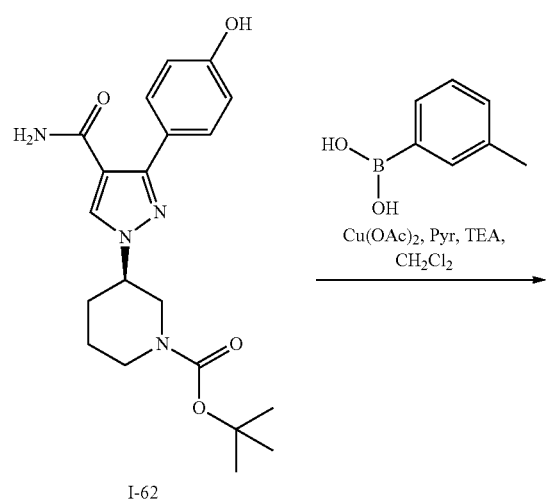

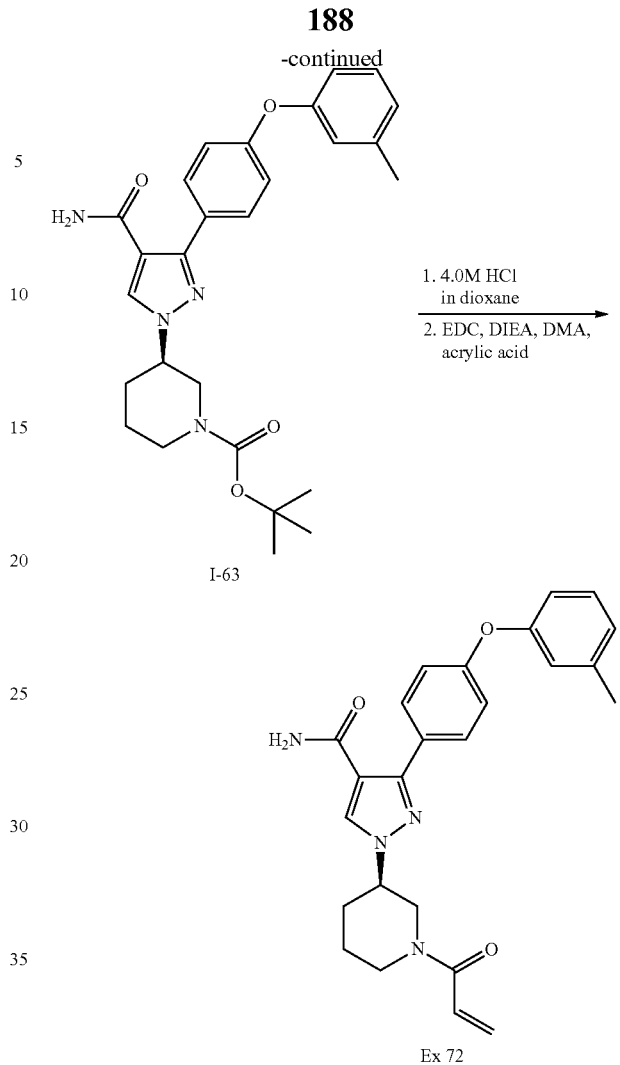

A flask is charged with I-60 (4.0 g, 9.5 mmol), 4-hydroxyphenylboronic acid (1.9 g, 14 mmol), bis (di-tert-butyl(4-dimethylaminophenyl)phosphine)dichloropalladium(II) (0.67 g, 0.95 mmol), potassium carbonate (2.5 g, 18 mmol) and treated with DMF (40 mL) and water (10 mL). The mixture is heated in the microwave at 140° C. for 90 min. The mixture is cooled to ambient temperature then treated with saturated aqueous NH₄Cl, extracted with EtOAc, dried over Na₂SO₄, filtered, and concentrated in vacuo. The crude is purified by flash chromatography (SiO₂, 20 to 50% EtOAc in Hep) to give I-62 (2.0 g, 54%) m/z [M+H].

To a solution of I-62 (90 mg, 0.23 mmol) in CH₂Cl₂ (7 mL) is added 3-tolylboronic acid (95 mg, 0.70 mmol), Cu(OAc)₂ (300 mg), pyridine (1 mL), TEA (1 mL), and molecular sieves (4 Å). The mixture is stirred at ambient temperature open to air for 12 h. The mixture was filtered through a silica gel pad and volatiles from the filtrate are removed in vacuo. The crude is purified by RHPLC to afford I-63 (61 mg, 55%) m/z 477.1 [M+H].

To a solution of I-63 (55 mg, 0.115 mmol) in CH₂Cl₂ (3 mL) is added TFA (1 mL). The mixture is stirred at ambient temperature for 2 h then treated with saturated aqueous Na₂CO₃. The layers are separated and volatiles from the organics are removed in vacuo to afford a residue. The residue is dissolved in DMF (4 mL) and treated with acrylic acid (0.6 mL) and EDC (38 mg, 0.25 mmol). The mixture is stirred at ambient temperature 12 h then directly purified by RHPLC to give example 72 (17 mg, 34%).

The following compounds are prepared in similar fashion: Examples 62-71, 73-76

Method 23

Synthesis of Example 90

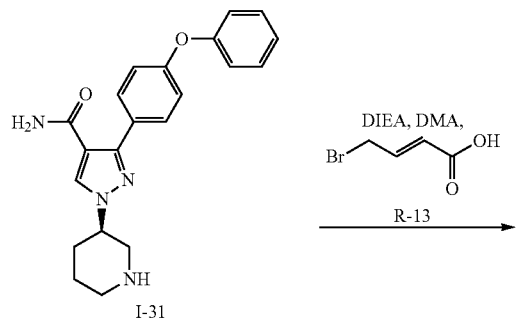

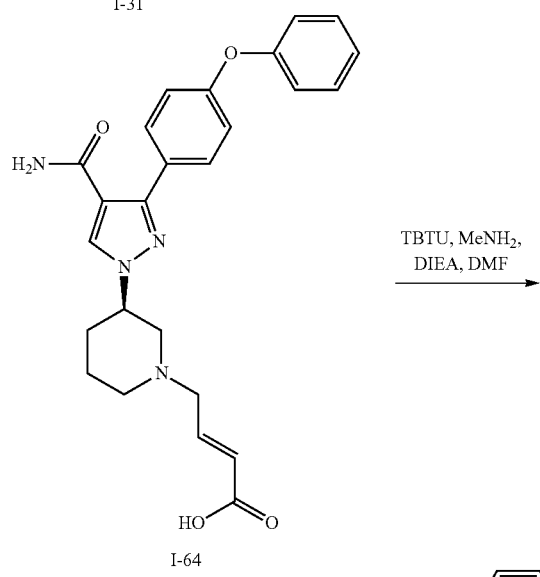

To a solution of I-31 (0.20 g, 0.55 mmol) in DMA (3 mL) is added DIEA (0.15 mL, 0.86 mmol) and R-13 (0.12 g, 0.71 mmol). The mixture is heated at 50° C. for 18 h then cooled to ambient temperature. The mixture is partitioned between water and EtOAc. The organics are collected, dried over Na$_2$SO$_4$, filtered, and concentrated in vacuo. The crude is purified by RHPLC to afford I-64 (0.15 g, 62%) m/z 447.1 [M+H].

To a solution of I-64 (70 mg, 0.16 mmol) in DMF (2 mL) is added TBTU (60 mg, 0.19 mmol) and DIEA (0.06 mL, 0.19 mmol). The mixture is stirred for 5 min then treated with a 2.0M solution of methylamine in THF (0.24 mL, 0.47 mmol). The mixture is stirred at ambient temperature for 16 h then treated with saturated aqueous ammonium chloride. The mixture is extracted with EtOAc, dried over Na$_2$SO$_4$, filtered, and concentrated in vacuo. The crude is purified by RHPLC to afford example 90 (7 mg, 10%).

Method 24

Synthesis of Example 93

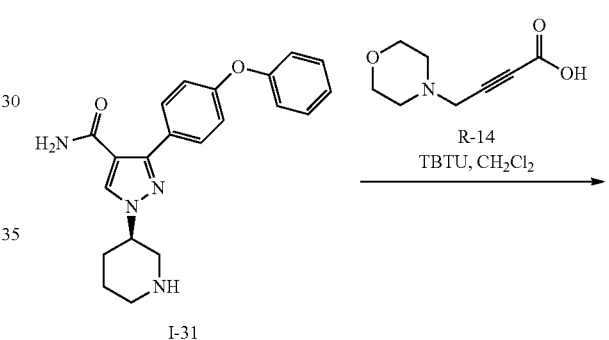

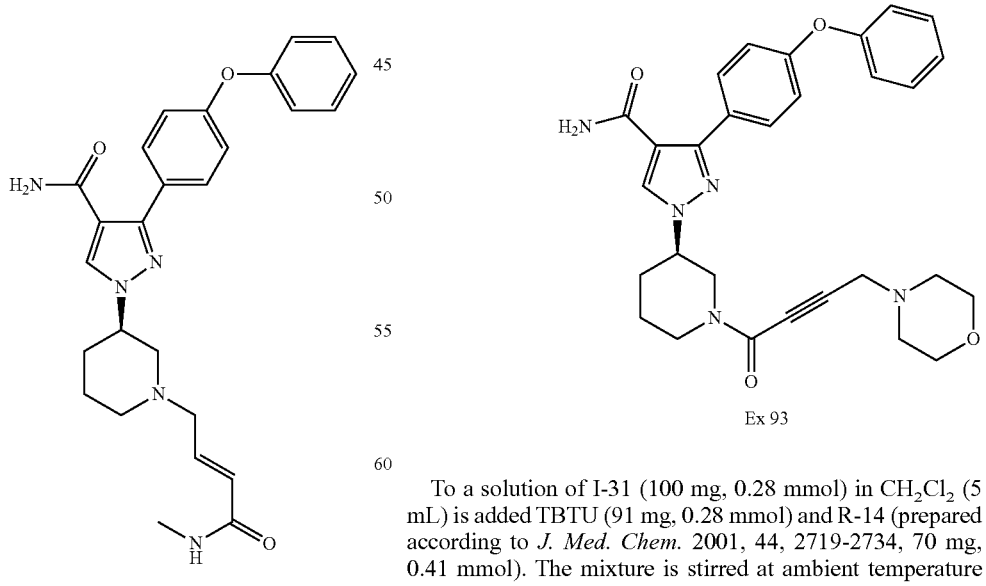

To a solution of I-31 (100 mg, 0.28 mmol) in CH$_2$Cl$_2$ (5 mL) is added TBTU (91 mg, 0.28 mmol) and R-14 (prepared according to *J. Med. Chem.* 2001, 44, 2719-2734, 70 mg, 0.41 mmol). The mixture is stirred at ambient temperature over night then filtered and purified by flash chromatography (SiO$_2$, CH$_2$Cl$_2$ to 10% MeOH with 1% ammonium hydroxide) to give example 93 (58 mg, 41%).

Method 25

Synthesis of Example 58

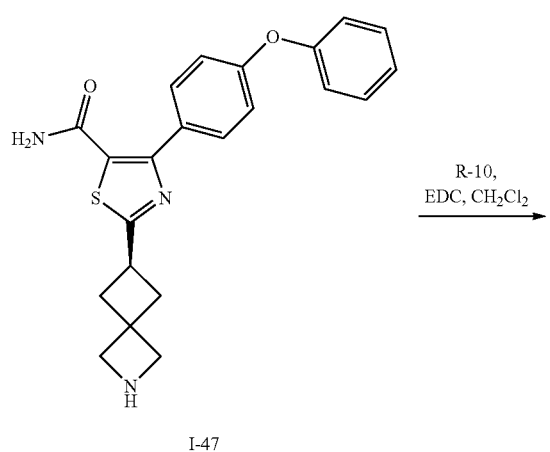

I-47

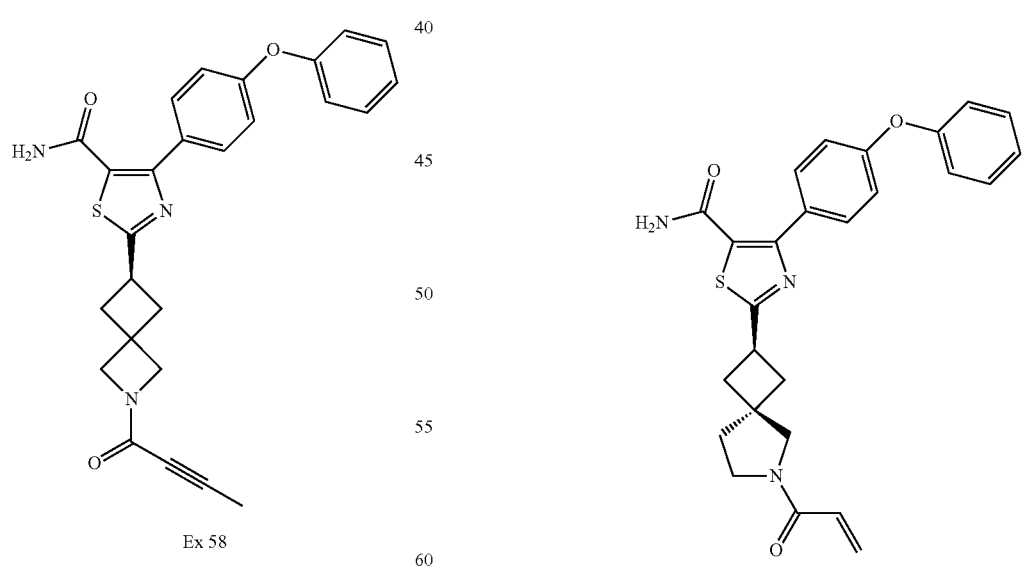

Ex 58

To a solution of I-47 (29 mg, 0.074 mmol) in CH$_2$Cl$_2$ (2 mL) is added EDC (92 mg, 0.38 mmol) and R-10 (20 mg, 0.24 mmol). The mixture is stirred at ambient temperature for 1 h then partitioned between water and CH$_2$Cl$_2$. The mixture is filtered through a phase Separator® and organics are collected and concentrated in vacuo. The crude is purified by flash chromatography (SiO$_2$, 20 to 100% EtOAc in Hep) to give example 58 (23 mg, 68%).

The following compounds are made in similar fashion: Examples 78, 85, 52, 53

Method 26

Synthesis of Example 79

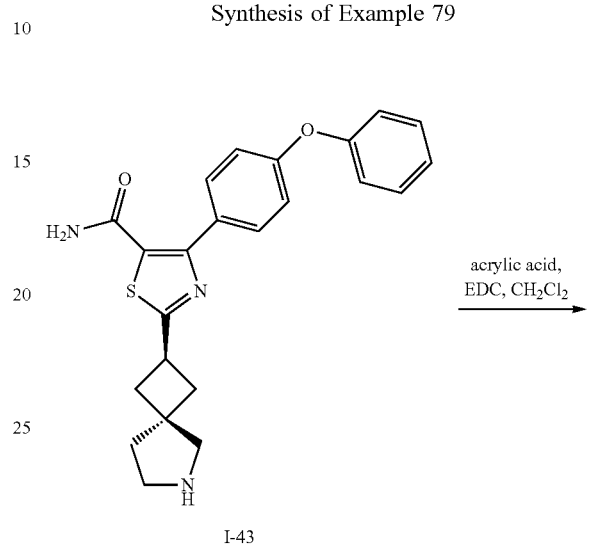

I-43

Ex 79

To a solution of I-43 (65 mg, 0.16 mmol) in CH$_2$Cl$_2$ (2 mL) is added EDC (37 mg, 0.19 mmol) followed by acrylic acid (14 mg, 0.19 mmol). The mixture is stirred at ambient temperature for 1 h then directly purified by flash chromatography (SiO$_2$, CH$_2$Cl$_2$ to 5% MeOH in CH$_2$Cl$_2$) to give example 79 (14 mg, 19%).

The following compounds were made in similar fashion: Examples 34, 50, 51, 57, 84

Method 27

Synthesis of Example 77

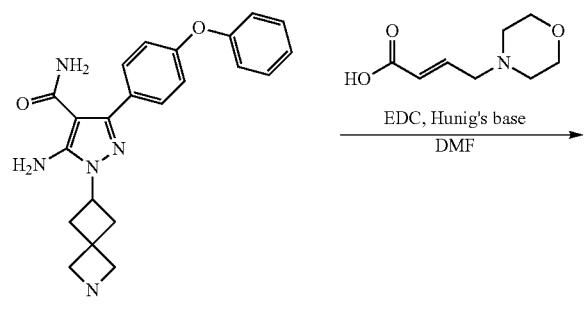

I-54

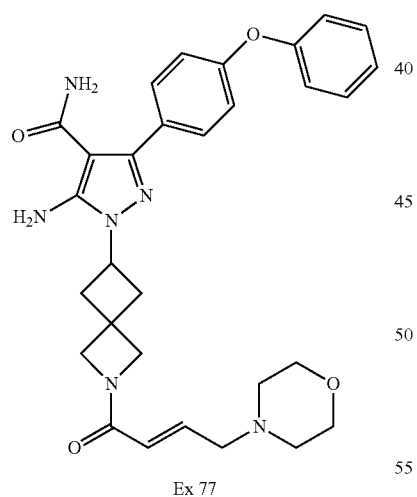

Ex 77

A solution of morpholine (35 mg, 0.4 mmol), (E)-4-bromo-but-2-enoic acid (79 mg, 0.48 mmol), and Hunig's base (0.21 mL, 1.2 mmol) in DMF (2 mL) is stirred for 18 h. To this mixture is added EDC (71 mg, 0.37 mmol). The mixture is stirred for 5 min then treated with I-54 (120 mg, 0.31 mmol) and stirred for 18 h. Saturated aqueous ammonium chloride is added (4 mL) and mixture is extracted with EtOAc, dried over sodium sulphate, concentrated, and then purified by preparative TLC (SiO$_2$, 30% MeOH in EtOAc) to provide example 77 (64 mg, 38%).

The following compounds are made in similar fashion: Examples 98-100

Method 28

Synthesis of Example 80

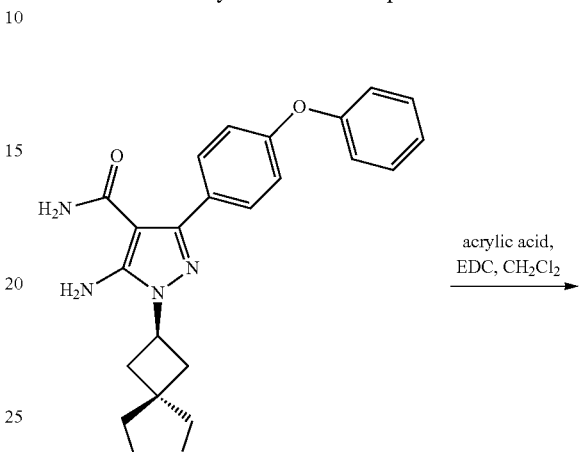

I-57

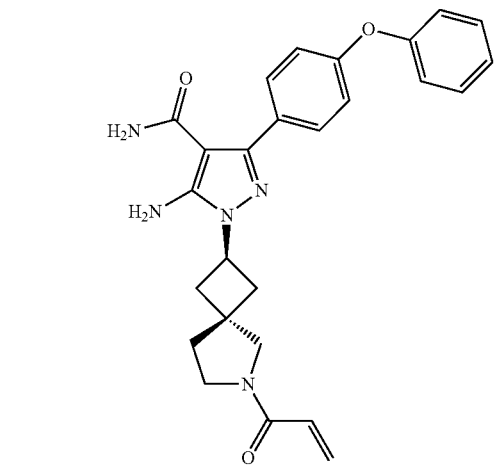

Ex 80

To a solution of I-57 (200 mg, 0.51 mmol) in DMF (2 mL) is treated with DIEA (150 mg, 1.1 mmol), EDC (130 mg, 0.67 mmol), followed by acrylic acid (0.05 mL, 0.67 mmol). The solution is stirred for 16 h then treated with saturated aqueous ammonium chloride. The mixture is extracted with EtOAc, dried over Na$_2$SO$_4$, filtered, and concentrated in vacuo. The crude is purified by flash chromatography

195

(SiO$_2$, EtOAc to 10% MeOH in EtOAc) to afford example 80 (52 mg, 23%).

The following compounds are prepared in similar fashion: Examples 35, 44, 54, 81, 82

Method 29

Synthesis of Example 41

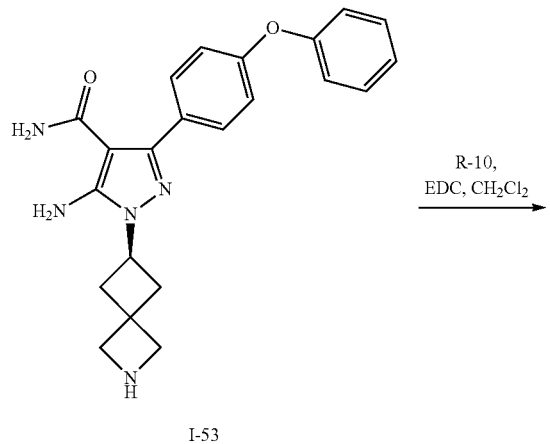

I-53

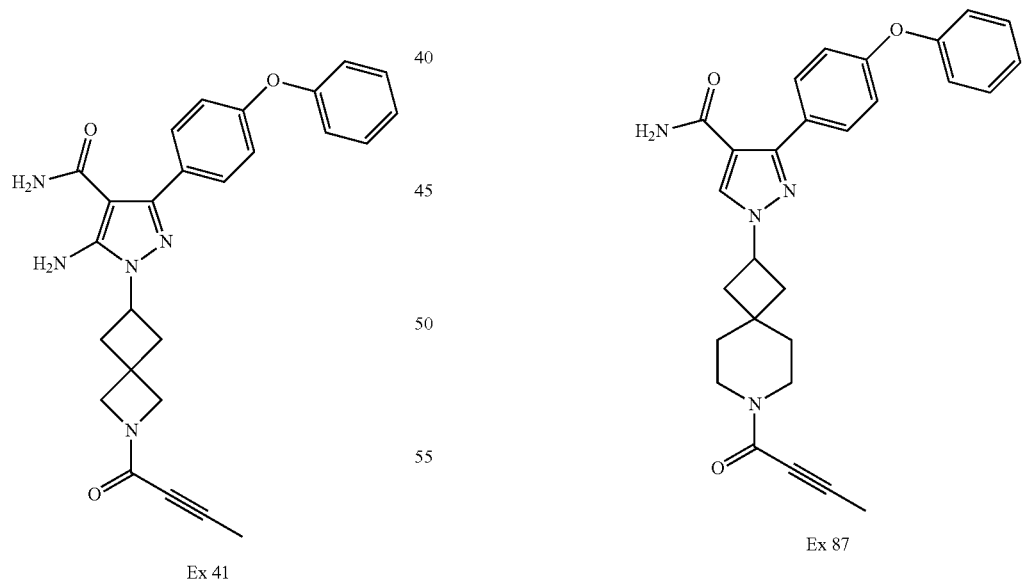

Ex 41

To a solution of I-53 (100 mg, 0.26 mmol) in DMF (2 mL) is added EDC (54 mg, 0.28 mmol) and R-10 (23 mg, 0.28 mmol). The mixture is stirred at ambient temperature for 16 h then partitioned between saturated aqueous ammonium chloride and EtOAc. The organics are collected, dried over Na$_2$SO$_4$, filtered, and concentrated. The crude is purified by

196 flash chromatography (SiO$_2$, EtOAc to 10% MeOH in EtOAc) to give example 41 (24 mg, 21%).

The following compounds are prepared in similar fashion: Examples 83, 91, 92

Method 30

Synthesis of Example 87

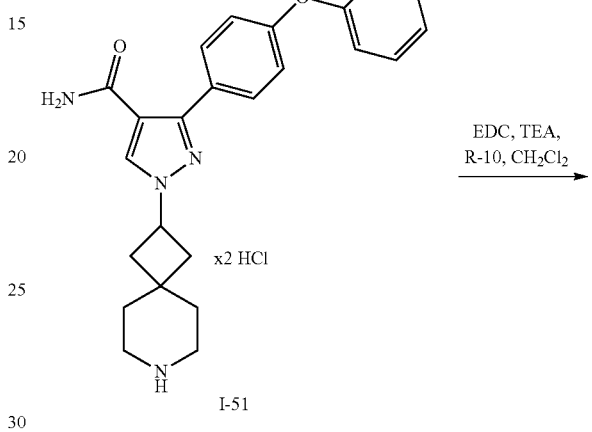

I-51

Ex 87

To a solution of the bis HCl salt of I-51 (55 mg, 0.12 mmol) in CH$_2$Cl$_2$ (1.7 mL) is added TEA (29 mg, 0.29 mmol), EDC (34 mg, 0.17 mmol), and R-10 (15 mg, 0.17 mmol). The mixture is stirred at ambient temperature for 2 h then partitioned between water and CH$_2$Cl$_2$ then filtered through a phase Separator®. The organics are collected and concentrated in vacuo to afford a residue that is purified by flash chromatography (SiO$_2$, CH$_2$Cl$_2$ to 45% MeOH in CH$_2$Cl$_2$) to afford example 87 (25 mg, 46%).

The following compounds were prepared in similar fashion:

Examples 59, 46 (acrylic acid used instead of R-10)

Method 31

Synthesis of Example 97

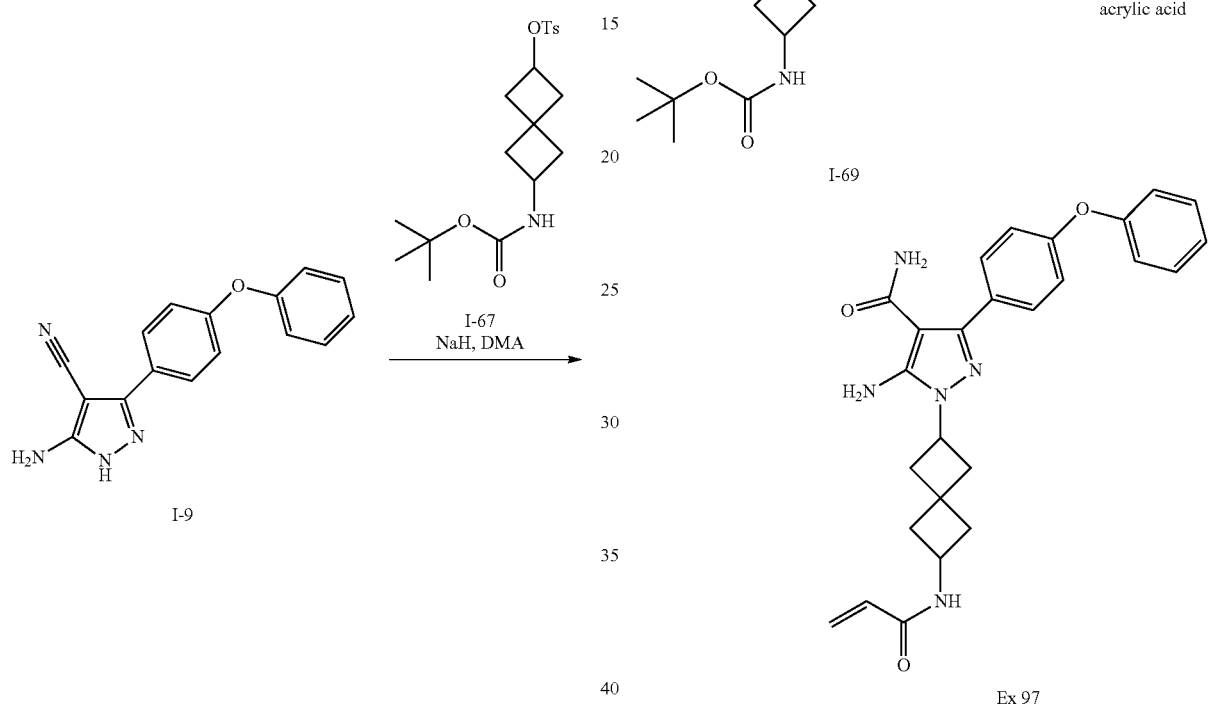

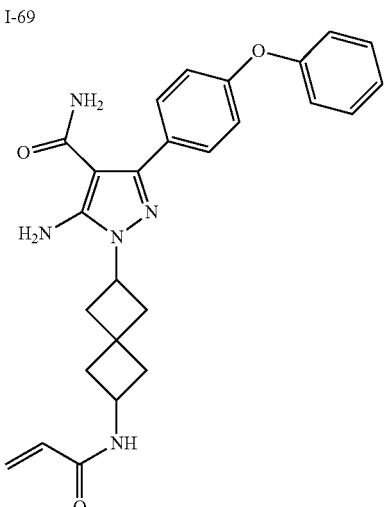

To a suspension of NaH (60% dispersion in mineral oil, 160 mg, 4.0 mmol) in DMF (5 mL) is added I-9 (0.93 g, 3.35 mmol). After 5 min of stirring, a solution of I-67 (1.28 g, 3.35 mmol) in DMF (5 mL) is added. The mixture is heated at 70° C. overnight then cooled to ambient temperature and partitioned between EtOAc and water. The organics are collected and washed with water and brine, dried, and concentrated in vacuo. The crude is purified by flash chromatography (SiO$_2$, 0-70% EtOAc in Heptane) to afford I-68 (0.59 g, 37%) m/z 486.7 [M+H].

I-68 (0.59 g, 1.22 mmol) is diluted with EtOH (1 mL) and water (0.5 mL) and Hydrido(dimethylphosphinous acid kP) [hydrogen bis(dimethylphosphinito-kP)]platinum (II) (0.07 g, 0.163 mmol) is added. The mixture is heated at 80° C. overnight then concentrated in vacuo. The residue is dissolved in CH$_2$Cl$_2$ then filtered and concentrated to afford I-69 (0.28 g, 45%) m/z 504.7 [M+H].

I-69 (50 mg, 0.1 mmol) is dissolved in CH$_2$Cl$_2$ (0.8 mL) and TFA (0.08 mL). The mixture is stirred for 3 h then partitioned between CH$_2$Cl$_2$ and aqueous saturated NaHCO$_3$. Organics are combined and concentrated to give a residue that is treated with a prestirred (15 min) solution of acrylic acid (10 μL, 0.13 mmol), EDC (3.5 mg, 0.18 mmol), and Hunig's base (70 μL, 0.38 mmol) in DMF (1.0 mL). The mixture is stirred overnight then diluted with aqueous saturated ammonium chloride and extracted with EtOAc. The organics are combined, washed with brine, dried over Na$_2$SO$_4$, filtered, and concentrated in vacuo. The crude is purified by flash chromatography (SiO$_2$) to afford example 97 (5 mg, 88%).

Method 32

Synthesis of Example 101

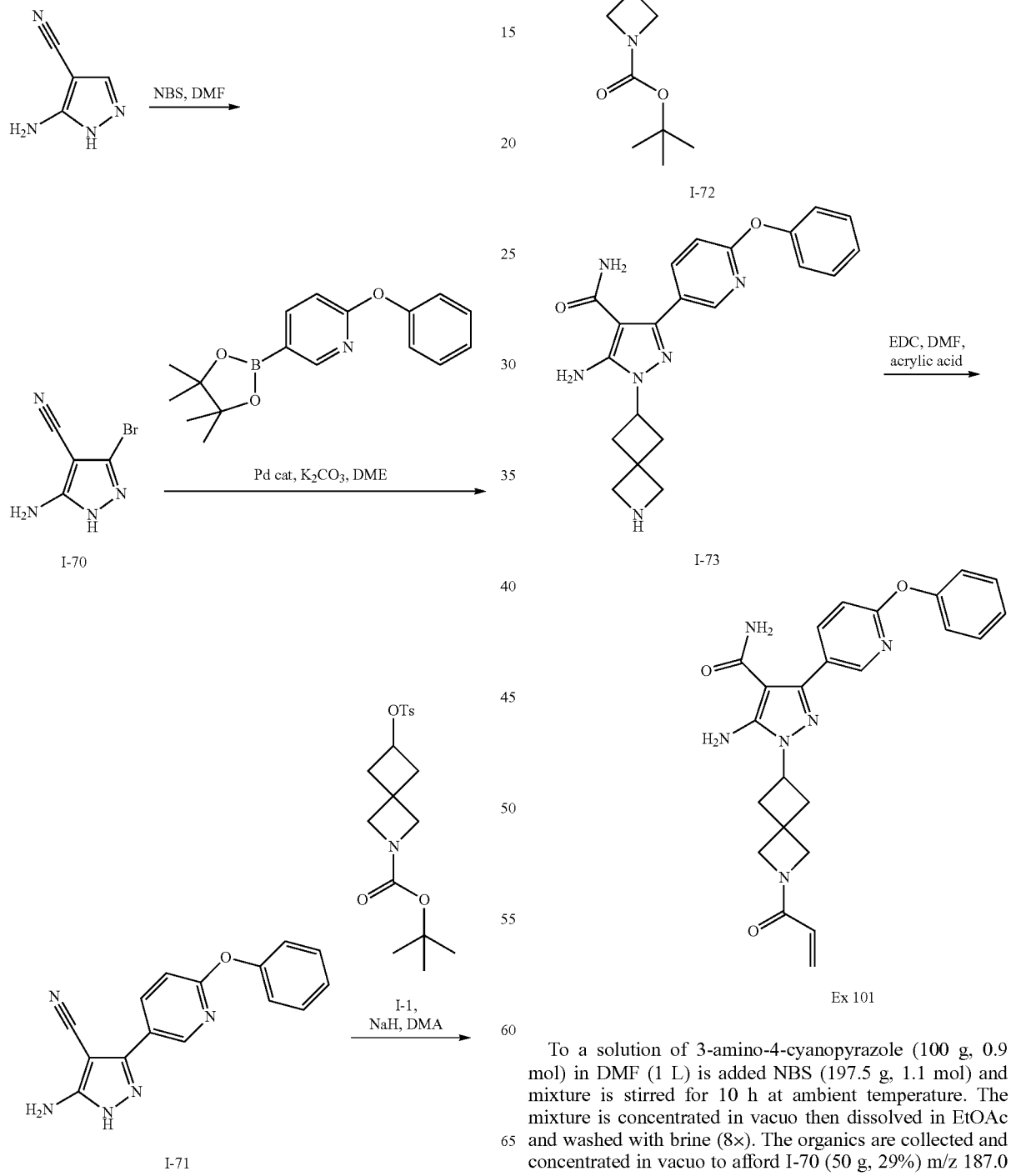

To a solution of 3-amino-4-cyanopyrazole (100 g, 0.9 mol) in DMF (1 L) is added NBS (197.5 g, 1.1 mol) and mixture is stirred for 10 h at ambient temperature. The mixture is concentrated in vacuo then dissolved in EtOAc and washed with brine (8×). The organics are collected and concentrated in vacuo to afford I-70 (50 g, 29%) m/z 187.0 [M+H].

A vial is charged with I-70 (1.0 g, 5.35 mmol), 2-phenoxy-5-(4,4,5,5-tetramethyl-[1,3,2]dioxaborolan-2-yl)-pyridine (2.07 g, 6.95 mmol), tetrakis(triphenylphosphine) palladium (0) (0.62 g, 0.535 mmol) and dissolved in aqueous potassium carbonate (10 mL, 2.0 M) and DME (6 mL). The mixture is heated at 130° C. for 3 h in a microwave. The mixture is filtered then diluted with water, extracted with EtOAc, dried over sodium sulphate, filtered, and concentrated in vacuo. The residue is purified by flash chromatography (SiO$_2$, 0-100% EtOAc in heptanes) to give I-71 (1.18 g, 80%) m/z 278.0 [M+H].

Sodium hydride (60% dispersion in mineral oil, 100 mg, 2.5 mmol) is added to a solution of I-71 (530 mg, 1.9 mmol) in DMF (7.5 mL). The mixture is stirred for 5 min then treated with I-1 (840 mg, 2.3 mmol) and heated at 70° C. for 18 h. The solution is cooled to ambient temperature then partitioned between EtOAc and water. Organics are collected, dried, filtered, and concentrated in vacuo to afford a residue that is purified by flash chromatography (SiO$_2$, 0-100% EtOAc in heptanes) to give I-72 (310 mg, 35%) m/z 473.2 [M+H].

I-72 (0.31 g, 0.66 mmol) is diluted with EtOH (5 mL) and water (0.5 mL) and Hydrido(dimethylphosphinous acid kP) [hydrogen bis(dimethylphosphinito-kP)]platinum (II) (28 mg, 0.066 mmol) is added. The mixture is heated at 80° C. overnight then concentrated in vacuo. The residue is dissolved in CH$_2$Cl$_2$ then filtered and concentrated to afford a residue that is dissolved in TFA (5 mL) and stirred for 3 h at ambient temperature then concentrated in vacuo. The residue is dissolved in MeOH and passed through an Agilent Stratospheres PL-HCO3 MP SPE cartridge and concentrated in vacuo to afford I-73 (0.25 g, 98%) m/z 391.2 [M+H].

I-73 (110 mg, 0.28 mmol) is treated with a prestirred (15 min) solution of acrylic acid (21 µL, 0.13 mmol) and EDC (65 mg, 0.34 mmol) in DMF (2.0 mL). The mixture is stirred overnight then diluted with aqueous saturated ammonium chloride and extracted with EtOAc. The organics are combined, washed with brine, dried over Na$_2$SO$_4$, filtered, and concentrated in vacuo. The crude is purified by flash chromatography (SiO$_2$, 10% MeOH in EtOAc) to afford example 101 (32 mg, 26%).

The following compounds are made in similar fashion: Examples 102-103, 110

Method 33

Synthesis of Example 122

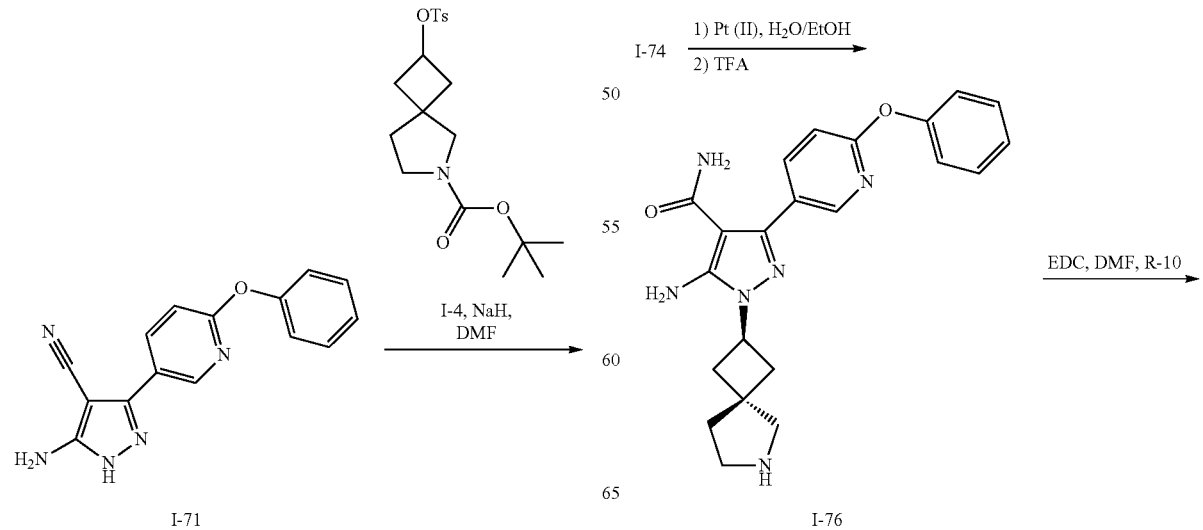

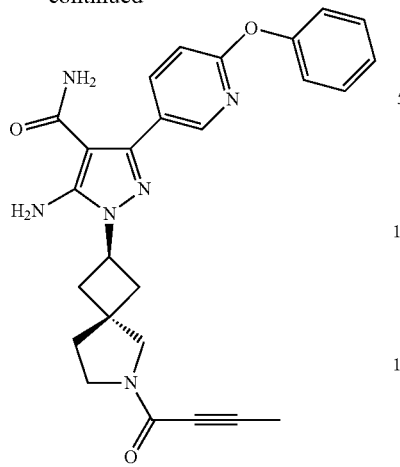

Ex 122

To a solution of I-71 (1.1 g, 3.97 mmol) in DMF (20 mL) is added NaH (60% dispersion in mineral oil, 190 mg, 4.76 mmol). The mixture is stirred for 5 min then treated with I-4 (1.82 g, 4.76 mmol) and heated at 70° C. for 18 h. The mixture is cooled then partitioned between EtOAc and water. Organics are collected, dried over $Na_2SO_4$, filtered, and concentrated in vacuo to give a residue that is purified by flash chromatography ($SiO_2$, 0-80% EtOAc in heptanes) to give I-74 (520 mg, 27%) m/z 487.3 [M+H] and I-75 (500 mg, 26%) m/z 487.3 [M+H].

I-74 (250 mg, 0.514 mmol) is diluted with EtOH (5 mL) and water (0.5 mL) and Hydrido(dimethylphosphinous acid kP) [hydrogen bis(dimethylphosphinito-kP)]platinum (II) (22 mg, 0.051 mmol) is added. The mixture is heated at 80° C. overnight then concentrated in vacuo. The residue is dissolved in $CH_2Cl_2$ then filtered and concentrated to afford a residue that is dissolved in TFA (5 mL) and stirred for 3 h at ambient temperature then concentrated in vacuo. The residue is dissolved in MeOH and passed through an Agilent Stratospheres PL-HCO3 MP SPE cartridge and concentrated in vacuo to afford I-76 (0.206 g, 98%) m/z 405.3 [M+H].

I-76 (254 mg, 0.63 mmol) is treated with a prestirred (15 min) solution of R-10 (69 mg, 0.82 mmol) and EDC (144 mg, 0.75 mmol) in DMF (2.0 mL). The mixture is stirred overnight then diluted with aqueous saturated ammonium chloride and extracted with EtOAc. The organics are combined, washed with brine, dried over $Na_2SO_4$, filtered, and concentrated in vacuo. The crude is purified by flash chromatography ($SiO_2$, 10% MeOH in EtOAc) to afford example 122 (48 mg, 16%).

The following compounds are made in similar fashion: Examples 114, 117-120, 123, 150-152

Method 34

Synthesis of Example 104

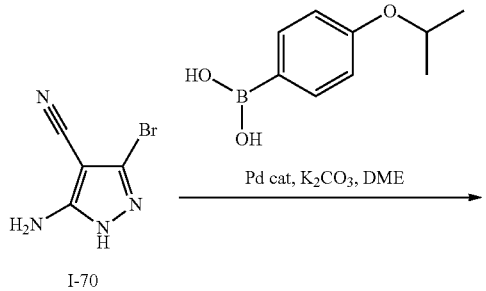

I-70

Pd cat, $K_2CO_3$, DME

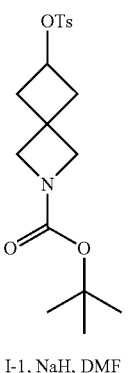

I-1, NaH, DMF

I-77

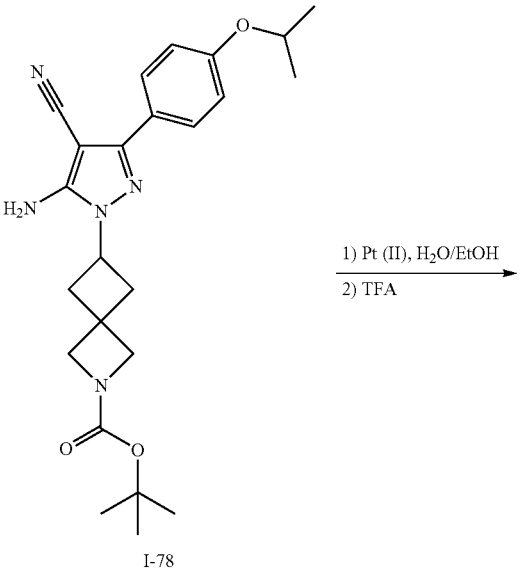

I-78

1) Pt (II), $H_2O$/EtOH
2) TFA

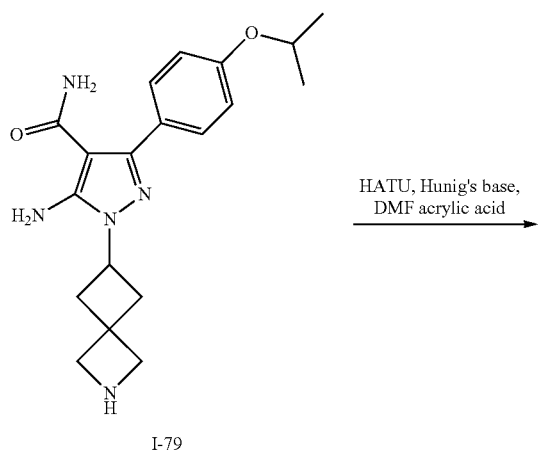

I-79

HATU, Hunig's base, DMF acrylic acid

-continued

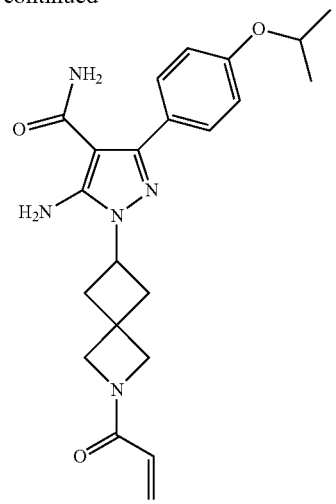

Ex 105

A vial is charged with I-70 (0.50 g, 2.67 mmol), 4-isopropoxyboronic acid (0.58 g, 3.21 mmol), tetrakis(triphenylphosphine) palladium (0) (0.43 g, 0.37 mmol) and dissolved in aqueous potassium carbonate (4 mL, 2.0 M) and DME (3 mL). The mixture is heated at 130° C. for 3 h in a microwave. The mixture is filtered then diluted with water, extracted with EtOAc, dried over sodium sulphate, filtered, and concentrated in vacuo. The residue is purified by flash chromatography (SiO$_2$, 0-80% EtOAc in heptanes) to give I-77 (0.473 g, 73%) m/z 243.5 [M+H].

Sodium hydride (60% dispersion in mineral oil, 55 mg, 1.37 mmol) is added to a solution of I-77 (300 mg, 1.24 mmol) in DMF (5 mL). The mixture is stirred for 5 min then treated with I-1 (550 mg, 1.47 mmol) and heated at 70° C. for 18 h. The solution is cooled to ambient temperature then partitioned between EtOAc and water. Organics are collected, dried, filtered, and concentrated in vacuo to afford a residue that is purified by flash chromatography (SiO$_2$, 0-100% EtOAc in heptanes) to give I-78 (200 mg, 37%) m/z 438.6 [M+H].

I-78 (190 mg, 0.43 mmol) is diluted with EtOH (4 mL) and water (2 mL) and Hydrido(dimethylphosphinous acid kP) [hydrogen bis(dimethylphosphinito-kP)]platinum (II) (11 mg, 0.026 mmol) is added. The mixture is heated at 80° C. overnight then concentrated in vacuo. The residue is dissolved in CH$_2$Cl$_2$ then filtered and concentrated to afford a residue that is dissolved in CH$_2$Cl$_2$ (5 mL) and TFA (1 mL) and stirred overnight at ambient temperature then concentrated in vacuo. The residue is dissolved in MeOH and passed through an Agilent Stratospheres PL-HCO3 MP SPE cartridge and concentrated in vacuo to afford I-79 (110 mg, 71%).

I-79 (40 mg, 0.11 mmol) and acrylic acid (10 mg, 0.14 mmol) in DMF (5 mL) is treated with HATU (88 mg, 0.17 mmol) and Hunig's base (60 μL, 0.34 mmol) in DMF (2.0 mL). The mixture is stirred overnight then concentrated in vacuo. The crude is purified by RHPLC to afford example 105 (25 mg, 54%).

The following compounds are made in similar fashion: Examples 104, 106-109, 111-113, 115-116, 124, 133, 134-136, 138-139, 141-144, 147-149, 166

Method 35

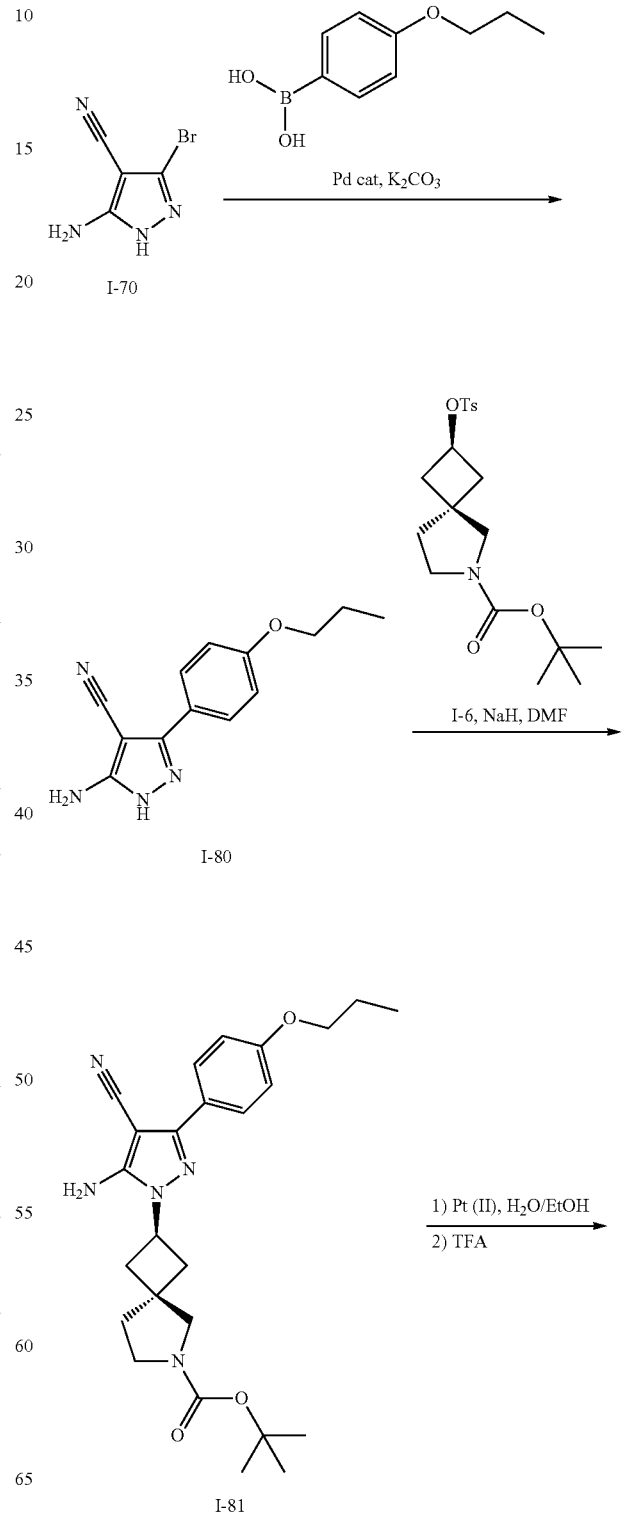

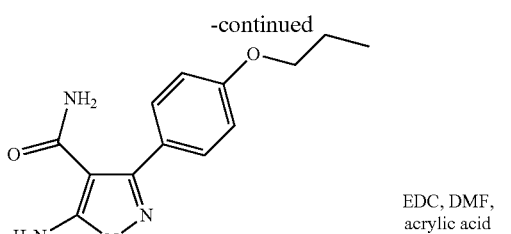

I-82

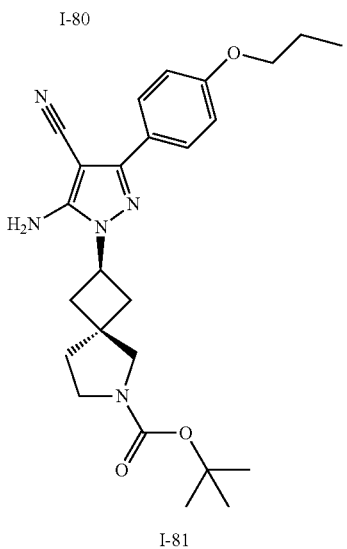

Ex 125

A vial is charged with I-70 (0.45 g, 2.41 mmol), 4-n-propoxyboronic acid (0.48 g, 2.65 mmol), tetrakis(triphenylphosphine) palladium (0) (0.28 g, 0.24 mmol) and dissolved in aqueous potassium carbonate (4.8 mL, 2.0 M) and dioxane (2 mL). The mixture is heated at 130° C. overnight. The mixture is filtered then diluted with water, extracted with EtOAc, dried over sodium sulphate, filtered, and concentrated in vacuo. The residue is purified by flash chromatography (SiO$_2$, 0-6% MeOH in CH$_2$Cl$_2$) to give I-80 (0.400 g, 69%) m/z 242.4 [M+H].

Sodium hydride (60% dispersion in mineral oil, 33 mg, 0.82 mmol) is added to a solution of I-80 (200 mg, 0.74 mmol) in DMF (5 mL). The mixture is stirred for 5 min then treated with I-6 (318 mg, 0.82 mmol) and heated at 70° C. for 18 h. The mixture is concentrated in vacuo and purified by flash chromatography (SiO$_2$, 35% EtOAc in heptanes) to give I-81 (130 mg, 39%) m/z 452.9 [M+H].

I-81 (130 mg, 0.29 mmol) is diluted with EtOH (1.5 mL) and water (0.5 mL) and Hydrido(dimethylphosphinous acid kP) [hydrogen bis(dimethylphosphinito-kP)]platinum (II) (13 mg, 0.029 mmol) is added. The mixture is heated at 80° C. overnight then concentrated in vacuo. The residue is dissolved in EtOAc then filtered and concentrated to afford a residue that is dissolved in CH$_2$Cl$_2$ (1 mL) and TFA (1 mL) and stirred for 1 h at ambient temperature then concentrated in vacuo. The residue is dissolved in MeOH and passed through an Agilent Stratospheres PL-HCO3 MP SPE cartridge and concentrated in vacuo to afford I-82 (80 mg, 84%).

I-82 (130 mg, 0.35 mmol) is treated with a prestirred (15 min) solution of acrylic acid (30 mg, 0.42 mmol) and EDC (81 mg, 0.42 mmol) in DMF (2.0 mL). The mixture is stirred overnight then diluted with aqueous saturated ammonium chloride and extracted with EtOAc. The organics are combined, dried over Na$_2$SO$_4$, filtered, and concentrated in vacuo. The crude is purified by RHPLC to afford example 125 (30 mg, 20%).

The following compounds are made in similar fashion: Examples 130, 132, 145-146, 153, 155-156, 159, 162-163, 165

Method 36

Synthesis of Example 126

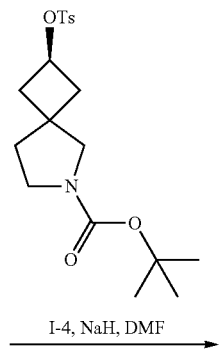

I-80

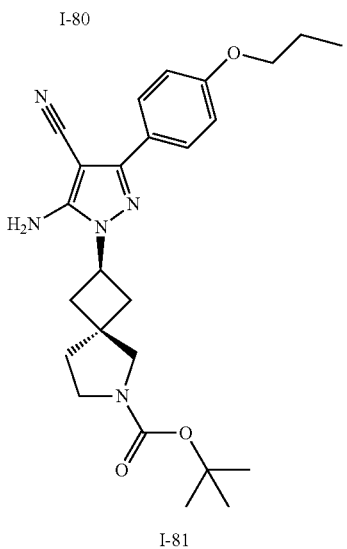

I-81

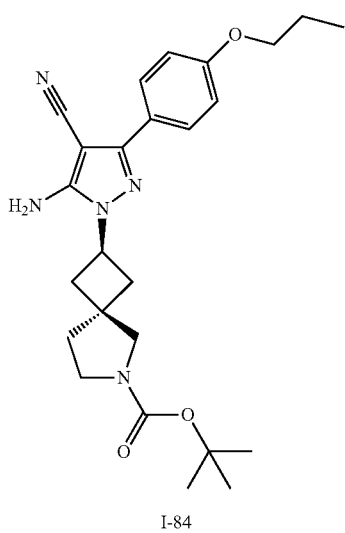

I-84

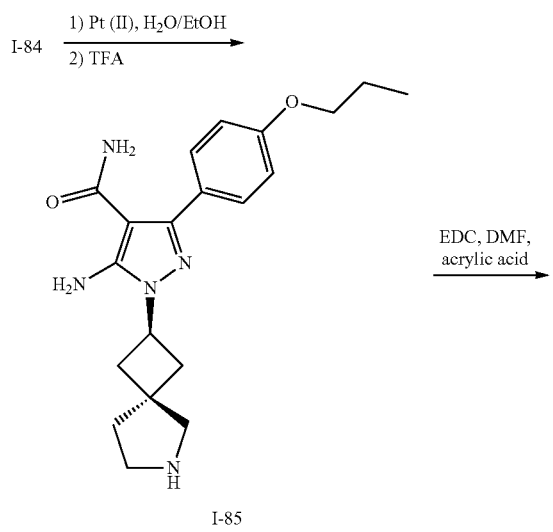

I-85

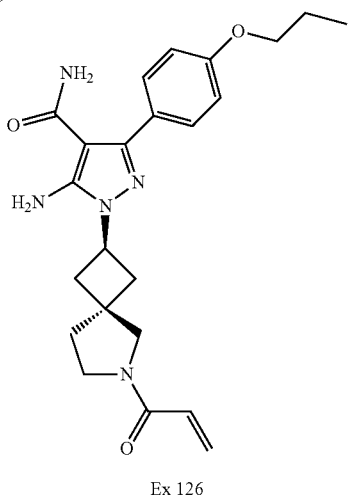

Ex 126

Sodium hydride (60% dispersion in mineral oil, 80 mg, 2.02 mmol) is added to a solution of I-80 (445 mg, 1.84 mmol) in DMF (5 mL). The mixture is stirred for 5 min then treated with I-4 (770 mg, 2.02 mmol) and heated at 70° C. for 18 h. The mixture is diluted with saturated aqueous ammonium chloride, extracted with EtOAc, dried over $Na_2SO_4$, filtered, and concentrated in vacuo. The residue is purified by flash chromatography ($SiO_2$, 0-6% MeOH in $CH_2Cl_2$) to give I-81 (200 mg, 24%) and I-84 (300 mg, 36%) m/z 452.5 [M+H].

I-84 (300 mg, 0.66 mmol) is diluted with EtOH (1.5 mL) and water (0.5 mL) and Hydrido(dimethylphosphinous acid kP) [hydrogen bis(dimethylphosphinito-kP)] platinum (II) (28 mg, 0.066 mmol) is added. The mixture is heated at 80° C. for 72 h then concentrated in vacuo. The residue is dissolved in EtOAc then filtered and concentrated to afford a residue that is dissolved in $CH_2Cl_2$ (1 mL) and TFA (1 mL) and stirred for 1 h at ambient temperature then concentrated in vacuo. The residue is dissolved in MeOH and passed through an Agilent Stratospheres PL-HCO3 MP SPE cartridge and concentrated in vacuo to afford I-85 (270 mg).

I-85 (80 mg, 0.22 mmol) is treated with a prestirred (15 min) solution of acrylic acid (19 mg, 0.26 mmol) and EDC (50 mg, 0.26 mmol) in DMF (2.0 mL). The mixture is stirred overnight then diluted with aqueous saturated ammonium chloride and extracted with EtOAc. The organics are combined, dried over $Na_2SO_4$, filtered, and concentrated in vacuo. The crude is purified by RHPLC to afford example 126 (7 mg, 8%).

The following compounds are made in similar fashion: Examples 131

Method 37

Synthesis of Example 140

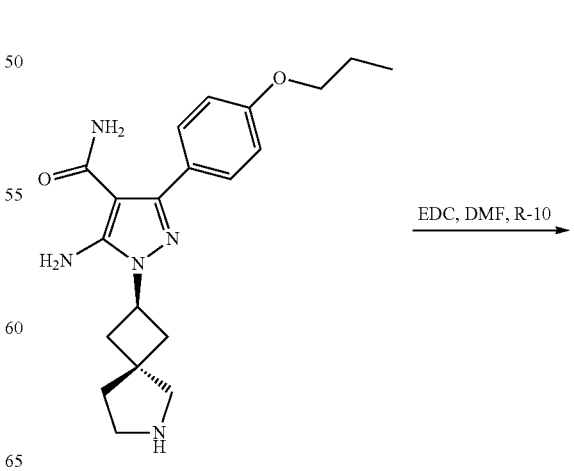

I-82

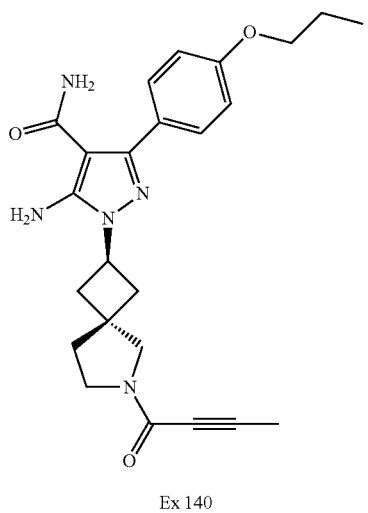

Ex 140

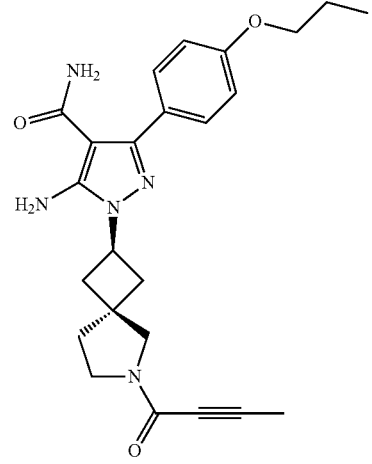

Ex 127

I-82 (80 mg, 0.22 mmol) is treated with a prestirred (15 min) solution of R-10 (24 mg, 0.28 mmol) and EDC (50 mg, 0.26 mmol) in DMF (2.0 mL). The mixture is stirred overnight then diluted with aqueous saturated ammonium chloride and extracted with EtOAc. The organics are combined, dried over $Na_2SO_4$, filtered, and concentrated in vacuo. The crude is purified by RHPLC to afford example 140 (14 mg, 15%).

The following compounds are made in similar fashion:
Example 128, 137, 154, 157-158, 160-161, 164, 167-168

Method 38

Synthesis of Example 127

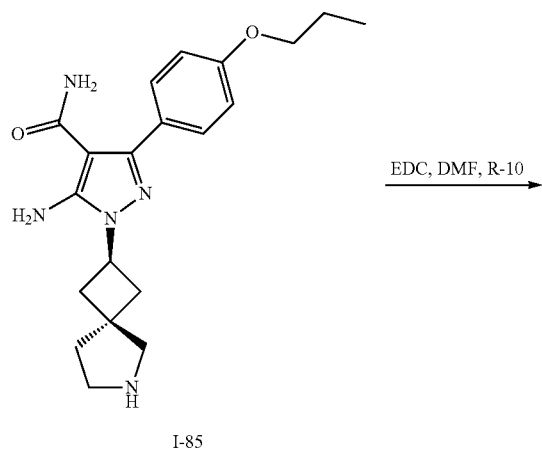

I-85

EDC, DMF, R-10 →

I-85 (70 mg, 0.19 mmol) is treated with a prestirred (15 min) solution of R-10 (21 mg, 0.25 mmol) and EDC (44 mg, 0.23 mmol) in DMF (2.0 mL). The mixture is stirred overnight then diluted with aqueous saturated ammonium chloride and extracted with EtOAc. The organics are combined, dried over $Na_2SO_4$, filtered, and concentrated in vacuo. The crude is purified by RHPLC to afford example 127 (13 mg, 16%).

The following compounds are made in similar fashion:
Example 129

Description of Biological Properties

BTK Assay

An HTRF assay (Cisbio KinEASE-TK cat #62TKOPEC) was performed to quantitate the ability of test compounds to inhibit BTK mediated phosphorylation of substrate. Assays were assembled in 384 well plates where 6 nM of full-length human His-tagged BTK (Life Technologies cat # PV3587) and test compound at varying concentrations were preincubated for 15 minutes at 28° C. Then, 1 uM of TK substrate-biotin and 30 uM ATP were added and incubated for an additional 30 minutes at 28° C. Phosphorylation was detected by adding 62.5 nM Streptavidin-XL665 and TK-Antibody Cryptate diluted 1:100 in HTRF detection buffer (Cisbio cat #62SDBRDF) and incubated for 60 minutes at RT. The plate was read on an Envision plate reader and the fluorescence is measured at 620 nm (cryptate) and 665 nm (XL665). A ratio is calculated (665/620) and converted to POC relative to control and blank wells.

Assay Buffer:

50 mM HEPES (Invitrogen #15630), 0.01% Brij-35 (sigma #B4184), 10 mM $MgCl_2$ (Sigma M1028), 1 mM EGTA (Ambion AM9262) and 100 uM sodium orthovanadate (Sigma S6508), 1 mM DTT (Sigma D5545) and 10 nM supplement enzyme buffer (Cisbio cat#61SEBALB).

Preferred compounds for the treatment of autoimmune disorders exhibit selective inhibition of BTK over other kinases such as EGFR. The compounds described herein show a range of selectivities against EGFR as measured in cellular assays (BTK activity measured by CD69 expression in primary CD19[+] cells; EGFR activity measured by EGFR phosphorylation in A431 cells). See Table II.

TABLE II

| Example | B-cell CD69 IC$_{50}$ (nM) | A431 p-EGFR IC$_{50}$ (nM) |
|---|---|---|
| 54 | 1.2 | 6.6 |
| 46 | 2.0 | 120 |
| 161 | 2.1 | 400 |
| 164 | 1.5 | 420 |
| 41 | 1 | 430 |
| 81 | 0.9 | 790 |
| 160 | 4.5 | 1200 |
| 78 | 2.5 | 1800 |
| 165 | 10 | 3700 |
| 107 | 8.2 | 4200 |
| 28 | 9 | 4700 |
| 163 | 15 | 5200 |
| 112 | 41 | 5800 |
| 113 | 24 | 6300 |
| 115 | 7.8 | 6400 |
| 40 | 20 | >10000 |
| 106 | 30 | >10000 |
| 158 | 58 | >10000 |

Inhibition of B-Cell Activation Measured by CD69 Expression

Primary CD19$^+$ cells were purified from healthy frozen peripheral blood mononuclear cells (AllCells, Emeryville, Calif.) and negatively selected by magnetic separation, >97% purity (Stemcell Technologies, Vancouver, Calif.). Cells were collected and plated in a 96 flat bottom plate at a concentration of 2×10$^5$/well in RPMI media containing 10% FBS, rested for 1 hour at 37° c. Cells were treated with inhibitor in duplicates or vehicle control in 1% DMSO final concentration for 1 hour at 37° c., 5% CO$_2$. Cells were then stimulated with 12.5 ug/ml Goat F(ab')$_2$ anti-human IgD (SouthernBiotech, Birmingham, Ala.) for 18-24 hours at 37° C., 5% CO$_2$. Cells were collected and stained for APC-CD19, clone HIB19 and PE-CD69, clone FN50 (antibodies purchased from BD Bioscience, San Jose, Calif.). B cells were analyzed by flow cytometry using a BD LSRII or BD FACsCanto Flow Cytometer. Viable cells were gated, and CD69 percentage was determined using FlowJo software.

Inhibition of EGFR Autophosphorylation in A431 Human Epithelial Cells Stimulated with Epithelial Growth Factor A431 cells (ATCC # CRL-1555 FZ) are thawed and plated in DMEM containing 10% FBS in a 384-well tissue culture treated plate at 15,000 cells/well. After incubating for 24 hours at 37° C., 5% CO$_2$, the cells are treated with test compound (1% DMSO final concentration) and incubated for 16 hours at 37° C., 5% CO$_2$. EGF (Millipore, 01-107) is added at a final concentration of 60 ng/mL and incubated for 10 minutes. The medium is removed, the cells are lysed, and phospho EGFR is measured (Meso Scale Diagnostics, N31CB-1).

Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good inhibitory effect upon BTK.

Such diseases include for example: rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis.

The compounds of formula (I) may be used on their own or in combination with other active substances according to the invention, optionally also in combination with other pharmacologically active substances.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

All patent and non-patent documents or literature cited in this application are herein incorporated by reference in their entirety.

The invention claimed is:
1. A compound chosen from:

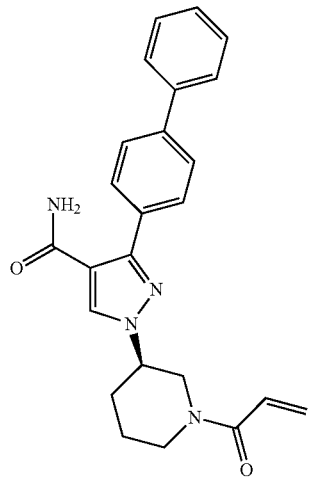 [SMILES: C=CC(=O)N1CCC[C@@H](n2cc(C(N)=O)c(-c3ccc(-c4ccccc4)cc3)n2)C1]

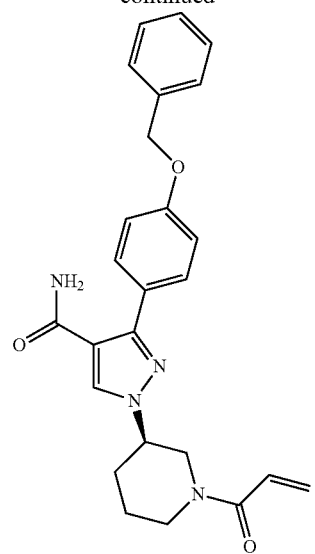

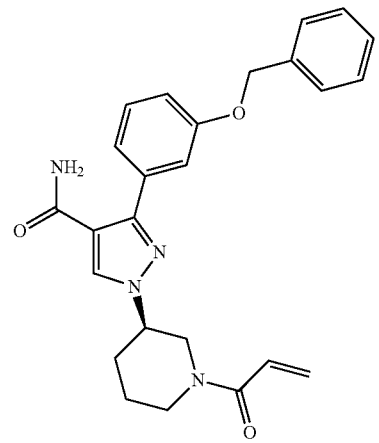

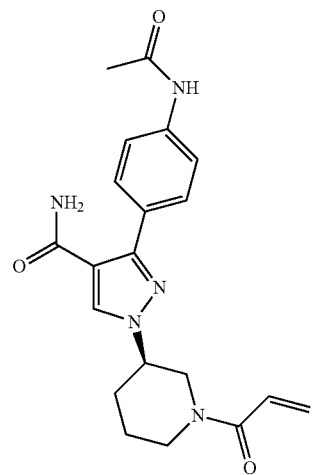

217
-continued
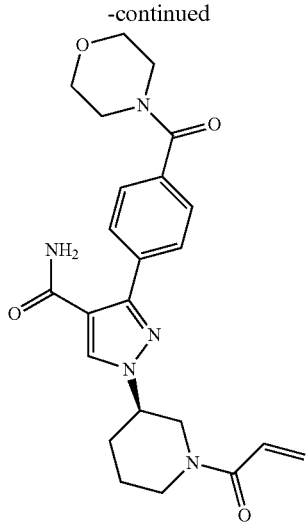
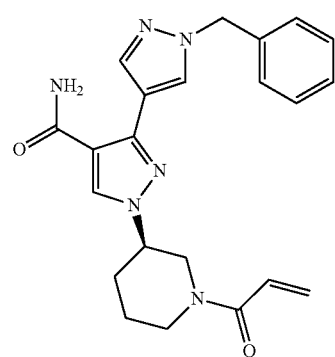
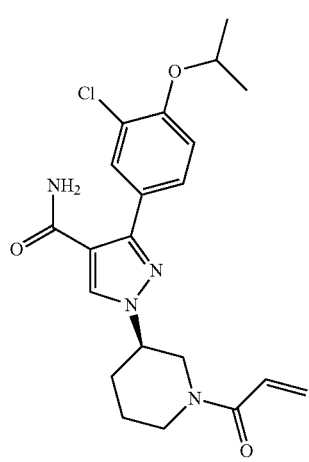
218
-continued
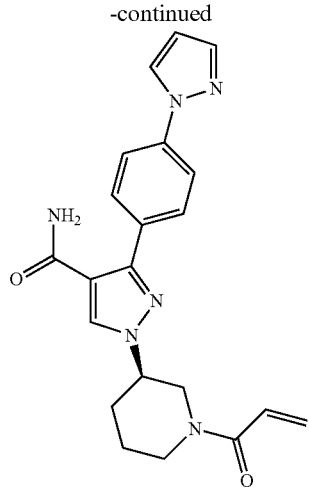
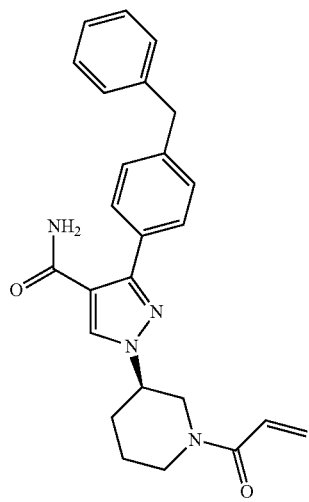
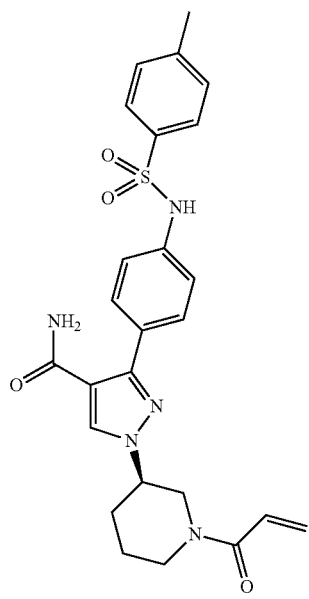

219
-continued
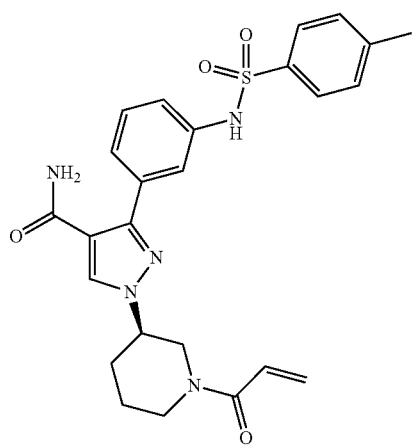
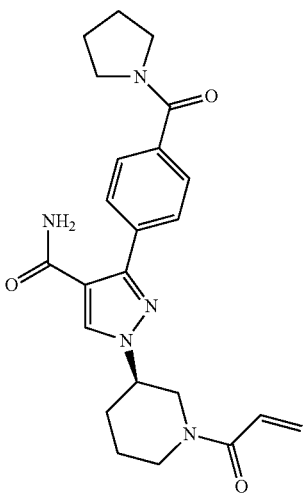
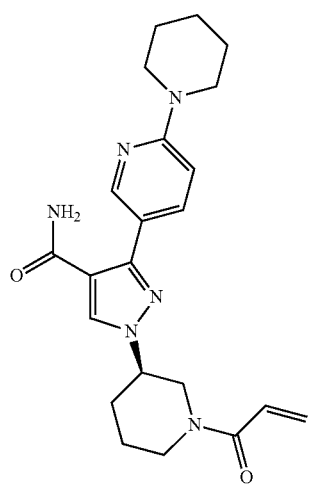
220
-continued
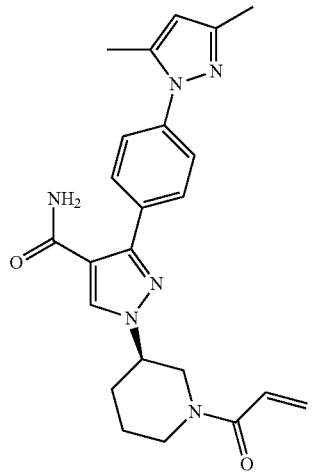
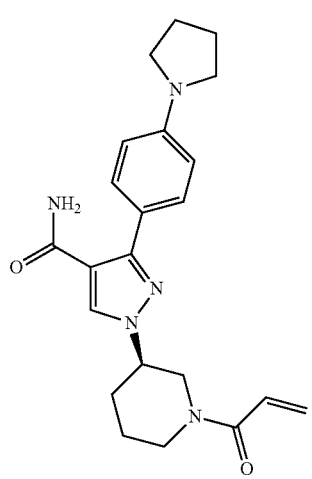
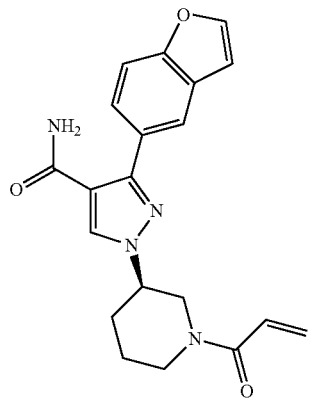

-continued
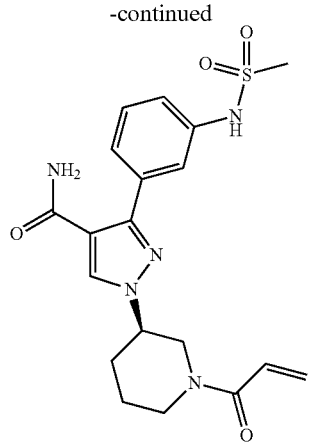
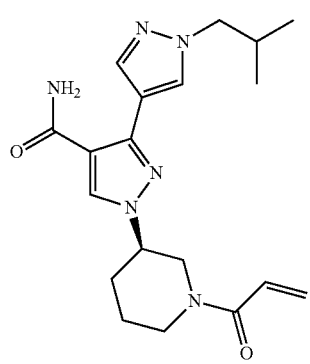
or a pharmaceutically acceptable salt thereof.
2. The compound according to claim 1 of formula:
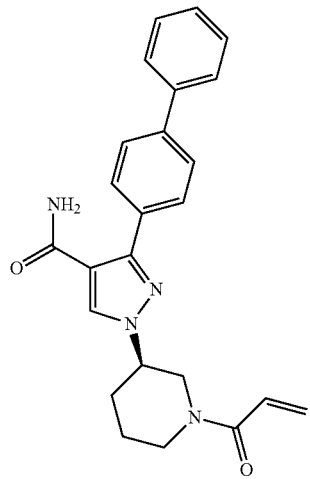
or a pharmaceutically acceptable salt thereof.
3. The compound according to claim 1 of formula:
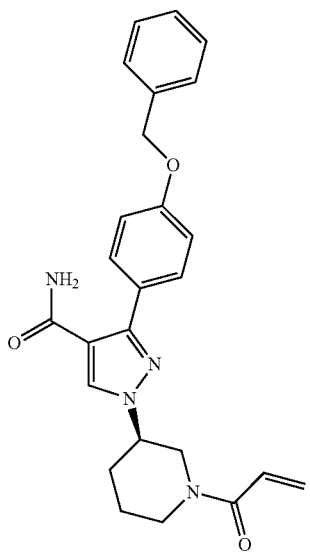 [SMILES: C=CC(=O)N1CCC[C@@H](n2cc(C(N)=O)c(-c3ccc(OCc4ccccc4)cc3)n2)C1]
or a pharmaceutically acceptable salt thereof.
4. The compound according to claim 1 of formula:
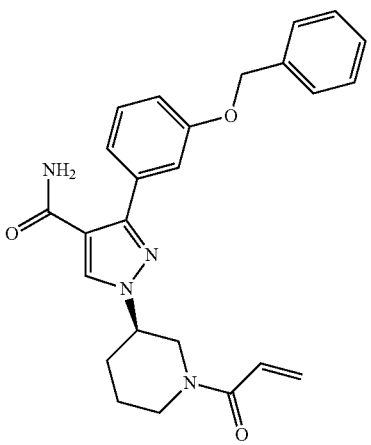 [SMILES: C=CC(=O)N1CCC[C@@H](n2cc(C(N)=O)c(-c3cccc(OCc4ccccc4)c3)n2)C1]
or a pharmaceutically acceptable salt thereof.

5. The compound according to claim 1 of formula:

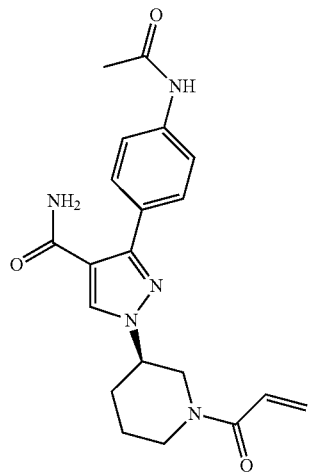 [SMILES: C=CC(=O)N1CCC[C@@H](n2cc(C(N)=O)c(-c3ccc(NC(C)=O)cc3)n2)C1]

or a pharmaceutically acceptable salt thereof.

6. The compound according to claim 1 of formula:

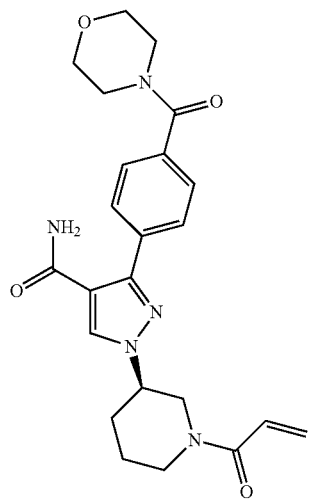 [SMILES: C=CC(=O)N1CCC[C@@H](n2cc(C(N)=O)c(-c3ccc(C(=O)N4CCOCC4)cc3)n2)C1]

or a pharmaceutically acceptable salt thereof.

7. The compound according to claim 1 of formula:

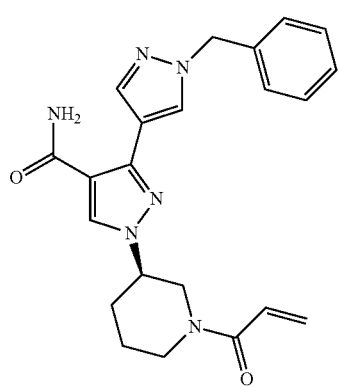 [SMILES: C=CC(=O)N1CCC[C@@H](n2cc(C(N)=O)c(-c3cnn(Cc4ccccc4)c3)n2)C1]

or a pharmaceutically acceptable salt thereof.

8. The compound according to claim 1 of formula:

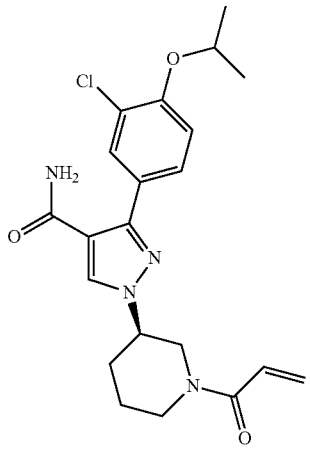 [SMILES: C=CC(=O)N1CCC[C@@H](n2cc(C(N)=O)c(-c3ccc(OC(C)C)c(Cl)c3)n2)C1]

or a pharmaceutically acceptable salt thereof.

9. The compound according to claim 1 of formula:

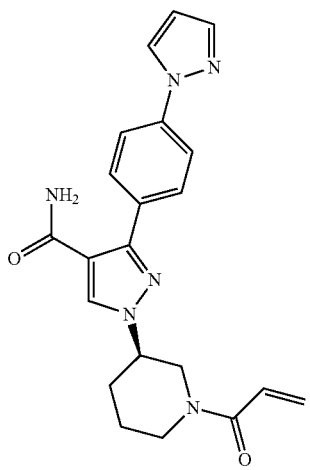 [SMILES: C=CC(=O)N1CCC[C@@H](n2cc(C(N)=O)c(-c3ccc(-n4cccn4)cc3)n2)C1]

or a pharmaceutically acceptable salt thereof.

10. The compound according to claim 1 of formula:

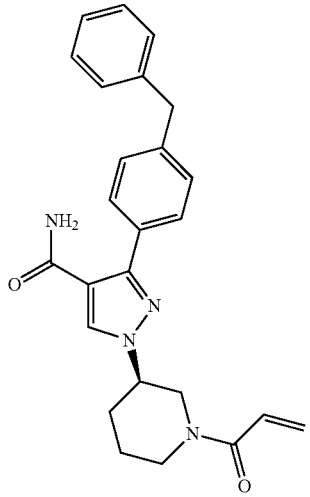 [SMILES: C=CC(=O)N1CCC[C@@H](n2cc(C(N)=O)c(-c3ccc(Cc4ccccc4)cc3)n2)C1]

or a pharmaceutically acceptable salt thereof.

11. The compound according to claim 1 of formula:

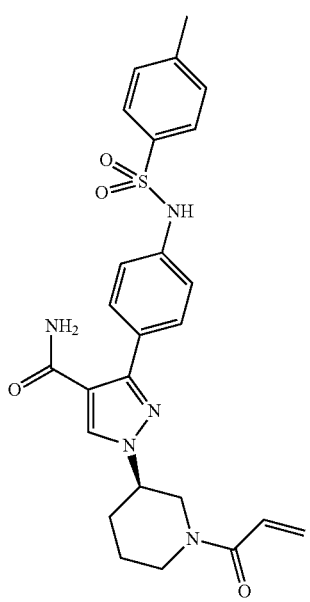 [SMILES: C=CC(=O)N1CCC[C@@H](n2cc(C(N)=O)c(-c3ccc(NS(=O)(=O)c4ccc(C)cc4)cc3)n2)C1]

or a pharmaceutically acceptable salt thereof.

12. The compound according to claim 1 of formula:

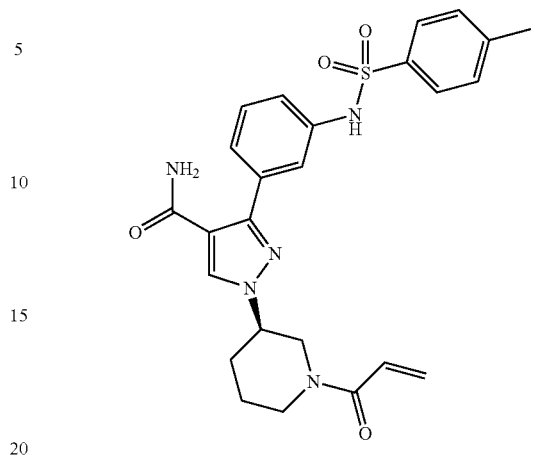

or a pharmaceutically acceptable salt thereof.

13. The compound according to claim 1 of formula:

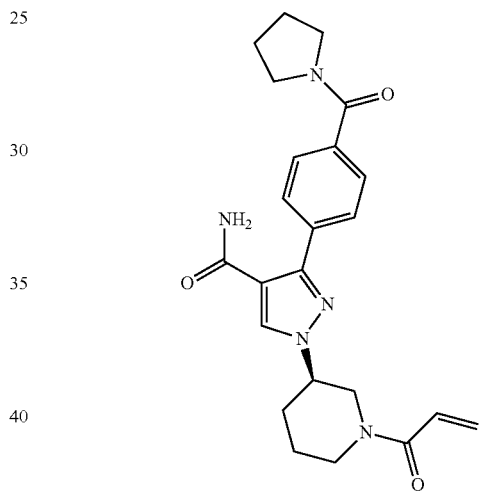

or a pharmaceutically acceptable salt thereof.

14. The compound according to claim 1 of formula:

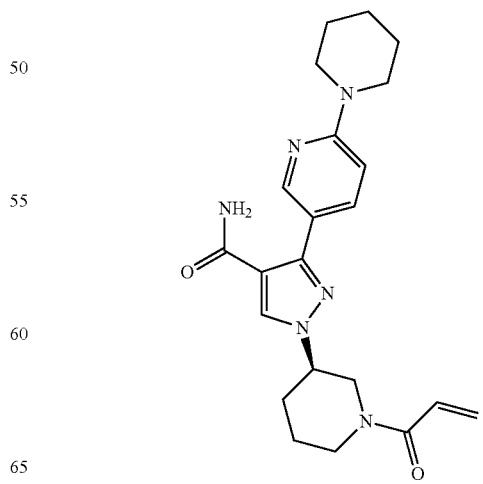

or a pharmaceutically acceptable salt thereof.

15. The compound according to claim 1 of formula:

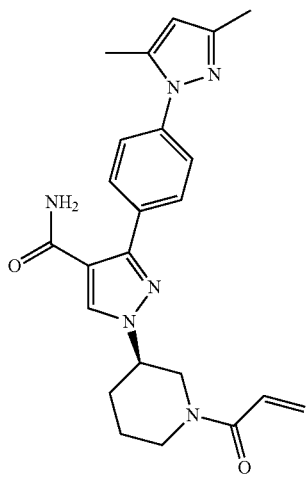 [SMILES: C=CC(=O)N1CCC[C@@H](n2cc(C(N)=O)c(-c3ccc(-n4nc(C)cc4C)cc3)n2)C1]

or a pharmaceutically acceptable salt thereof.

16. The compound according to claim 1 of formula:

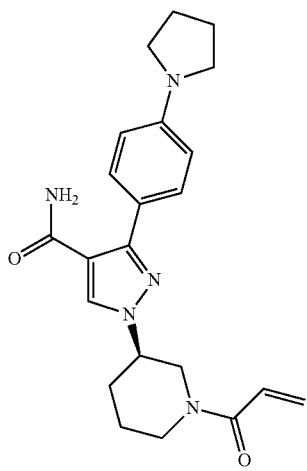 [SMILES: C=CC(=O)N1CCC[C@@H](n2cc(C(N)=O)c(-c3ccc(N4CCCC4)cc3)n2)C1]

or a pharmaceutically acceptable salt thereof.

17. The compound according to claim 1 of formula:

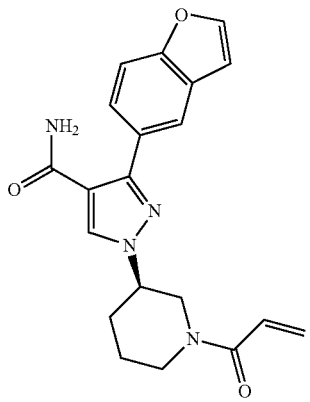 [SMILES: C=CC(=O)N1CCC[C@@H](n2cc(C(N)=O)c(-c3ccc4occc4c3)n2)C1]

or a pharmaceutically acceptable salt thereof.

18. The compound according to claim 1 of formula:

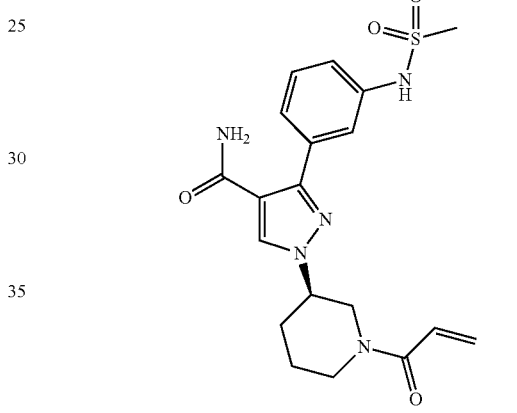

or a pharmaceutically acceptable salt thereof.

19. A pharmaceutical composition comprising a therapeutically effective amount of a compound according to claim 1 or a pharmaceutically acceptable salt thereof.

20. A method of treating a disease chosen from rheumatoid arthritis, systemic lupus erythromatosis, scleroderma, asthma, allergic rhinitis, allergic eczema, B cell lymphoma, multiple sclerosis, juvenile rheumatoid arthritis, juvenile idiopathic arthritis, inflammatory bowel disease, graft versus host disease, psoriatic arthritis, ankylosing spondylitis and uveitis, comprising administering to a patient a therapeutically effective amount of a compound according to claim 1 or a pharmaceutically acceptable salt thereof.

\* \* \* \* \*